United States Patent [19]

Pomato et al.

[11] Patent Number: 5,965,106

[45] Date of Patent: *Oct. 12, 1999

[54] IN VIVO BINDING PAIR PRETARGETING

[75] Inventors: Nicholas Pomato, Frederick, Md.; Richard P. McCabe, West Chester, Pa.; Gregory A. Hawkins, Madison, Wis.; Reinhard Bredehorst, Hamburg, Germany; Chong-Ho Kim, Rockville, Md.; Carl-Wilhelm Vogel, Hamburg, Germany

[73] Assignee: PerImmune Holdings, Inc., Rockville, Md.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/461,267

[22] Filed: Jun. 5, 1995

Related U.S. Application Data

[63] Continuation-in-part of application No. 08/140,186, Nov. 4, 1993, Pat. No. 5,578,289, which is a continuation-in-part of application No. 07/846,453, Mar. 4, 1992, abandoned.

[51] Int. Cl.⁶ .................. A61K 39/395; A61K 51/00; A61K 51/10
[52] U.S. Cl. ............... 424/1.53; 424/1.57; 424/178.1; 424/179.1; 424/181.1; 424/183.1
[58] Field of Search ................. 424/1.53, 1.57, 424/178.1, 179.1, 181.1, 183.1

[56] References Cited

U.S. PATENT DOCUMENTS

| | | | |
|---|---|---|---|
| 4,002,532 | 1/1977 | Weltman et al. | 435/7.91 |
| 4,468,469 | 8/1984 | Atkinson | 435/7.1 |
| 4,661,347 | 4/1987 | Muller-Eberhard et al. | 530/391.9 |
| 4,762,707 | 8/1988 | Jansen et al. | 424/180.1 |
| 4,975,278 | 12/1990 | Senter et al. | 424/178.1 |

FOREIGN PATENT DOCUMENTS

| | | |
|---|---|---|
| 2005162 | 6/1991 | Canada . |
| A-2 384 262 | 10/1978 | France . |
| 1595101 | 8/1981 | United Kingdom . |
| WOA-91-08770 | 6/1991 | WIPO . |

OTHER PUBLICATIONS

H. Nygren et al., *Journal of Immunological Methods*, 85:87–95 (1985).
B. Birdsall et al., *Biochemistry*, 28:2297–2305, Easton, PA, USA, (1989).
M.V. Pimm et al., *British Journal of Cancer*, 61:508–513, (1990).
T.J. McCallister et al., *FASEB Journal* 2, 4:A690:Abstract No. 2284, Mar. 1988.
A.D. Broom et al., *J. Med. Chem.*, 32:2–7, (1989).
J. Inglese et al., *J. Med. Chem.*, 32:937–949 (1989).
R.B. Silverman et al., *Medicinal Research Reviews*, 4:3:415–447 (1984).
R.R. Rando et al., *Methods in Enzymology*, 46:28–41, (1977).
P. Blackburn et al., *The Enzymes*, xv:317–433 (1982).
F.S. Lee er al., *Biochemistry*, 28:225–230 (1989).
H.J. Hansen et al., *Chemical Abstracts*, 115:Abstract No. 205931u, 1991.
Appelman et al., *Journal of Biological Chemistry*, 263:21:10304–10313, 1988.
M. Pimm et al., *British Journal of Cancer*, 61:508–513 (1990).
T. McCallister et al., *FASEB Journal* 2, 4:Abstract No. 2284, 1988.
Neuberger MS, Williams GT, et al, (1984) Recombinant antibodies possessing novel effector functions. Nature 312:604–608.

*Primary Examiner*—Lora M. Green
*Attorney, Agent, or Firm*—Mary E. Gormley

[57] ABSTRACT

A method for in-vivo targeting a functional moiety in a patient by administering a targeting moiety coupled to an affinity component, wherein the targeting moiety has affinity for binding sites in a target area, and administering a binding partner to the affinity component coupled to a functional moiety to localize the functional moiety in the target area. Preferably the targeting moiety is an antibody and the functional moiety is a radiometal when performing in vivo imaging or therapy. The affinity component may be a novel methotrexate analog. Preferably, the affinity component is thermo-stabilized.

2 Claims, 42 Drawing Sheets

| Treatment of the affinity component | Bound [$^3$H]-MTX | |
|---|---|---|
| | CPM | % Bound |
| No | 147507 | 100 |
| 24 hrs, 4°C | 122430 | 83 |
| 24 hrs, 37°C | 25076 | 17 |

| Crosslinking | Catalytic Activity (% Control) | | |
|---|---|---|---|
| Crosslinker/affinity component (mole/mole) | After derivatization | Incubation, 37°C 2 hrs | 4 hrs |
| A. HOMOBIFUNCTIONAL IMIDOESTERS : | | | |
| DMA (200:1) | 100 | 94 | 68 |
| DMP (200:1) | 95 | 88 | 80 |
| DMS (200:1) | 95 | 37 | 24 |
| B. HETEROBIFUNCTIONAL PHOTOREACTIVE CROSSLINKERS : | | | |
| Sulfo-SANPAH (20:1) | 29 | - | - |
| (10:1) | 64 | 6 | 8 |
| C. HOMOBIFUNCTIONAL NHS-ESTERS: | | | |
| Sulfo-DST (10:1) | 55 | 7 | 4 |
| D. ZERO-LENGTH CROSSLINKERS : | | | |
| EDC (20:1) | 90 | 74 | 56 |

Dimethyladipimidate (DMA); Dimethylpimelimidate (DMP); Dimethylsuberimidate (DMS); Sulfosuccinimidyl-6-(4'-azido-2'-nitrophenylamino)-hexanoate (Sulfo-SANPAH); Disulfosuccinimidyl tartarate (sulfo-DST); 1-ethyl-3-(3-dimethylaminopropyl) carbodiimide (EDC)

FIG. 3

BINDING CONDITION

| Medium | Temperature (°C) | MTX (mole of MTX /mol of affinity component) | Bound [$^3$H] MTX (% Control) |
|---|---|---|---|
| A. Buffer | 37 | 1.2 | 100 |
| B. Serum | 37 | 0 | 2 |
|  | 37 | 12 | 48 |
|  | 37 | 36 | 49 |

FIG. 26

| | | INCUBATION CONDITIONS | |
|---|---|---|---|
| Medium | Temp (°C) | Addition of MTX (mol MTX / mol of affinity component) | Remaining [$^3$H] MTX-binding Activity after 24hrs (%Control) |
| Buffer | 4 | 0 | 100 |
| | 37 | 0 | 28 |
| | | 1.3 | 65 |
| Serum | 4 | 1.3 | 100 |
| | 37 | 3 | 83 |
| | | 6 | 91 |
| | | 9 | 90 |

FIG. 28

| Medium | Temp (°C) | INCUBATION CONDITIONS Addition of MTX (mol MTX / mol of affinity component) | Remaining [$^3$H] MTX-binding Activity after 24hrs (%Control) |
|---|---|---|---|
| Buffer | 4 | 0 | 100 |
|  | 37 | 0 | 8 |
|  |  | 1.3 | 69 |
| Serum | 4 | 1.3 | 100 |
|  | 37 | 3 | 40 |
|  |  | 9 | 50 |

FIG. 30

| AFFINITY COMPONENT | MEDIUM | RETENTION OF ACTIVITY (after 24 hrs at 37°C) | |
|---|---|---|---|
| | | Catalytic Activity (%) | Binding Activity (%) |
| Wild Type | Buffer | 18* | 17 |
| | Serum | 12* | 2 |
| Single Mutation | Buffer | 37 | 23 |
| | Serum | 27 | 19 |
| Double Mutation | Buffer | 53 | 50 |
| | serum | 10 | 20 |

\* Data obtained with wild-type rhDHFR thermostabilized via derivatization with DMP (compare Fig.4)

FIG. 31

DTPA-Glu-Ala-Lys-Ala-Glu-Ala-Lys-Ala-Glu-Ala-Lys-Ala
             |                           |                         |
            X                        X                      X

Where  X = MTX-Y
and,    Y = DTPA-LiLo

FIG. 33

APA=4-amino-4-deoxy-N[10]-methylpteroic acid    peptide synthesis

EFFECTS OF TREATING rhDHFR
WITH SULFO-LC-SPDP

| MOLAR RATIO DHFR:LC-SPDP | NUMBER SPDP INCORPORATED | % ACTIVITY REMAINING |
|---|---|---|
| 1:50 | 4 | 0 |
| 1:25 | 2 | 1.7 |
| 1:15 | 1.5 | 21 |
| 1:7 | 1 | 55 |

FIG. 40

EFFECTS OF TREATMENTS OF rhDHFR

| TREATMENT | % RECOVERY | REMAINING SP. ACTIVITY |
|---|---|---|
| NONE | ---- | 20 U/mg |
| 7 MOLAR EXCESS SULFO-LC-SPDP | 69.6 | 11 U/mg |
| 10 mM DTT AFTER SULFO-LC-SPDP | 38.0 | 16.5 U/mg |

FIG. 41

NUMBER OF ACTIVE rhDHFR

| CONJUGATE | # hDHFR/IgM |
|---|---|
| CON5-12 | <<1 |
| CON10-25 | <<1 |
| CON-LS2.1 | <<1 |
| 16-88DHFR3-1 | 3 |
| 16-88DHFR3-2 | 2-3 |
| 16-88DHFR3-3 | 2-3 |

FIG. 43

IN VIVO BINDING PAIR PRETARGETING

This application is a continuation-in-part of U.S. Ser. No. 08/140,186, filed Nov. 4, 1993 now U.S. Pat. No. 5,578,289, which is the National phase of PCT/US93/01858, filed Mar. 3, 1993, which is a continuation-in-part of U.S. Ser. No. 07/846,453, filed March 4, 1992 now abandoned.

BACKGROUND OF THE INVENTION

Currently, a broad spectrum of diagnostic and therapeutic agents is used for in vivo diagnosis and treatment of cancer and infectious diseases. Radionuclides, one important group of pharmaceutical agents, have been shown to be useful for radioimaging and radiotherapy. Radioimaging compounds include metal chelates of radioisotopes such as $^{111}$In, $^{67}$Ga, $^{99m}$Tc, or $^{57}$Co, which are used to detect cancer lesions by intravenous administration. Radiotherapeutic agents, such as metal chelates of $^{90}$Y, exert their cytotoxic effects by localized cell destruction via ionizing radiation. Radionuclides, however, suffer from a number of limitations. A particular problem is caused by their toxic side effects, which limit the dosage that may be used safely. In certain cases, adverse side effects are so severe that an effective therapeutic dose cannot be safely administered. Therefore, specific targeting of radionuclides to internal target sites, such as solid tumors, has become a major focus of current medical research. The objective of radionuclide targeting is to improve tumor to normal tissue ratios by concentrating the radioisotope at the target site, while minimizing its uptake in non-target tissues.

Monoclonal antibodies, reactive with human tumor-associated antigens, provide promising agents for the selective delivery of radionuclides. Various methods have been described for the conjugation of radionuclides to antibodies. In one procedure, the tyrosine residues of the antibody molecule are labeled with $^{131}$I. Alternatively, bifunctional chelating agents are applied to bind radioisotopes to antibodies. The bifunctional chelating agents contain as one functional group a chelating moiety capable of forming a tight complex with a metal ion, and as a second functional group a chemically reactive moiety, such as an activated ester, a nitro or amine group, through which the compounds can be coupled to the antibody. Since bifunctional chelator molecules have been shown to increase the stability of isotope antibody conjugates, the latter labeling procedure has gained favor in clinical trials. Despite some promising results, the data from these studies demonstrate that the use of radioisotope antibody conjugates has several limitations. The most important limitation is the high nonspecific uptake of the conjugates in normal tissues, such as liver, bone marrow, and kidney, leading to serious toxic side effects. As a result, some investigators have resorted to local or regional injections of radioisotope antibody conjugates in the area of known lesions, neglecting delivery to remote metastatic sites. Others have used antibody fragments as delivery agents, which have a lower molecular weight and, therefore, may penetrate deeper into tumors. However, they also exhibit high uptake in certain normal tissues resulting in a low therapeutic index.

A recent approach to overcoming these problems has been the development of bifunctional monoclonal antibodies. Such antibodies have a dual specificity, with one binding site for a disease site, e.g. a tumor target, and one binding site for a hapten, which can function as a carrier for a variety of diagnostic and therapeutic agents including radionuclides. The dual specificity allowed the development of a two step targeting procedure for radionuclides. First, the anti-hapten, anti-tumor bifunctional antibody is administered and, after a period of time sufficient for the bifunctional antibody to localize at the tumor site, the radionuclide-derivatized hapten is injected. This approach has the advantage that the non-toxic targeting moiety and the toxic radionuclide-derivatized hapten can be given separately. As a result, large quantities of the targeting moiety can be administered without the risk of serious toxic side effects. Furthermore, increased uptake ratios and faster localization of the radionuclide can be expected, since the radioactivity is attached to the low molecular weight structure of the radionuclide-derivatized hapten capable of fast distribution through the body tissues and rapid clearance through the kidneys.

The bifunctional antibody approach, however, suffers from the fact that the antibody molecule is composed of two monovalent antibody fragments with different specificities. The avidity of monovalent antibody fragments such as Fab fragments is orders of magnitude lower than that of bivalent antibody molecules. The efficacy of the two step bifunctional antibody approach, however, is dependent on high avidity binding of the bifunctional antibody to the radionuclide-derivatized hapten and to extracellular or cell surface antigens at the target site. Moreover, to allow for efficient clearance of non-bound bifunctional antibody from circulation before injection of the radionuclide-derivatized hapten, a period of 4 to 6 days is required. Using monovalent antibody fragments, complete dissociation of bound antibody molecules from the target sites is expected in this period of time. A recent study of the kinetics of antibody binding to surface-immobilized antigen demonstrated that the intact antibody, bound to the surface-immobilized antigen, did not dissociate significantly over a period of almost 3 days, whereas a monovalent Fab' fragment prepared from the same antibody dissociated from the surface-bound antigen with a half-life of 16 hours (N. Nygren, C. Czerkinsky, M. Stenberg, Dissociation of antibody bound to surface-immobilized antigen. J. Immunol. Meth. 85, 87–95, 1985).

In addition to the limitation of monovalent binding, there are problems with the current procedures for the production of bifunctional antibodies. In one method two Fab' fragments of differing specificity are chemically linked to form a F(ab)$_2$ fragment with dual specificity. The preparation of appropriate antibody fragments requires individual adjustment of the experimental conditions for each monoclonal antibody, the yields are often very low, and the hybrid antibodies usually suffer significant, irreversible denaturation. Such denaturation can reduce immunoreactivity and would be expected to result in different metabolic characteristics in vivo. Alternatively, fusion of two hybridomas or a hybridoma with immune spleen cells can be undertaken, with appropriate physical or biochemical selection of hybrid hybridomas. The theoretical maximum yield of bifunctional antibody, produced by established hybrid hybridomas, will be 50% of the total immunoglobulin synthesized, the remainder being bivalent parent antibodies. However, the actual production of bifunctional antibody can be much lower. In a recent study a bispecific monoclonal antibody against methotrexate and a human tumor associated antigen was prepared to augment the cytotoxicity of a methotrexate-carrier conjugate. (M. V. Pimm, R. A. Robins, M. J. Embleton, E. Jacobs, A. J. Markham, A. Charleston and R. W. Baldwin, Br. J. Cancer, vol.61, pp.508–513, 1990) The proportions of the total immunoglobulin recovered from the hybrid hybridoma were 60% monospecific antibody from the original hybridoma cells, 27% monospecific antibody from the immune spleen cells, and only 13% bispecific antibody, suggesting a preferential association of homologous heavy chains. These data demonstrate that it will always be necessary when using the hybrid-hybridoma technique to develop strategies for purification of the bifunctional antibody from parent antibodies being produced by the hybridoma. Since the different antibody molecules from one hybrid hybridoma share most properties, an efficient removal of the monospecific antibodies would require two affinity purification steps, a time consuming procedure known to cause partial denaturation of the purified antibodies.

The problems listed in the foregoing are not intended to be exhaustive, but rather to describe many of the factors that tend to limit the potential clinical value of the described agents. While the two-step procedure, developed for bifunctional antibodies, provides some advantages over other targeting procedures, there exists a need for a more effective means by which the concentration of a radionuclide or another diagnostic or therapeutic agent may be maintained at in vivo target sites for a period of time sufficient to achieve desired results. Further, there exists a need for an effective delivery system consisting of components that can be easily synthesized and purified at high yields.

SUMMARY OF THE INVENTION

One general object of the invention is to provide a delivery system for targeting therapeutic or diagnostic compound to an in vivo target, which substantially overcomes the limitations known in the prior art. A more specific objective of the invention is to provide methods and components for selectively targeting radionuclides to solid tumor areas.

This invention comprises a system for in vivo localization using a targeting reagent comprising a non-toxic targeting moiety coupled to a non-toxic enzyme, which will localize to a target site, and an enzyme inhibitor or enzyme substrate derivatized with a functional moiety. On administration, the derivatized enzyme inhibitor or substrate binds to the localized non-toxic enzyme coupled to the targeting moiety, presenting the functional moiety to the tissue at the target site. In the preferred embodiment the targeting moiety is an antibody or antibody fragment and the functional moiety bound to the enzyme inhibitor is a radionuclide. According to the invention the targeting moiety and enzyme are both non-toxic and minimally or non-immunogenic when coupled, and the derivatized enzyme inhibitor or substrate is also preferably weakly or poorly immunogenic and non-toxic. A further requirement for the enzyme coupled to the targeting moiety is that it be essentially absent from circulation or present in only very low quantities in circulation. With this invention there is rapid and specific localization of the targeting moiety coupled to the enzyme, and relatively rapid clearance and specific targeting of the functional moiety-derivatized enzyme inhibitor or substrate with extremely little non-specific binding. By these means highly toxic or otherwise undesirable functional moieties can be used in therapy and in imaging. This invention also comprises a novel methotrexate analog useful for making the functional moiety derivatized enzyme inhibitor and a stabilized dihydrofolate reductase enzyme.

BRIEF DESCRIPTION OF THE FIGURES

FIG. 3 shows the effect of different cross-linkers on the thermo-stabilization of the affinity component.

FIGS. 17 (A and B) show the thermo-stability of NADP-derivatized affinity component as determined by its catalytic activity.

FIGS. 18 (A,B and C) show the thermo-stability of NADP-derivatized affinity component as determined by its binding activity.

FIG. 26 shows the effect of different concentrations of MTX on the thermo-stability of the affinity component in normal human serum.

FIG. 28 shows the thermo-stabilization of the affinity component by covalent binding of DIMETHYLPIMELIMIDATE (DMP) and non-covalent binding of MTX.

FIG. 30 shows the thermo-stabilization of the affinity component by covalent binding of the ANPAP-NADP and non-covalent binding of MTX.

FIG. 31 shows the thermostability of rhDHFR mutants.

FIG. 33 shows the structure of an effector complex containing three binding partners.

Figure 39:
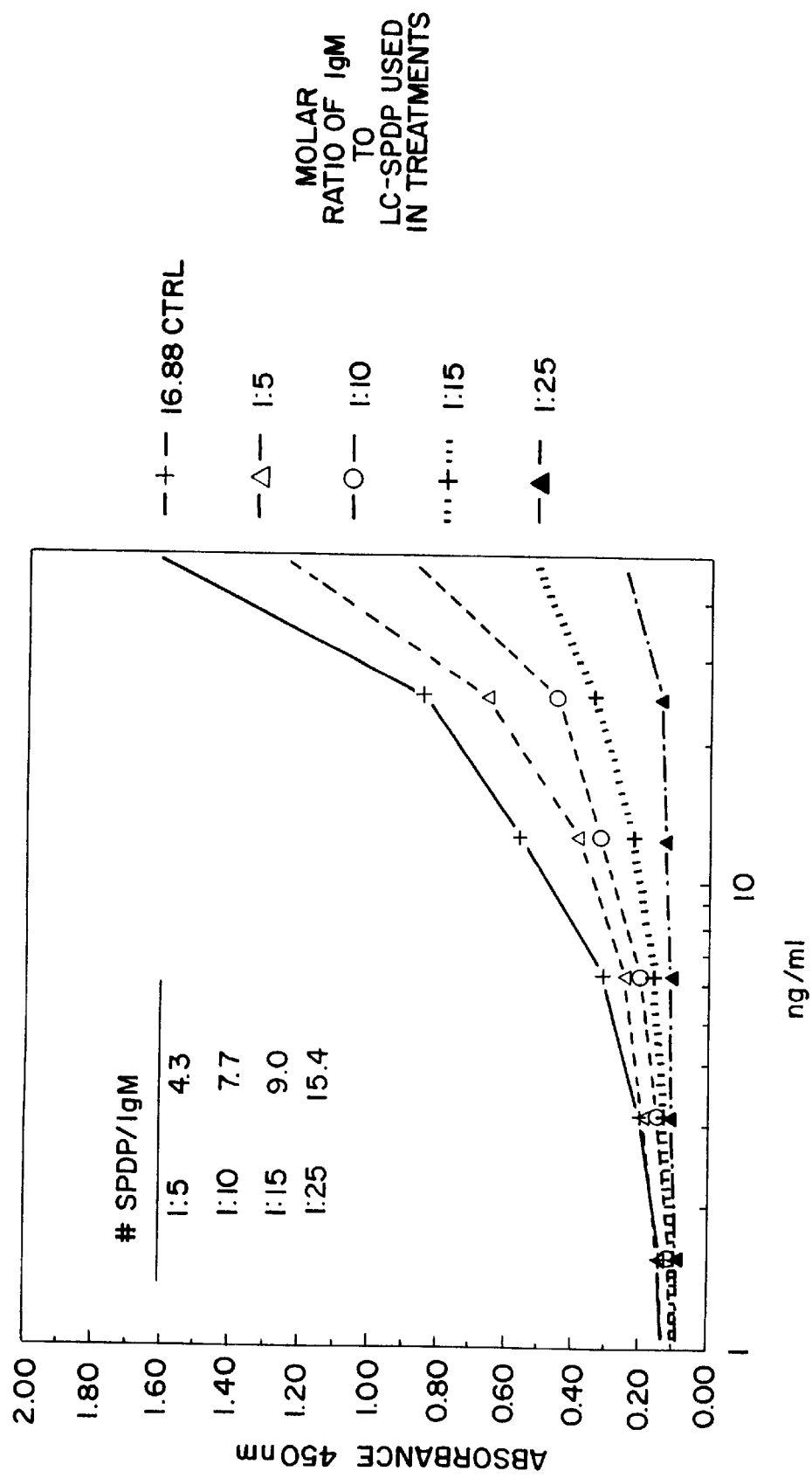

In Example 1, immunoreactivity of the SPDP modified 16.88 was determined by measuring binding to the tumor antigen CTAA-16.88 and comparing to the activity of native 16.88 (FIG. 39).

In Example 2, sulfhydryl incorporation (FIG. 40) and protein concentration determination were performed as described for the antibody.

In Example 2, the activity of rhdhfr following sulfo-LC-SPDP modification and following reduction with DTT was evaluated to determine the effects of the treatment on the activity of the enzyme (FIG. 41).

Figure 42:
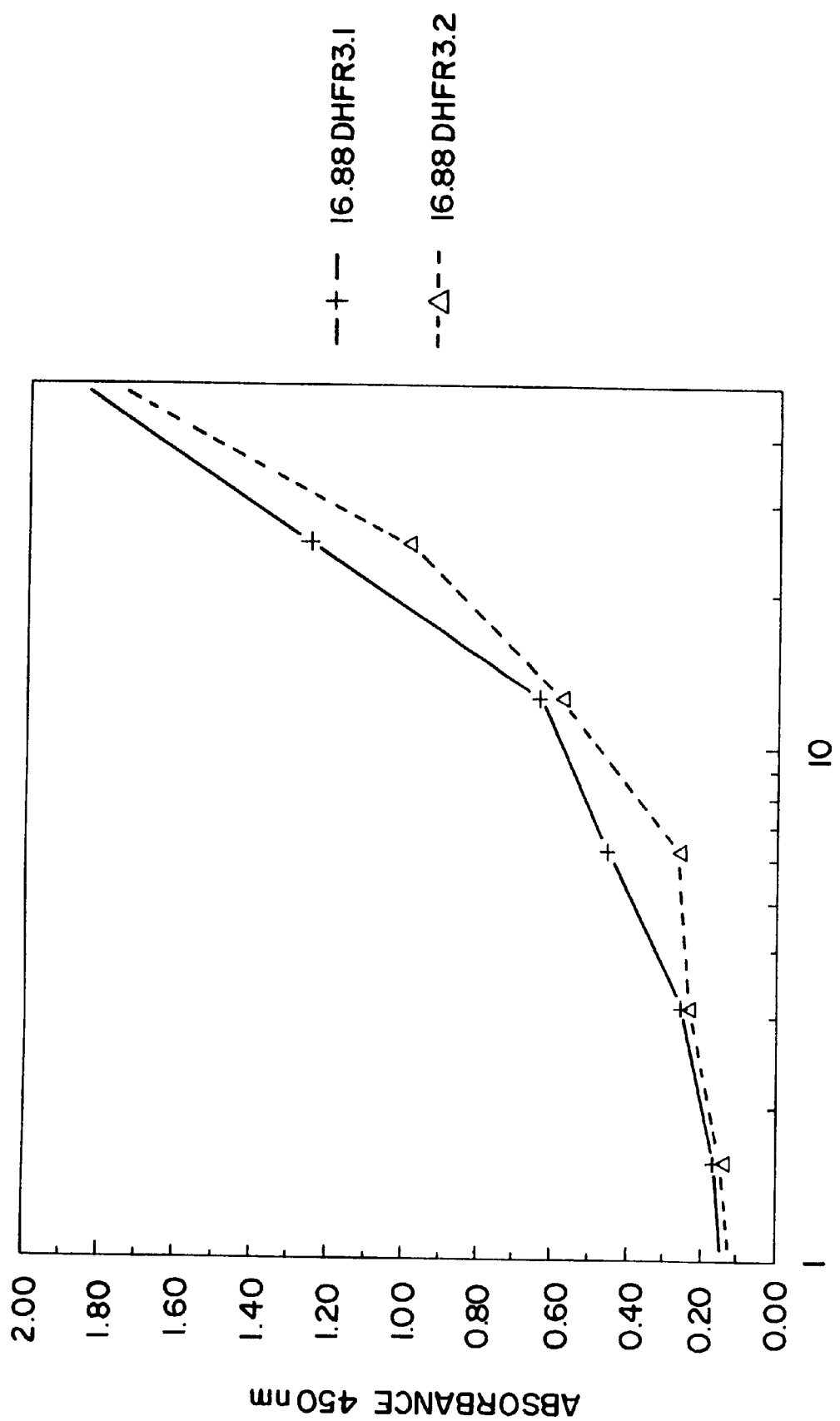
Figure 44:
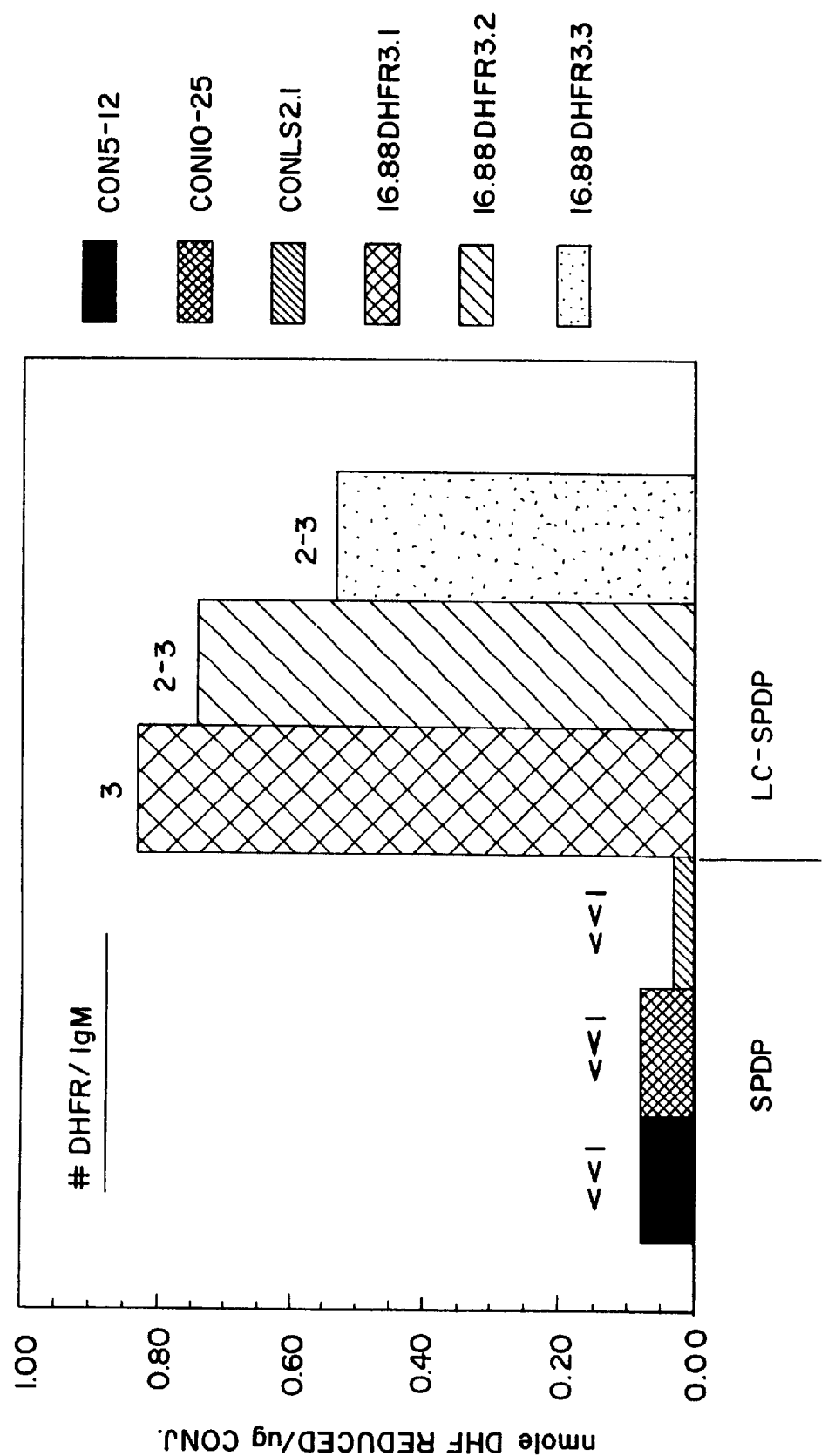

With reference to Example 3, FIG. 42 shows the immunoreactivity of two preparations of 16.88-DHFR. FIGS. 43 and 44 show the beneficial effects of using the LC-SPDP spacer compared to normal SPDP in three different conjugate preparations.

Figure 45:
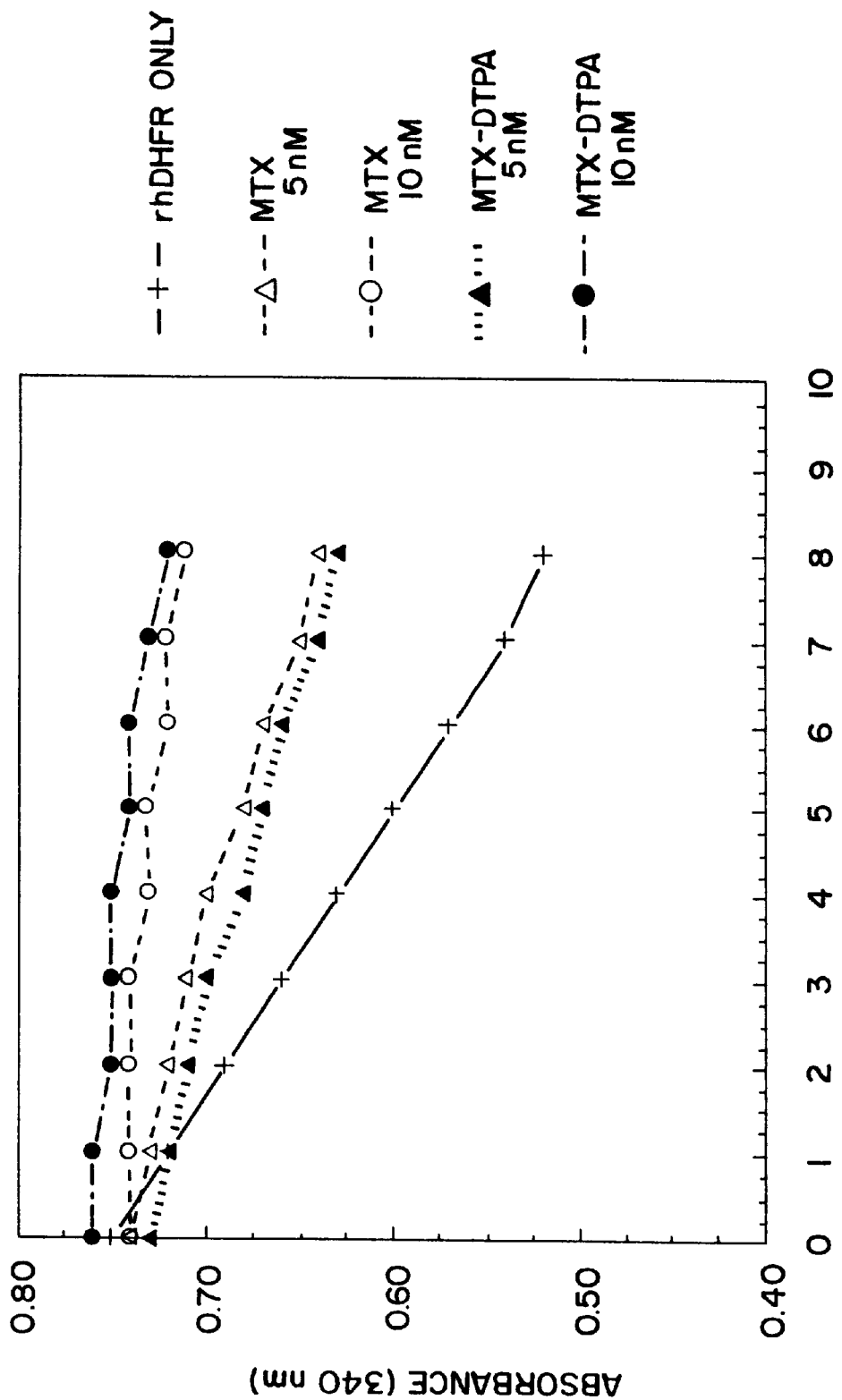

With reference to Example 5, FIG. 45 shows that at $1 \times 10^{-8}$M and $5 \times 10^{-9}$M inhibitor concentration, the inhibitory effects of DTPA-MTX were virtually identical to MTX inhibition; as indicated by the decreased rates of dihydrofolate reduction.

Figure 46:
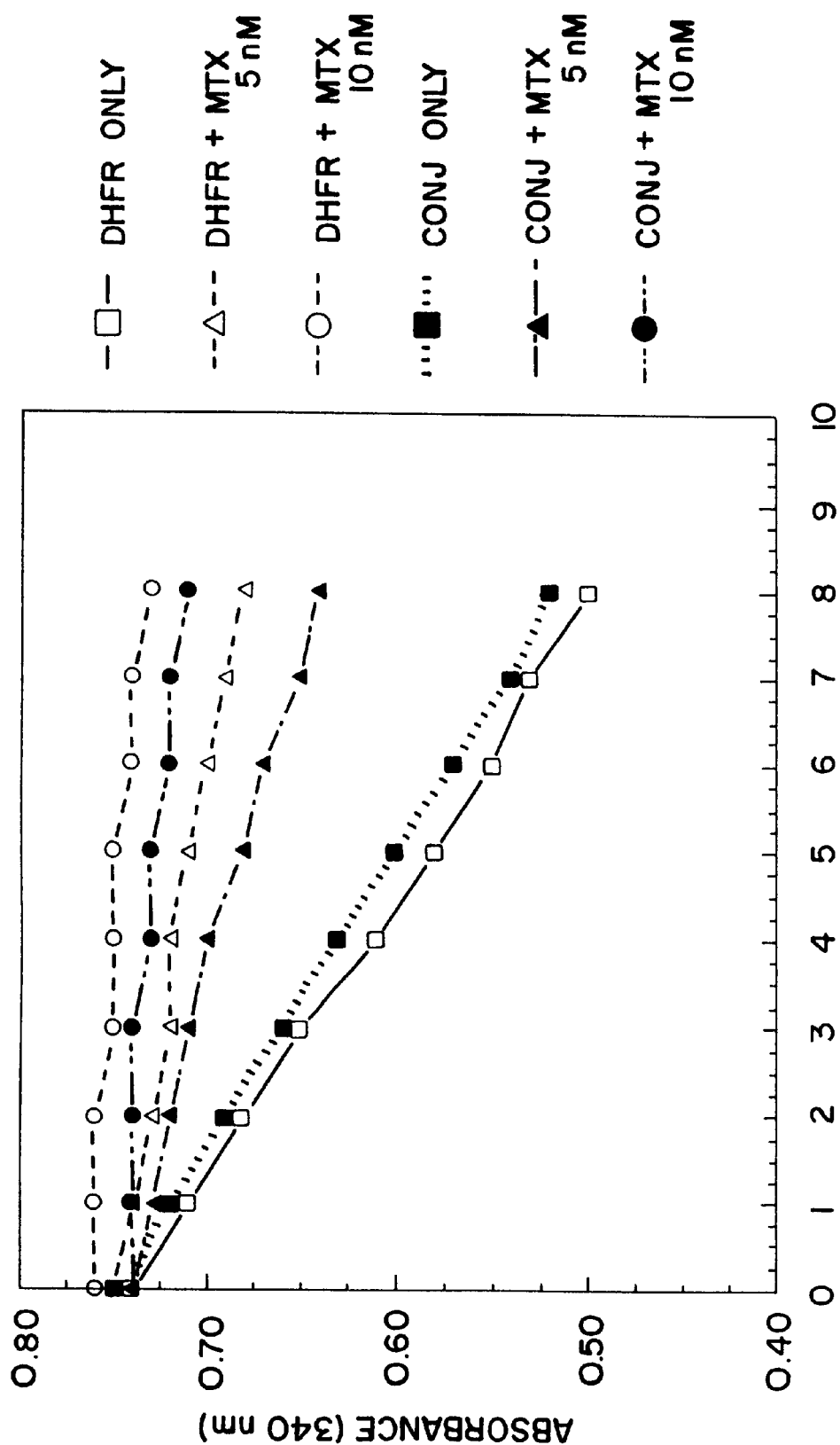
Figure 47:
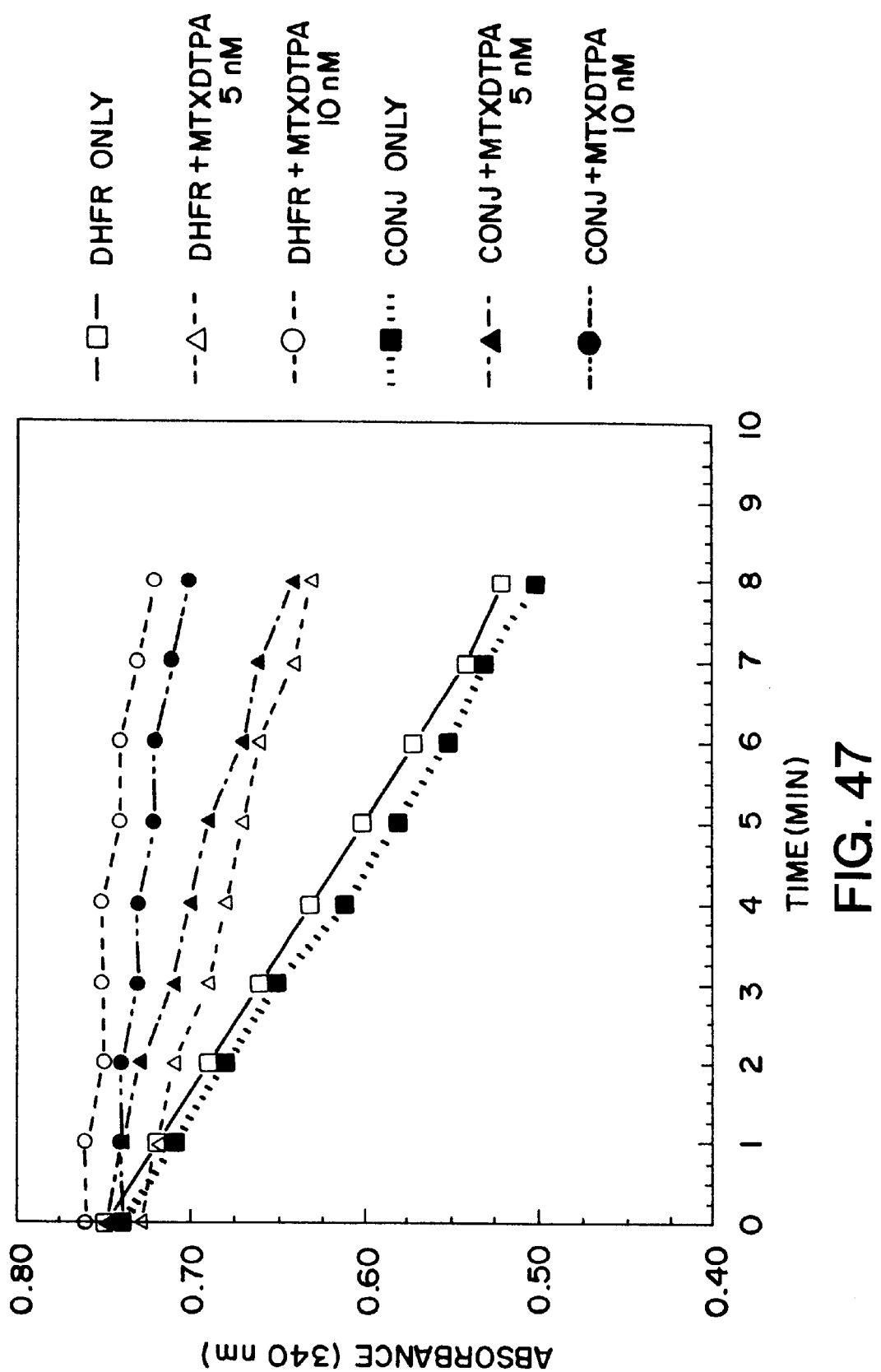

Referring to Example 6, FIG. 46 shows the results of MTX inhibition of equivalent activities of native rhDHFR and 16.88 bound rhDHFR and indicates that MTX binding is proportional to the reductase activities regardless of whether it is free or in conjugate form. An identical experiment performed using DTPA-MTX (FIG. 47) confirmed the methotrexate data.

Figure 48:
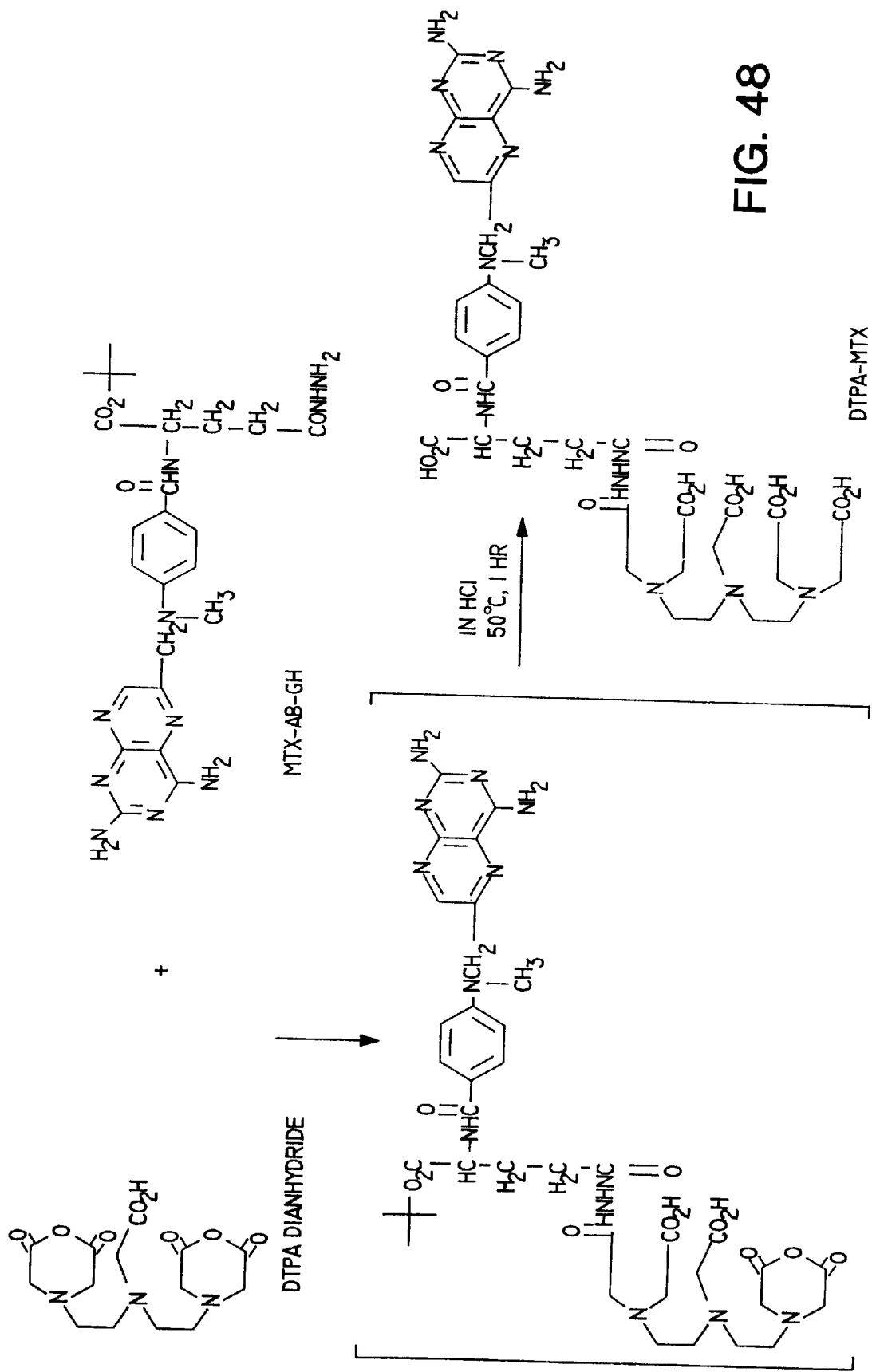

The synthesis of DTPA-MTX is shown schematically in FIG. 48.

Figure 49:
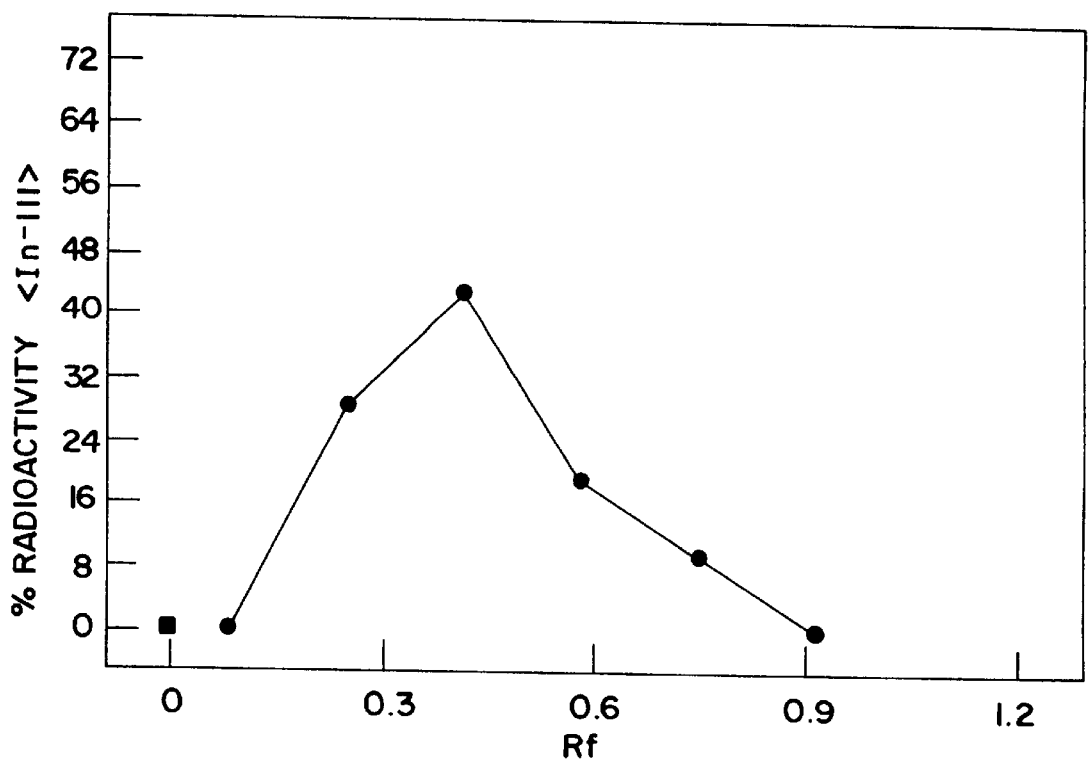

With reference to Example 8, FIG. 49 shows the migration of $^{111}$In-DTPA-MTX in the silica gel with an $R_f$ of 0.5 to 0.7. In addition, results shown in FIG. 50 indicate that the In-DTPA-MTX and the $^{111}$In-DTPA clear from the mice at similar rates indicating the likelihood of rapid urinary excretion of a DTPA-MTX not bound to antibody-DHFR.

Figure 51:
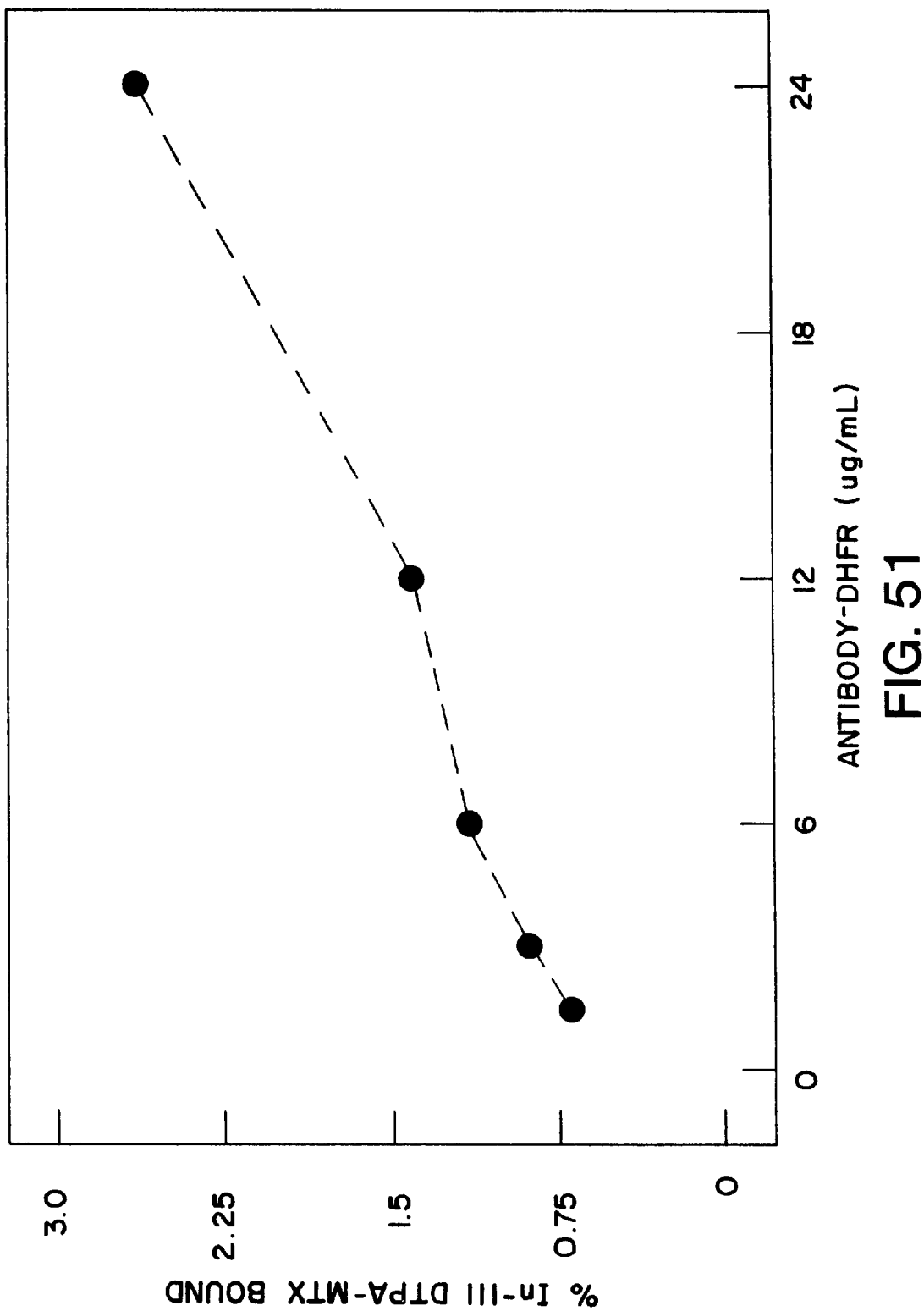
Figure 52:
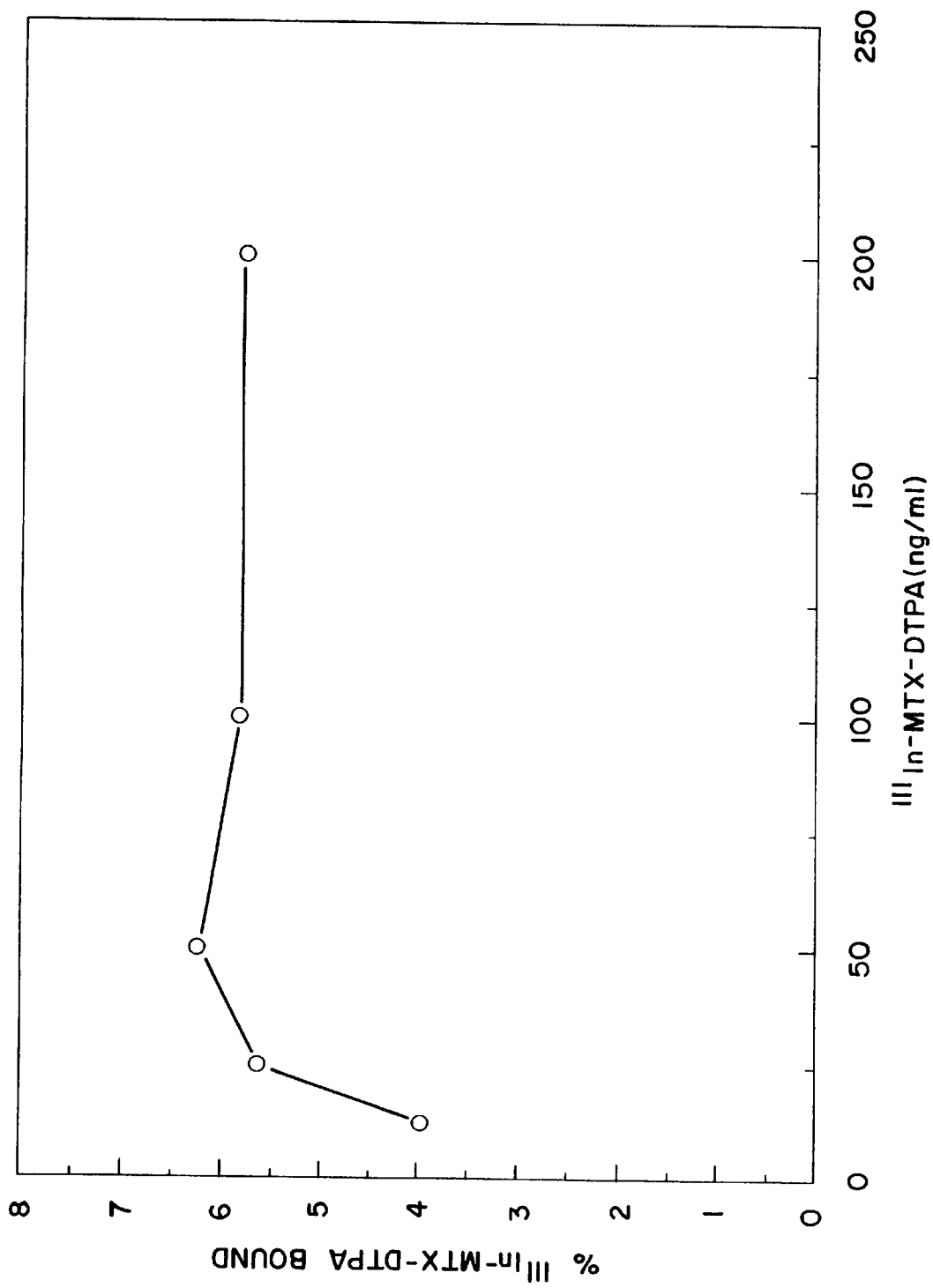

Referring to Example 9, results of the titration of the first study are shown in FIG. 51. Results of the second study are shown in FIG. 52.

DETAILED DESCRIPTION OF THE INVENTION

The present invention is directed to a non-radioactive targeting reagent that comprises a targeting moiety and the residues of one or more thermo-stabilized affinity components for non-covalent binding to an effector complex, represented by the following formula:

$$T\text{-}(L\text{-}A)_n$$

wherein:

T is a targeting moiety;

L is a chemical bond or a linking group that may contain one or more functional groups;

A is the residue of the thermo-stabilized affinity component; and n is an integer greater than zero.

The targeting moiety (T) may comprise a protein or peptide of known DNA or protein sequence capable of binding to cellular components at the targeting site. The thermo-stabilized affinity component is preferably a dihydrofolate reductase (DHFR), which may be obtained from any source, but is most preferably a human DHFR (including recombinant DHFR). The DHFR may also be mutant DHFR, i.e., naturally occurring mutants or intentional mutants made by molecular biological means known in the art, the only limitation being that it be functional as the affinity component in the targeting reagent.

Preferred methods for localizing radionuclides at an internal target site in a patient include two, three, four and five step procedures. The three, four and five step embodiments are refinements of the basic concept.

First, a non-toxic targeting moiety coupled to a non-toxic enzyme is administered parenterally to a patient and allowed to localize selectively at the target site. Non-localized circulating molecules of the targeting moiety-enzyme conjugate are allowed to clear from the circulatory system. If necessary, this clearing can be accelerated in vivo by complex formation or ex vivo by adsorption to a specific matrix using binding partners, such as antiidiotypic antibodies or antigens, (second step of the three-step procedure). Thereafter, a radionuclide-derivatized enzyme inhibitor or substrate, specific for the enzyme conjugated to the targeting moiety, is given parenterally. Binding of radiolabeled enzyme inhibitor or substrate to the localized enzyme-derivatized targeting moiety and rapid clearance of unbound radiolabeled enzyme inhibitor results in selective localization of the radionuclide at the target site.

Additional refinements include scavenging of unbound radionuclides using chelators as an additional step after administering the radionuclide conjugate. An additional step is also the administration of a blocking agent for enzyme inhibitor or substrate binding sites on cells, so the conjugate will only bind to the previously administered enzyme. Combinations of these procedures are contemplated within the invention.

The targeting moiety is typically an antibody reactive with a human tumor associated antigen. Particularly preferred for use in the invention are bivalent or multivalent human or chimeric monoclonal antibodies that bind with high avidity to tumor associated antigens located in an extracellular area (e.g. necrotic area) or on the cell surface and are not internalized upon binding to a cell surface antigen. The enzyme moiety preferred for use in the invention is of human origin or human-like, either by being genetically conserved or by being from a genetically similar species. An important requirement of the invention is that the enzyme used in the immunoconjugate must be essentially absent or present in only very low quantities in the circulation, extracellular areas, or on the cell surface of target organs to avoid blocking enzyme inhibitor or non-specific binding. In one embodiment, the enzyme is human dihydrofolate reductase, a single chain molecule of human origin that does not occur in extracellular fluids in measurable quantities. The third component of the targeting system is a radionuclide-derivatized enzyme inhibitor capable of binding with high affinity to the antibody-conjugated enzyme. Preferred for use in the invention are small molecular weight inhibitors that allow fast distribution through the body tissues and quick clearance by excretion of unbound inhibitor. The term enzyme inhibitor used in this invention encompasses molecules that bind to the enzyme and may augment, reduce, or leave unchanged enzymatic activity. Furthermore, the inhibitor molecule should be suitable for derivatization with radionuclides, e.g., by covalent attachment of a chelator molecule complexed with a radioactive metal, without impairing its affinity for the enzyme. In the preferred embodiment the radionuclide-derivatized enzyme inhibitor is a conjugate of methotrexate, a potent inhibitor of human dihydrofolate reductase, and diethylenetriamine-pentaacetic (DTPA) acid complexed with $^{111}$In or $^{90}$Y. Using the gamma-carboxyl residue of methotrexate for conjugation to the chelator, the affinity of the inhibitor to dihydrofolate reductase is not affected.

Those skilled in the art will recognize that the present invention is not limited to the targeting of radionuclides. A variety of diagnostic and therapeutic agents other than radionuclides may be attached to the enzyme inhibitor. Furthermore, two or more diagnostic or therapeutic agent residues may be attached to the inhibitor, for example via an oligomeric or polymeric carrier that is modified by one or more agent residues. oligomeric or polymeric carriers useful in this regard include natural and synthetic molecules such as polypeptides and oligosaccharides. Those skilled in the art will further recognize that the invention permits the introduction of additional residues to change the pharmacokinetic properties of the methotrexate-agent conjugates. For example, hydrophilic residues, such as sulfate or sulfonate groups, may be covalently attached to the conjugates to minimize non-specific binding to non-target proteins in serum or on cell surfaces, and to prevent cellular uptake in non-target tissues.

Another important requirement of the invention is that the system components must be non-immunogenic or poorly immunogenic. In the case of treating humans, the targeting moiety, e.g., an antibody, and the enzyme should be of human origin, humanized, or human-like, either by being genetically conserved or by being from a genetically similar species. Alternatively, components having masked immunogenic epitopes and, therefore, of poor immunogenicity may be used. Also, the radionuclide-derivatized enzyme inhibitor must be essentially non-immunogenic. The development of human antibodies against foreign proteins has been demonstrated in many studies. Human anti-mouse antibody formation in cancer patients has been reported after single injections of murine monoclonal antibodies. Human anti-mouse antibody (HAMA) formation occurs in up to 50% of cancer patients following single injections of murine monoclonal antibodies, (T. J. McCallister. S. E. Halpern, R. O. Dillman, D. L. Shawler, FASEB J. 2, 690, 1988), thereby limiting the applicability of these agents to a period of time required for the development of antibodies.

The targeting system described in this invention provides an affinity system that eliminates the serious limitations of currently available targeting techniques. Most importantly, all system components are high affinity components. The use of bivalent (e.g. IgG antibodies) or multivalent (e.g. IgA or IgM antibodies) agents as targeting moieties results in efficient natural clearance of non-bound antibody-enzyme conjugates over a period of several days without risk of complete dissociation of bound conjugates from the target sites. The use of enzyme inhibitors and the corresponding enzymes in an affinity system offers several advantages. First, some enzyme inhibitors are known to bind with extremely high affinities to the corresponding enzyme. For example, the overall binding constant of methotrexate to human dihydrofolate reductase ($K_{off}/K_{on}$:2.1×10$^{-10}$M) is rarely matched by the affinity of anti-hapten monoclonal antibodies. Second, enzyme:enzyme inhibitor systems offer the unique possibility of further increasing affinity by constructing multisubstrate analogue inhibitors (A. D. Broom, "Rational Design of Enzyme Inhibitors: Multisubstrate Analogue Inhibitors," J. Med. Chem. 32, 2–7, 1989). Recently, a multisubstrate adduct inhibitor of a purine biosynthetic enzyme (glycinamide ribonucleotide transformylase) with a picomolar dissociation constant has been synthesized (J. Inglese, R. A. Blatchly, S. J. Benkovic, J. Med. Chem. 32, 937–940, 1989). The inhibitor contains derivatives of the two substrates of the biomolecular, enzyme-catalyzed reaction, 10-formyl tetrahydrofolate and glycinamide ribonucleotide. The binding affinity of this multisubstrate inhibitor is approximately 3-fold higher than the product of the $K_m$ values of the two substrates, and $10^3$–$10^6$ times higher than the binding affinity of either substrate. In addition to multisubstrate inhibitors, suicide or mechanism-based inhibitors can be used. These inhibitors require interaction with the target enzyme in such a way as to initiate the catalytic process. As the reaction proceeds, a latent functional group, usually an electrophile, is unmasked within the active site. Alkylation or acylation of a suitably disposed active-site nucleophile inactivates the enzyme (R. B. Silverman, S. J. Hoffman, J. Med. Res. Rev. 4, 415, 1984). The advantage of suicide inhibitors is that upon binding of the inhibitor to the enzyme a covalent linkage between the two molecules is formed. As a result, radionuclide-derivatized inhibitor molecules bound to targeted antibody-enzyme conjugates cannot dissociate .

DESCRIPTION OF THE PREFERRED EMBODIMENTS

I. Choice of Antibody

Conventional polyclonal antibodies may be applied as carrier molecules within the concept of the invention. However, monoclonal antibodies offer multiple advantages. Each monoclonal antibody is specific for one antigenic determinant. Thus, with monoclonal antibodies the extent of non-specific binding to normal tissues and subsequent toxicity to normal non-target tissues is reduced. In addition, since unlimited amounts of each monoclonal antibody can be produced, all individual preparations of antibody can be controlled to ensure that antigen specificity remains constant over the life of the antibody product. Different monoclonal antibodies specific for different epitopes with the same tissue specifications may be combined. Thus, when using a monoclonal antibody or a mixture of monoclonal antibodies the efficacy and control of the delivery system is improved without sacrificing any contributions to the efficacy of the system that may be obtained with conventional polyclonal reagents.

A preferred approach is to use monoclonal or polyclonal antibodies of the same species of origin as the animal receiving therapy. It is not required that these antibodies be internalized by the target cell. For the most part, with the exception of veterinary applications, the use of human, humanized or chimeric antibodies that are primarily human in their construction, is most desirable. Many human monoclonal antibodies have been described. Also, approaches to humanizing antibodies developed from lymphoid cells of non-human species and methods using variable region genes from non-human antibodies genetically coupled to human antibody constant region genes have been described. The advantages of the homologous and genetically engineered antibodies are several. Unlike heterologous, e.g., murine or rat antibodies, the immune response to the homologous antibody is minimal. At most, a weak response to idiotypic determinants of the human antibody occurs and then only after multiple cycles of administration. In our clinical studies with human monoclonal antibodies we have not detected any induction of an immune response to any region of the antibody, idiotypic, allotypic or framework, even after repeated doses of up to 200 mg/week. This advantage allows use of intact whole immunoglobulin rather than more rapidly metabolized antibody fragments, allows high doses of intact whole immunoglobulin to be administered and allows the use of multiple cycles of antibody administration. In addition antibodies raised in homologous species have additional advantages, as they recognize subtle antigenic differences not recognized by heterologous antibodies or even genetically engineered human antibodies.

Antibody may be directed against any target, e.g., tumor, tissue, bacterial, fungal, viral, parasitic, mycoplasmal, histocompatibility or differentiation antigens or receptors. Antibody may be from any class, IgG, IgA, IgE or IgM, and a combination of antibodies reactive to different antigenic determinants may be used.

The targeting moiety need not be restricted to antibody but may be any substance that meets the basic requirements for a targeting moiety in this invention, as long as there is an affinity for the target tissue. Thus agents that bind specifically to certain tissue receptors such as hormones, lymphokines or certain classes of infectious agents may be used.

II. Construction of the Antibody-Enzyme Complex

Preparation of the immunoconjugate for our targeting system requires attachment of an enzymatic or affinity component (AC) to an antibody and forming a stable complex without compromising the activity of either component. Our strategy involves incorporation of a protected sulfhydryl onto the AC using the heterobifunctional crosslinker SPDP (n-succinimidyl-3-(2-pyridyldithio)propionate and then deprotecting the sulfhydryl for formation of a disulfide bond with another sulfhydryl on the antibody. Instead of destabilizing the antibody with reducing agents to generate free sulfhydryls, new sulfhydryls will also be incorporated onto the antibody using SPDP. In the protected form, the SPDP generated sulfhydryls on the antibody react with the free sulfhydryls incorporated onto the AC forming the required disulfide bonds. By optimizing reaction conditions, the degree of SPDP modification of each component can be controlled, thus allowing maximum incorporation of the AC onto the antibody while maintaining maximum activity of each component. SPDP reacts with primary amines and the incorporated sulfhydryl is protected by 2-pyridylthione.

If SPDP should affect the activities of either the antibody or the AC, there are a number of additional crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the protein. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

Other crosslinkers are available that can be used in different strategies for crosslinking our immunoconjugate components. TPCH(S-(2-thiopyridyl)-L-cysteine hydrazide and TPMPH ((S-(2-thiopyridyl)mercaptopropionohydrazide) react at the carbohydrate moieties of glycoproteins that have been previously oxidized by mild periodate treatment, thus forming a hydrazone bond between the hydrazide portion of the crosslinker and the periodate generated aldehydes. The placement of this crosslinker on the antibody is beneficial since the modification is site-specific and will not interfere with the antigen binding site of the antibody. TPCH and TPMPH introduce a 2-pyridylthione protected sulfhydryl group onto the antibody, which can be deprotected with DTT and then subsequently used for conjugation, such as forming disulfide bonds between components. If disulfide bonding is found unsuitable for producing stable conjugates, other crosslinkers may be used that incorporate more stable bonds between components.

The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives of some of the previously mentioned crosslinkers (i.e., SPDP). Thus there is an abundance of suitable crosslinkers, which could be used; each of which should be selected depending on the effects it has on optimal immunoconjugate production.

For our preferred embodiment, we have chosen the recombinant human enzyme dihydrofolate reductase (rhDHFR) as our affinity component and the anti-tumor IgM human monoclonal antibody 16.88 as the targeting component. Both components are modified with the SPDP derivative Sulfo-LC-SPDP by formation of a disulfide bond between the components. Sulfo-LC-SPDP is identical in its amino reactivity as SPDP but obtains a sulfo group on the succinimidyl group, conferring water solubility on the crosslinker, thus avoiding the use of organic solvents, which may have detrimental effects on the activities of both components. Also included on sulfo-LC-SPDP is a 5-carbon spacer, which reduces steric hinderance between the components. For our most preferred embodiment we first stabilize rhDHFR. This can be accomplished by covalent conjugation with ANPAP-NADP, as illustrated in Example 20. In one preferred embodiment, the tertiary structure of the affinity component, rhDHFR or mutants thereof, is thermostabilized by the introduction of intramolecular chemical crosslinks. Wild-type rhDHFR, the affinity component, is a single polypeptide of 186 amino acids without posttranslational modifications that contains a single sulfhydryl group (Cys 6), 17 internal amino groups (Lys 18, 46, 54, 55, 63, 68, 80, 98, 108, 122, 132, 155, 157, 173, 176, 178, and 184), and one terminal α-amino group (Masters, J. N., and Attardi, G., Gene 21: 59–63; 1983). These and other functional groups such as the carboxyl groups of glutamate and aspartate, the phenolic groups of tyrosine and phenylalanine, and the imidazole group of histidine can be used for modification of the affinity component by crosslinking reagents. If necessary, additional functional groups such as free sulfhydryl groups can be created i) by reaction with sulfhydryl-introducing reagents, or ii) by the introduction of cysteine residues via site-directed mutagenesis of the CDNA for rhDHFR. Such additional functional groups may serve as attachment sites for homo- and hetero-bifunctional crosslinking reagents.

A variety of reagents may be used to modify the affinity component with intramolecular chemical crosslinks (for reviews of crosslinking reagents and crosslinking procedures see: Wold, F., Meth. Enzymol. 25: 623–651, 1972; Weetall, H. H., and Cooney, D. A., In: Enzymes as Drugs. (J. S. Holcenberg, and J. Roberts, eds.) pp. 395–442, Wiley, New York, 1981; Ji, T. H., Meth. Enzymol. 91: 580–609, 1983; Mattson, G., Conklin, E., Desai, S., Nielander, G., Savage, M. D., and Morgensen, S., Mol. Biol. Rep. 17: 167–183, 1993, all of which are incorporated herein by reference). Preferred useful crosslinking reagents are derived from various zero-length, homobi-functional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example are reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar functional groups, respectively, which may be reactive for amino, sulfhydryl, guanidino, indole, or non-specific groups.

II. 1. Preferred Specific Functional Groups in Crosslinking Reagents

II. 1. 1. Amino-Reactive Groups

In one preferred embodiment, the functional groups are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of the affinity component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the affinity component. At a Ph between 7 and 10, imidoesters react only with primary amines. Primary amines attack imidates nucleophilically to produce an intermediate that breaks down to amidine at high Ph or to a new imidate at low Ph. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the affinity component.

Isocyanates (and isothiocyanates) react with the primary amines of the affinity component to form stable bonds. Their reactions with sulfhydryl, imidazole, and tyrosyl groups give relatively unstable products.

Acylazides may also be used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the affinity component, but also with its sulfhydryl and imidazole groups.

p-Nitrophenyl esters of mono- and dicarboxylic acids are also useful amino-reactive groups. Although the reagent specificity is not very high, α- and ï-amino groups appear to react most rapidly.

Aldehydes such as glutaraldehyde react with primary amines of the affinity component (e.g., ï-amino group of lysine residues). Glutaraldehyde, however, displays also reactivity with several other amino acid side chains including those of cysteine, histidine, and tyrosine. Since dilute glutaraldehyde solutions contain monomeric and a large number of polymeric forms (cyclic hemiacetal) of glutaraldehyde, the distance between two crosslinked groups within the affinity component varies. Although unstable Schiff bases are formed upon reaction of the protein amino groups with the aldehydes of the polymer, glutaraldehyde is capable of modifying the affinity component with stable crosslinks. At pH 6–8, the pH of typical crosslinking conditions, the cyclic polymers undergo a dehydration to form α–β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of functional groups of the affinity component, but reaction with the amino groups is the most important, resulting in a stable sulfonamide linkage.

II. 1.2. Sulfhydryl-Reactive Groups

In another preferred embodiment, the functional groups are sulfhydryl-reactive groups. Useful non-limiting examples of sulfhydryl-reactive groups include maleimides, alkyl halides, pyridyl disulfides, and thiophthalimides.

Maleimides react preferentially with the sulfhydryl group of the affinity component and those of multiple cysteine-containing mutants of the affinity component to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with the sulfhydryl group of the affinity component and those of multiple cysteine-containing mutants of the affinity component to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form also disulfides.

II. 1.3. Guanidino-Reactive Groups

In another embodiment, the functional groups are guanidino-reactive groups. A useful non-limiting example of a guanidino-reactive group is phenylglyoxal. Phenylglyoxal reacts primarily with the guanidino groups of arginine residues in the affinity component. Histidine and cysteine also react, but to a much lesser extent.

II. 1.4. Indole-Reactive Groups

In another embodiment, the functional groups are indole-reactive groups. Useful non-limiting examples of indole-reactive groups are sulfenyl halides. Sulfenyl halides react with tryptophan and cysteine, producing a thioester and a disulfide, respectively. To a minor extent, methionine may undergo oxidation in the presence of sulfenyl chloride.

II. 1.5. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage. Yamada, H., et al. (Biochemistry 20: 4836–4842, 1981) teach how to modify a protein with carbodiimde.

II.2. Preferred Nonspecific Functional Groups in Crosslinking Reagents

II. 2.1. Photoactivatable Groups

In a preferred embodiment, the functional groups are photoactivatable groups. Photoactivatable groups, completely inert in the dark, are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are preferable. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wave length. Unsubstituted arylazides have an absorption maximum in the range of 260–280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana, J. F. W., and Cai, S. X., J. Org. Chem. 55: 3640–3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

II. 2.2. Formaldehyde

In another embodiment, the non-specific reactive residue is formaldehyde. Formaldehyde offers a broad reaction specificity. In addition to amines, it reacts with the side chains of cysteine, tyrosine, histidine, tryptophan, anformginine. Although formaldehyde contains a single functional group, it can react bifunctionally and, thereby, act as a crosslinking reagent. Bifunctional reaction involves the attack of a nucleophile onto the aldehyde to form a quarternary ammonium salt, after which loss of water produces an ammonium cation. This cation is then attacked by another nucleophile producing a methylene-bridged crosslink.

Because of its lack of specificity, formaldehyde can crosslink the side chains of different amino acid residues (e.g. lysine and tyrosine) within the affinity component.

II. 3. Preferred Crosslinking Reagents

In addition to the foregoing description of preferred embodiments, particularly useful, non-limiting examples of crosslinking reagents for modification of the affinity component or mutants thereof are listed in the following sections.

II. 3.1. Homobifunctional Reagents

II. 3.1.1. Homobifunctional crosslinkers reactive with primary amines

Synthesis, properties, and applications of such reagents are described in the literature (for reviews of crosslinking procedures and reagents, see above). Some of the reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis[2-(succinimidooxycarbonyloxy) ethyl]sulfone (BSOCOES), bis[2-(sulfosuccinimidooxy-carbonyloxy)ethyl]sulfone (sulfo-BSOCOES), ethylene glycolbis(succinimidylsuccinate) (EGS), ethylene glycolbis(sulfosuccinimidylsuccinate) (sulfo-EGS), dithiobis (succinimidyl-propionate (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl3,3'-(dimethylenedioxy)dipropionimidate (DDDP), dimethyl-3,3'-(tetramethylenedioxy)dipropionimidate (DTDP), and dimethyl 3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

II. 3.1.2. Homobifunctional Crosslinkers Reactive with Free Sulfhydryl Groups

Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene) bismaleimide, azophenyldimaleimide, and bis(N-maleimidomethyl)ether.

Preferred, non-limiting examples of homobifunctional pyridyl disulfides include 1,4-di-[3'-(2'-pyridyldithio) propionamido]butane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl) phenylthydrazine, and 1,2-di(bromoacetyl)amino-3-phenylpropane.

II. 3.1.3. Homobifunctional Photoactivatable Crosslinkers

Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis[b-(4-azidosalicylamido)ethyl]disulfide (BASED), di-N-(2-nitro-4-azidophenyl)-cystamine-S,S-dioxide (DNCO), and 4,4'-dithiobisphenylazide.

II. 3.2. Hetero-Bifunctional Reagents

II. 3.2.1. Amino-Reactive Hetero-Bifunctional Reagents with a Pyridyl Disulfide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio)propionate (SPDP), succinimidyl 6-[3-(2-pyridyldithio)propionamido]hexanoate (LC-SPDP), sulfosuccinimidyl 6-[3-(2-pyridyldithio)propionamido] hexanoate (sulfo-LCSPDP), 4-succinimidyloxycarbonyl-a-methyl-a-(2-pyridyldithio)toluene (SMPT), and sulfosuccinimidyl 6-[a-methyl-a-(2-pyridyldithio)toluamido] hexanoate (sulfo-LC-SMPT).

II.3.2.2. Amino-Reactive Hetero-Bifunctional Reagents with a Maleimide Moiety

Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl- N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

II. 3.2.3. Amino-Reactive Hetero-Bifunctional Reagents with an Alkyl Halide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with an alkyl halide moiety and an amino-reactive NHS ester include N-succinimidyl-(4-iodoacetyl) aminobenzoate (SIAB), sulfosuccinimidyl-(4-iodoacetyl) aminobenzoate (sulfo-SIAB), succinimidyl-6-[(iodoacetyl) amino]hexanoate (SIAX), succinimidyl-6-(6-[((iodoacetyl)-amino)hexanoyl]amino)hexanoate (SIAXX), succinimidyl-6-[(((4-(iodoacetyl)-amino)-methyl)-cyclohexane-1-carbonyl)amino]hexanoate (SIACX), and succinimidyl-4 [((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety for primary amino groups is defined by the reaction temperature (McKenzie et al., Protein Chem. 7: 581–592, 1988).

Preferred, non-limiting examples of hetero-bifunctional reagents with an alkyl halide moiety and an amino-reactive p-nitrophenyl ester moiety include p-nitrophenyl iodoacetate (NPIA).

II. 3.2.4. Photoactivatable Arylazide-Containing Hetero-Bifunctional Reagents with an NHS Ester Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable arylazide-containing hetero-bifunctional reagents with an amino-reactive NHS ester include N-hydroxysuccinimidyl-4-azidosalicylic acid (NHS-ASA), N-hydroxysulfosuccinimidyl-4-azidosalicylic acid (sulfo-NHS-ASA), sulfosuccinimidyl-(4-azidosalicylamido)hexanoate (sulfo-NHS-LC-ASA), N-hydroxysuccinimidyl N-(4-azidosalicyl)-6-aminocaproic acid (NHS-ASC), N-hydroxysuccinimidyl-4-azidobenzoate (HSAB), N-hydroxysulfosuccinimidyl-4-azidobenzoate (sulfo-HSAB), sulfosuccinimidyl-4-(p-azidophenyl)butyrate (sulfo-SAPB), N-5-azido-2-nitrobenzoyloxy-succinimide (ANB-NOS), N-succinimidyl-6-(4'-azido-2'-nitrophenyl-amino) hexanoate (SANPAH), sulfosuccinimidyl-6-(4'-azido-2'-nitrophenylamino)-hexanoate (sulfo-SANPAH), N-succinimidyl 2-[(4-azidophenyl)dithio]acetic acid (NHS-APDA), N-succinimidyl-(4-azidophenyl)1,3'-dithiopropionate (SADP), sulfosuccinimidyl-(4-azidophenyl)-1,3'-dithiopropionate (sulfo-SADP), sulfosuccinimidyl-2-(m-azido-o-nitrobenzamido)ethyl-1,3'-dithiopropionate (SAND), sulfosuccinimidyl-2-(p-azidosalicylamido)-ethyl-1,3'-dithiopropionate (SASD), N-hydroxysuccinimidyl 4-azidobenzoylglycyltyrosine (NHS-ABGT), sulfosuccinimidyl-2-(7-azido-4-4-methylcoumarin-3-acetamide)ethyl-1,3'-dithiopropionate (SAED), and sulfosuccinimidyl-7-azido-4-methylcoumarin-3-acetate (sulfo-SAMCA).

II. 3.2.5. Photoactivatable Arylazide-Containing Hetero-Bifunctional Reagents with an Imidate Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable aryl azide-containing hetero-bifunctional reagents with an amino-reactive imidate moiety include methyl-4-azidobenzimidate, methyl-3-[(4-azidophenyl)-dithio] propionimidate (MADP), methyl-4-[(4-azidophenyl)-dithio] butyrimidate (MADB), and ethyl-4-azidophenyl-1,4'-dithiobutyrimidate (EADB).

II. 3.2.6. Photoactivatable Acrylazide-Containing Hetero-Bifunctional Reagents with an Isothiocyanate Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with an amino-reactive isothiocyanate moiety include 5-azido-1-naphthyl isothiocyanate ($N_3$NAPNCS).

II. 3.2.7. Photoactivatable Acrylazide-Containing Hetero-Bifunctional Reagents with an Arylhalide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with an amino-reactive arylhalide moiety include 4-fluoro-3-nitrophenyl-azide (FNPA).

II. 3.2.8. Photoactivatable Acrylazide-Containing Hetero-Bifunctional Reagents with a Pyridyl Disulfide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with a pyridyl disulfide moiety include N-[4-(p-azidosalicylamido)-butyl]-3'-(2'-pyridyldithio) propionamide (APDP).

II. 3.2.9. Photoactivatable Acrylazide-Containing Hetero-Bifunctional Reagents with an Alkyl Halide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with an alkyl halide moiety include 1-(p-azidosalicylamido)-4-(iodoacetamido) butane (ASIB), p-azidophenylacyl bromide, and 4-(bromoaminoethyl)-2-nitrophenylazide (BANPA).

II. 3.2.10. Photoactivatable Acrylazide-Containing Hetero-Bifunctional Reagents with a Thiophthalimide Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with a thiophthalimide moiety include N-(4-azidophenylthio)-phthalimide (APTP).

II. 3.2.11. Photoactivatable Acrylazide-Containing Hetero-Bifunctional Reagents with a Sulfenyl Chloride Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with a sulfenyl chloride moiety include 4-azidophenylsulfenyl chloride, and 2-nitro-4-azidophenylsulfenyl chloride.

II. 3.2.12. Photoactivatable Arylazide-Containing Hetero-Bifunctional Reagents with a Glyoxal Moiety Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of photoactivatable acrylazide-containing hetero-bifunctional reagents with a glyoxal moiety include 4-azidoglyoxal.

II. 3.2.13. Photoactivatable Perfluorinated Arylazide-Containing Hetero-Bifunctional Reagents Synthesis, properties, and applications of such reagents are described in the literature (Crocker, P. J., et al., Bioconjgate Chem. 1: 419–424, 1990). Some of the reagents are commercially available (e.g., Molecular Probes, Inc., Eugene, Oreg.).

Preferred, non-limiting examples of hetero-bifunctional reagents with a photoactivatable perfluorinated acrylazide moiety and an amino-reactive NHS ester moiety include succinimidyl N-4-azido-2,3,5,6,-tetrafluorobenzoate, succinimidyl N-(4-azido-2,3,5,6,-tetrafluorobenzoyl)tyrosinate, and succinimidyl 2-(4-azido-2,3,5,6,-tetra-fluorophenyl) thiazole-4-carboxylate.

II. 3.2.14. Photoactivatable Diazo-Containing Hetero-Bifunctional Reagents

Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a diazo moiety include the amino-reactive reagent p-nitrophenyl-2-diazo-3,3,3-trifluoropropionate (PNP-DTP).

II. 3.2.15. Photoactivatable Benzophenone-Containing Hetero-Bifunctional Reagents.

Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of benzophenone-containing hetero-bifunctional reagents with an amino-reactive moiety include succinimidyl 4-benzoylbenzoic acid, and benzophenone-4-isothiocyanate.

Preferred, non-limiting examples of benzophenone-containing hetero-bifunctional reagents with a sulfhydryl-reactive moiety include benzophenone-4-iodoacetamide, and benzophenone-4-maleimide.

II. 3.2.16. Photoactivatable Diazopyruvate-Containing Hetero-Bifunctional Reagent Synthesis, properties, and applications of such reagents are described in the literature (for reviews of crosslinking procedures and reagents see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a diazopyruvate moiety include the amino-reactive reagent: p-nitrophenyl 3-diazopyruvate.

II. 4. Preferred Sulfhydryl-Introducing Reagents

In a preferred embodiment, the affinity component is modified by addition of free sulfhydryl groups to provide additional attachment sites for homobifunctional sulfhydryl-reactive crosslinking agents or hetero-bifunctional crosslinking reagents with a sulfhydryl-reactive moiety.

II. 4.1. Single Step Thiolation

In one preferred embodiment, the affinity component is modified by addition of free sulfhydryl groups by a single step procedure using amino-reactive reagents such as 3-mercaptopropionimidate hydrochloride, 2-iminothiolane hydrochloride, and N-acetylhomocysteine lactone.

Perham, R. N., and Thomas, J. O. (J. Mol. Biol. 62: 415–418; 1971) teach how to introduce free sulfhydryl groups into the amine-containing affinity component by reaction with 3-mercaptopropionimidate hydrochloride. Jue, R., Lambert, et al. (Biochemistry 17: 1499–1506; 1978) teach how to introduce free sulfhydryl groups into the amine-containing affinity component by reaction with 2-iminothiolane hydrochloride. Renesch, R., and Benesch, R. E. (J. Am. Chem. Soc. 78: 1597–1599; 1956) teach how to introduce free sulfhydryl groups into the amine-containing affinity component by reaction with N-acetylhomocysteine lactone.

II. 4.2. Thiolation with Thioester-Containing Reagents

In another preferred embodiment, thiolation of the affinity component is performed by reaction with thioester-containing reagents such as N-succinimidyl-S-acetylthioacetate (SATA), and S-acetylmercaptosuccinic anhydride. Thioesters are extremely sensitive to attack by nitrogen nucleophiles. For example, free sulfhydryls are easily generated from the introduced thioesters by mild treatment with an aqueous hydroxylamine solution at neutral pH. Duncan, R. J. S., et al. (Anal. Biochem. 132: 68–73; 1983) teach how to introduce thiol ester groups into the amine-containing affinity component by reaction with SATA. Klotz, I. M., and Heiney, R. E. (Arch. Biochem. Biophys. 96: 605–612; 1962) teach how to introduce thiol ester groups into the amine-containing affinity component by reaction with S-acetylmercaptosuccinic anhydride.

II. 4.3. Thiolation with Activated Disulfide-Containing Reagents

In another preferred embodiment, the affinity component is derivatized with activated disulfide groups which are subsequently reduced to generate free sulfhydryl groups. Preferred reagents are amino-reactive hetero-bifunctional reagents containing activated disulfide groups such as pyridyl disulfide moieties and S-sulfonate groups. Carlsson, J., et al., (Biochem. J. 173: 723–737; 1978) teach how to derivatize the amine-containing affinity component with 2-pyridyldisulfide groups by reaction with N-succinimidyl-3-(2-pyridyldithio)propionate (SPDP). Subsequent treatment of the derivatized affinity component with a reducing agent such as mercaptoethanol or dithiothreitol generates free sulfhydryl groups. King, T. P., Li, Y., and Kochoumian, L. (Biochemistry 17: 1499–1506; 1978) teach how to derivatize the amine-containing affinity component with 4-pyridyldisulfide groups by reaction with methyl-3-(4-pyridyldithio)mercaptopropionimidate hydrochloride. Subsequent treatment of the derivatized affinity component with a reducing agent such as mercaptoethanol or dithiothreitol generates free sulfhydryl groups. Thorpe, P. E., et al. (Cancer Res. 47: 5924–5931; 1987) teach how to introduce S-sulfonate groups into the amine-containing affinity component by reaction with sodium S-4-succinimidyl-oxycarbonyl-a-methyl benzyl thiosulfate (SMBT). Subsequent treatment of the derivatized affinity component with a reducing agent such as mercaptoethanol or dithiothreitol generates free sulfhydryl groups.

III. Stabilization of the Affinity Component by Noncovalent Binding of NADP(H)-Derived Ligands In another preferred embodiment, the tertiary structure of the enzymatic (or affinity) component (AC), rhDHFR or rhDHFR derivatives, is thermo-stabilized by noncovalent binding of NADP(H)-derived ligands. Both NADP and NADPH are capable of protecting wild-type recombinant human dihydrofolate reductase (rhDHFR) from thermal denaturation (Prendergast, N. J., et al., Biochemistry 27: 3664–3671, 1988). One aspect of the present invention is directed to NADP(H)-derived ligands which are useful for providing thermal stability to the affinity component when non-covalently bound. Particularly useful, non-limiting examples of ligands are listed in the following sections.

III. 1. NADP(H) Derivatives

In one preferred embodiment, NADP(H) ($\beta$ and $\alpha$ analogues) and NADP(H) derivatives ($\beta$ and $\alpha$ analogues) are used for thermo-stabilization of the affinity component.

III. 1.1. Adenine-C8 Derivatives of NADP(H)

In one preferred embodiment of NADP(H) derivatives, adenine-C8 derivatives of NADP(H) ($\beta$ and $\alpha$ analogues) are used. Lee, C.-Y., and Kaplan, N. O. (Arch. Biochem. Biophys. 168: 665–676, 1975) teach how to synthesize 8-bromo and 8-(6-aminohexyl)amino derivatives of NADP. Zapelli, P., Rossodivita, et al. (Eur. J. Biochem. 62: 211–215, 1976) teach how to synthesize 8-(2-carboxyethylthio) and 8-polyethyleneimine-2-carbonylethylthio derivatives of NADP. Holmes, R. E., and Robins, R. K. (J. Am. Chem. Soc. 87: 1772–1776, 1964) teach how to convert an 8-bromo adenosine moiety to an 8-hydrazino-adenosine moiety, 8-azido-adenosine moiety, and 8-amino-adenosine moiety. The synthesis of additional preferred adenine-C8 derivatives, 8-(2-aminoethyl)-amino-NADP and 8-(p-azidosalicylamido-ethyl)amino-NADP, is described in Example 12. Preferred, non-limiting examples of adenine-C8 derivatives of NADP(H) include nicotinamide 8-bromoadenine dinucleotide phosphate (8-Br-NADP), nicotinamide 8-(6-aminohexyl)amino-adenine dinucleotide phosphate; (8-(6-aminohexyl)amino-NADP); nicotinamide 8-(2-carboxyethylthio)-adenine dinucleotide phosphate; (8-(2-carboxyethylthio)-NADP); nicotinamide 8-(polyethyleneimine-2-carbonylethylthio)-adenine dinucleotide; phosphate (8-polyethyleneimine-2-carbonylethylthio)-NADP); nicotinamide 8-hydra-zinoadenine dinucleotide phosphate, (8-hydrazino-NADP); nicotinamide 8-azidoadenine dinucleotide phosphate (8-$N_3$-NADP); nicotinamide 8-aminoadenine dinucleotide phosphate (8-$NH_2$-NADP); nicotinamide 8-(2-aminoethyl) amino-adenine dinucleotide phosphate; (8-(2-aminoethyl)amino-NADP); nicotinamide 8-(p-azidosalicylamidoethyl)amino-adenine dinucleotide; phosphate (8-(p-azidosalicylamidoethyl) amino-NADP).

III. 1.2. Adenine-N6 Derivatives of NADP(H)

In another preferred embodiment of NADP(H) derivatives, adenine-N6 derivatives of NADP(H) ($\beta$ and $\alpha$ analogues) are used. Mosbach, K., et al. (Meth. Enzymol. 44: 859–887, 1976) teach how to synthesize $N^6$-carboxymethyl-NADP and $N^6$-[(6-aminohexyl) carbamoylmethyl]-NADP. Harvey, M. J., et al. (Meth. Enzymol. 34: 242–253, 1974) teach how to derivatize the adenine moiety at the N6-position with 1,6-hexanediamine. Okuda, K., et al. (Eur. J. Biochem. 147:241:247, 1985) teach how to synthesize $N^6$-(2-carboxyethyl)-NADP and $N^6$-[N-(2-aminoethyl)-carbamoylethyl]-NADP. Preferred, non-limiting examples of adenine-N6 derivatives of NADP(H) include nicotinamide $N^6$-carboxy-methyl-adenine dinucleotide phosphate, ($N^6$-carboxymethyl-NADP); nicotinamide $N^6$-[(6-aminohexyl) carbamoylmethyl]-adenine dinucleotide; phosphate, ($N^6$-[(6-aminohexyl)-carbamoylmethyl]-NADP); nicotinamide $N^6$-(6-aminohexyl)-adenine dinucleotide phosphate, ($N^6$-(6-aminohexyl)-NADP); nicotinamide $N^6$-(2-carboxyethyl)-adenine dinucleotide phosphate, ($N^6$-(2-carboxyethyl)-NADP); nicotinamide $N^6$-[N-(2-aminoethyl)-carbamoylethyl]-adenine dinucleotide phosphate, ($N^6$-[N-(2-aminoethyl)carbamoylethyl]-NADP); and 1, $N^6$-ethenonicotinamide adenine dinucleotide phosphate, (1,$N^6$-etheno-NADP).

III. 1.3. Deamino (Hypoxanthine) Derivatives of NADP(H)

In another preferred embodiment of NADP(H) derivatives, deamino derivatives of NADP(H) ($\beta$ and $\alpha$ analogues) are used. Preferred, non-limiting examples include nicotinamide hypoxanthine dinucleotide phosphate.

III. 1.4. Phosphate Derivatives of NADP(H)

In another preferred embodiment of NADP(H) derivatives, phosphate derivatives of NADP(H) ($\beta$ and $\alpha$ analogues) are used. In one preferred embodiment of phosphate derivatives of NADP, analogues with thiophosphate groups are used. Preferred, non-limiting examples of thiophosphate derivatives include adenosine 2'-phospho 5'-[$\alpha$-thio]diphospho 5'-ribofuranosyl-nicotinamide, (NADP[$\alpha$-S]); and adenosine 2'-thiophospho 5'-[$\alpha$-thio]diphospho 5'-ribofuranosyl-nicotinamide, (NADP[2'-S, $\alpha$-S]).

In another preferred embodiment of phosphate derivatives of NADP(H), analogues containing the monophosphate group at a different position are used. Preferred, non-limiting examples of such NADP(H) derivatives include nicotinamide adenine dinucleotide 3'-phosphate.

In another preferred embodiment of phosphate derivatives of NADP(H), analogues containing a cyclic monophosphate group are used. Sogin, D. C. (J. Neurochem. 27:1333–1337, 1976) teaches how to synthesize NADP(H) derivatives containing a cyclic phosphate group. Preferred, non-limiting examples of such NADP(H) derivatives include nicotinamide adenine dinucleotide 2':3'-cyclic monophosphate, (2':3'-cyclic NADP).

In another preferred embodiment of phosphate derivatives of NADP(H), analogues containing a modified 2'-monophosphate group are used. Okuda, K., et al. (Eur. J. Biochem. 147:241:247, 1985) teach how to synthesize NADP(H) derivatives containing modified 2'-monophosphate groups. Preferred, non-limiting examples of NADP(H) derivatives containing modified 2'-monophosphate groups include 2'-O-(2-carboxyethyl) phosphono-NADP, and 2'-O-[N-(2-aminoethyl) carbamoylethyl]phosphono-NADP.

III. 1.5. Nicotinamide Ribose Derivatives of NADP(H)

In another preferred embodiment of NADP(H) derivatives, nicotinamide ribose derivatives of NADP(H) (β and α analogues) are used. In one preferred embodiment of nicotinamide ribose derivatives of NADP(H), analogues with a modified N3'-position are used. Chen, S., and Guillory, R. J. (J. Biol. Chem. 255: 2445–2453, 1980) teach how to synthesize NADP(H) derivatives containing an arylazido-β-alanyl moiety at the N3'-position of the nicotinamide ribose moiety. The synthesis of additional NADP(H) analogues with a modified N3'-position is described in Example 14. Preferred, non-limiting examples include N3'-O-[3-(N-(4-azido-2-nitrophenyl)amino)propionyl]-NADP (arylazido-β-alanyl NADP; ANPAP-NADP); N3'-O-(3-(3-(N-(4-azido-2-nitrophenyl)-amino)propionyl)aminopropionyl]NADP, (arylazido-β-alanyl-β-alanyl-NADP); N3'-O-[2-(N-(4-azido2-nitrophenyl)amino)-3-(2-pyridyldithio)propionyl]-NADP, (arylazido-(S-thiopyridyl)cysteinyl-NADP); N3'-O-[3-(2-(N-(azido-2-nitrophenyl)amino)-3-(2-pyridyldithio)propionyl)-aminopropionyl]-NADP, (arylazido-(S-thiopyridyl)-cysteinyl-b-alanyl-NADP); and N3'-O-[3-(N-tert.-butoxycarbonylamino)propionyl)-NADP (BOC-β-alanyl-NADP).

In another preferred embodiment of nicotinamide ribose derivatives of NADP(H), analogues containing an N2',N3'-dialdehyde are used. Erlanger, B. F., and Beiser, S. M. (Proc. Natl. Acad. Sci. U.S.A. 52: 68–74, 1964) teach how to convert ribose containing nucleotides by periodate treatment to 2',3'-dialdehyde containing analogues. Preferred, non-limiting examples of NADP(H) derivatives containing dialdehyde functions include nicotinamide adenine dinucleotide phosphate N2',N3'-dialdehyde.

In another preferred embodiment of nicotinamide ribose derivatives of NADP(H), analogues derived from N2',N3'-dialdehyde-containing NADP(H) derivatives are used. The synthesis of such derivatives is described in Example 14. Preferred, non-limiting examples of NADP(H) analogues derived from N2',N3'-dialdehyde-containing NADP(H) derivatives include NADP-N2',N3'-dial-[3-(N-(4-azido-2-nitrophenyl)amino)propionic acid hydrazone], (arylazido-β-alanyl-morpholino NADP); NADP-N2',N3'-dial-[3-(3-(N-(4-azido-2-nitrophenyl)amino)propionyl) amino-propionic acid hydrazone], (arylazido-β-alanyl-β-alanyl-morpholino NADP); NADP-N2',N3'-dial-(4-azido2,3,5,6,-tetrafluorobenzoic acid hydrazone), (perfluorinated arylazido-morpholino NADP); and NADP-N2',N3'-dial-[3-(N-(4azido-2,3,5,6,-tetrafluorobenzoyl)amino)propionic acid hydrazone], (perfluorinated arylazido-β-alanyl-morpholino NADP).

III. 1.6. Nicotinamide Derivatives of NADP

In another preferred embodiment of NADP(H) derivatives, oxidized and reduced nicotinamide derivatives of NADP(H) (β and α analogues) are used. A review of Guillory, R. J., et al. (Annals N.Y. Acad. Sci. 346: 244–279, 1980) teaches how to synthesize nicotinamide derivatives of NADP. Preferred, non-limiting examples of nicotinamide derivatives of NADP(H) include 3-diazoacetoxymethyl-pyridine adenine dinucleotide phosphate, and 3-azido-pyridine adenine dinucleotide phosphate.

III.1.7. NADP(H) Derivatives Containing More Than One Modification

In another preferred embodiment of NADP(H) derivatives, oxidized and reduced derivatives of NADP(H) (β and α analogues) are used that contain a combination of the modifications listed above (sections III.1.1.–III.1.6.).

Preferred, non-limiting examples of NADP(H) derivatives with two modifications include NADP(H) analogues containing an adenine C8-azido group and an arylazido-β-alanyl group at the nicotinamide ribose moiety.

Preferred, non-limiting examples of NADP(H) derivatives with three modifications include NADP(H) analogues containing an adenine C8-azido group, thiophosphate groups and an arylazido-β-alanyl group at the nicotinamide ribose moiety.

Preferred, non-limiting examples of NADP(H) derivatives with four modifications include NADP(H) analogues containing an adenine C8-azido group, thiophosphate groups,. an arylazido-β-alanyl group at the nicotinamide ribose moiety, and a 3-diazoacetoxymethylpyridine moiety instead of nicotinamide.

III.2. Adenosine 2'-Monophospho-5'-Diphosphoribose and Derivatives

In another preferred embodiment, adenosine 2'-monophospho-5'-diphosphoribose (phospho-ADPR) and phospho-ADPR derivatives are used for thermo-stabilization of the affinity component.

Preferred examples of adenosine 2'-monophospho-5'-diphosphoribose (phospho-ADPR) analogues are derived from NADP analogues containing a modified adenine C8 position (III.1.1.), a modified adenine N6 position (III.1.2.), a deamino-adenine (hypoxanthine) moiety (III.1.3.), modified phosphate residues (III.1.4.), or a modified nicotinamide ribose moiety (III.1.5.). Kaplan, N. O. (Meth. Enzymol. 2: 664–668, 1955) teaches how to prepare phospho-ADPR and phospho-ADPR derivatives by treatment of NADP and corresponding NADP derivatives with Neurospora crassa NADase (NAD glycohydrolase).

III. 3. NAD(H) and Derivatives

In another preferred embodiment, NAD(H) and NAD(H) derivatives are used for thermo-stabilization of the affinity component.

III. 3.1. Adenine-C2 Derivatives of NAD(H)

In one preferred embodiment of NAD(H) derivatives, oxidized and reduced adenine-C2 derivatives of NAD(H) (β and α analogues) are used. Kim, H., and Haley, B. E. (J. Biol. Chem. 265: 3636–3641, 1990) teach how to synthesize 2-azido-NAD. Preferred, non-limiting examples of adenine-C2 derivatives of NAD(H) include nicotinamide 2-azido-adenine dinucleotide (2-$N_3$-NAD).

III.3.2. Adenine-C8 Derivatives of NAD(H)

In another preferred embodiment of NAD(H) derivatives, oxidized and reduced adenine-C8 derivatives of NAD(H) (β and α analogues) are used. Lee, C.-Y., and Kaplan, N. O. (Arch. Biochem. Biophys. 168: 665–676, 1975) teach how to synthesize the 8-bromo and 8-(6-aminohexyl)amino derivatives of NAD. Zapelli, P., et al. (Eur. J. Biochem. 62: 211–215, 1976) teach how to synthesize the 8-(2-carboxyethylthio) and 8-poly-ethyleneimine-2-carbonylethylthio derivatives of NAD. Holmes, R. E., and Robins, R. K. (J. Am. Chem. Soc. 87: 1772–1776, 1964) teach how to convert an 8-bromo adenosine moiety to an 8-hydrazino-adenosine moiety, 8-azido-adenosine moiety, or 8-amino-adenosine moiety. Preferred, non-limiting examples of adenine-C8 derivatives of NAD(H) include those listed in section III.1.1. in which the NAD(H) moiety is replaced by an NADP(H) moiety.

III. 3.3. Adenine-N6 Derivatives of NAD(H)

In another preferred embodiment of NAD(H) derivatives, oxidized and reduced adenine-N6 derivatives of NAD(H) (β and α analogues) are used. Mosbach, K., et al. (Meth. Enzymol. 44: 859–887, 1976) teach how to synthesize $N^6$-carboxymethyl-NAD and $N^6$-[(6-aminohexyl)carbamoylmethyl]-NAD. Harvey, M. J., et al. (Meth. Enzymol. 34: 242–253, 1974) teach how to derivatize the adenine moiety at the N6-position with 1,6-hexanediamine. Okuda, K., et al. (Eur. J. Biochem. 147:241:247, 1985) teach how to synthesize $N^6$-(2-carboxy-ethyl)-NAD and $N^6$-[N-(2-aminoethyl)-carbamoylethyl]-NAD. Preferred, non-limiting examples of adenine-N6 derivatives of NAD(H) include those listed in section III.1.2. in which the NAD(H) moiety is replaced by an NADP(H) moiety.

III. 3.4. Deamino (Hypoxanthine) Derivatives of NAD(H)

In another preferred embodiment of NAD(H) derivatives, oxidized and reduced deamino derivatives of NAD(H) ($\beta$ and $\alpha$ analogues) are used. Preferred, non-limiting examples include nicotinamide hypoxanthine dinucleotide.

III.3.5. Adenine Ribose Derivatives of NAD(H)

In another preferred embodiment of NAD(H) derivatives, oxidized and reduced adenine ribose derivatives of NADP (H) ($\beta$ and $\alpha$ analogues) are used. A review of Guillory, R. J., et al. (Annals N.Y. Acad. Sci. 346: 244–279, 1980) teaches how to synthesize the arylazido-$\beta$-alanyl derivative of NAD. Preferred, non-limiting examples include A3'-O-[3-(N-(4-azido-2-nitrophenyl)amino)propionyl]-NAD, (arylazido-$\beta$-alanyl NAD; ANPAP-NAD).

III.3.6. Phosphate Derivatives of NAD(H)

In another preferred embodiment of phosphate derivatives of NAD(H), analogues with thiophosphate groups are used. Meyer, T., et al. (Eur. J. Biochem. 140: 531–537, 1984) teach how to synthesize thiophosphate derivatives of NAD(H). Preferred, non-limiting examples of NAD(H) derivatives containing thiophosphate groups include adenosine (5') [a-thio]diphospho (5')ribofuranosyl-nicotinamide (NAD [S]).

III. 3.7. Nicotinamide Derivatives of NAD

In another preferred embodiment of NAD(H) derivatives, oxidized and reduced nicotinamide derivatives of NAD(H) ($\beta$ and $\alpha$ analogues) are used. A review of Guillory, R. J., Jeng, et al. (Annals N.Y. Acad. Sci. 346: 244–279, 1980) teaches how to synthesize the 3-diazoacetoxymethyl-pyridine and 3-azido-pyridine derivatives of NAD. Preferred, non-limiting examples of nicotinamide derivatives of NAD include 3-diazoacetoxymethyl-pyridine adenine dinucleotide; 3-azido-pyridine adenine dinucleotide; nicotinic acid adenine dinucleotide (deamido NAD).

III.4. Adenosine 5'-Diphosphoribose and Derivatives

In another preferred embodiment, adenosine 5'-diphosphoribose (ADPR) and ADPR derivatives are used for thermo-stabilization of the affinity component.

Preferred examples of adenosine 5'-diphosphoribose (ADPR) analogues are derived from NAD analogues containing a modified adenine C2 position (III.3.1.), a modified adenine-C8 position (III.3.2.), a modified adenine N6 position (III.3.3.), a deamino-adenine (hypoxanthine) moiety (III.3.4.), a modified adenine ribose moiety (III.3.5.), or modified phosphate groups (III.3.6.). Kaplan, N. O. (Meth. Enzymol. 2: 664–668, 1955) teaches how to prepare additional preferred ADPR derivatives are comprised of molecules in which the reducing ribose moiety is replaced by another carbohydrate moiety. Preferred examples of such ADPR derivatives include Adenosine 5-diphosphomannose; and Adenosine 5'-diphosphoglucose.

III. 5. Adenosine Triphosphates and Derivatives

In another preferred embodiment, adenosine triphosphates (including adenosine 5'-triphosphate (5'-ATP), adenosine 3'-monophosphate-5'-diphosphate, and adenosine 2'-monophosphate-5'-diphosphate) and derivatives of adenosine triphosphates are used for thermo-stabilization of the affinity component.

III. 5.1. Adenine-C2 Derivatives of Adenisine Triphosphates

In one preferred embodiment of adenosine triphosphate derivatives, adenine-C2 derivatives of adenosine triphosphates are used. Kim, H., and Haley, B. E. (J. Biol. Chem. 265: 3636–3641, 1990) teach how to synthesize 2-azido-5'-AMP, from which 2-azido-5'-ATP is synthesized according to standard procedures. Preferred, non-limiting examples of adenine-C2 derivatives of adenosine triphosphates include 2-azido-adenosine 5'-triphosphate.

III. 5.2. Adenine-C8 Derivatives of Adenosine Triphosphates

In another preferred embodiment of adenosine triphosphate derivatives, adenine-C8 derivatives of adenosine triphosphates are used. Lee, C.-Y., and Kaplan, N. O. (Arch. Biochem. Biophys. 168: 665–676, 1975) teach how to synthesize the 8-bromo, 8-(6-aminohexyl)amino, and p-8-diazo derivatives of adenosine triphosphates. Zapelli, P., et al. (Eur. J. Biochem. 62: 211–215, 1976) teach how to synthesize the 8-(2-carboxyethylthio) and 8-polyethyleneimine-2-carbonylethylthio derivatives of adenosine triphosphaces. Holmes, R. E., and Robins, R. K. (J. Am. Chem. Soc. 87: 1772–1776, 1964) teach how to convert an 8-bromo adenosine moiety to an 8-hydrazino-adenosine moiety, 8-azido-adenosine moiety, or 8-amino-adenosine moiety. Preferred, non-limiting examples of adenine-C8 derivatives of adenosine triphosphates include those listed in section III.1.1. in which the adenosine triphosphate moiety is replaced by an NADP(H) moiety.

III. 5.3. Adenine-N6 Derivatives of Adenosine Triphosphates

In another preferred embodiment of adenosine triphosphate derivatives, adenine-N6 derivatives of adenosine triphosphates are used. Mosbach, K., et al. (Meth. Enzymol. 44: 859–887, 1976) teach how to synthesize $N^6$-carboxymethyl-adenosine triphosphates and $N^6$-[(6-aminohexyl)carbamoylmethyl]-adenosine triphosphates. Harvey, M. J., et al. (Meth. Enzymol. 34: 242–253, 1974) teach how to derivatize the adenine moiety at the N6-position with 1,6-hexanediamine. Okuda, K., et al. (Eur. J. Biochem. 147:241:247, 1985) teach how to synthesize $N^6$-(2-carboxyethyl)-adenosine triphosphates and $N^6$-[N-(2-aminoethyl)-carbamoylethyl]-adenosine triphosphates. Preferred, non-limiting examples of adenine-N6 derivatives of adenosine triphosphates include those listed in section III.1.2. in which the adenosine triphosphate moiety is replaced by an NADP(H) moiety.

III. 5.4. Ribose Derivatives of Adenosine Triphosphates

In another preferred embodiment of adenosine triphosphate derivatives, ribose derivatives of adenosine triphosphates (including deoxy nucleotide analogues) are used. In one preferred embodiment of ribose derivatives of adenosine triphosphate, derivatives with a modified 3'-position are used. Jeng, S. J., and Guillory, R. J. (J. Supramol. Structure 3: 448–468, 1975) teach how to synthesize derivatives of adenosine triphosphates modified at the 3'-position with an arylazido group via different spacer molecules. Colman, R. F., et al. (Meth. Enzymol. 46: 240–249, 1977) teach how to synthesize derivatives of adenosine triphosphates modified at the 3'-position with a fluorosulfonylbenzoyl moiety. Preferred, non-limiting examples include 3'-O-[3-(N-(4-azido-2-nitrophenyl)-amino)propionyl]-5'-ATP (ANPAP-5'-ATP); 3'-O-[4-(N-(4-azido-2-nitrophenyl)amino)butyryl]-5'-ATP; (ANPAB5'-ATP); and 3'-O-(fluorosulfonyl-benzoyl)-5'-ATP (3'-FSB-5'-ATP).

In another preferred embodiment of ribose derivatives of adenosine triphosphate, derivatives with modified 2'- and 3'-positions are used. Erlanger, B. F., and Beiser, S. M. (Proc. Natl. Acad. Sci. U.S.A. 52: 68–74, 1964) teach how to convert ribose containing nucleotides by periodate treatment to 2',3'-dialdehyde containing analogues. Preferred, non-limiting examples include adenosine 5'-triphosphate-2', 3'-dialdehyde; (periodate oxidized 5'-ATP); and adenosine 5'-triphosphate-2',3'-acyclic dialcohol; (periodate oxidized 5'-ATP after reduction with borohydride).

In another preferred embodiment of nicotinamide ribose derivatives of adenosine triphosphates, analogues derived from 2',3'-dialdehyde-containing derivatives are used. Preferred, non-limiting examples of analogues derived from 2',3'dialdehyde-containing adenosine triphosphate derivatives include 5'-ATP-2',3'-dial-[3-(N-(4-azido-2-nitrophenyl)amino)propionic acid hydrazone], (arylazido-β-alanyl-morpholino 5'-ATP); 5'-ATP-2',3'-dial-[3-(3-(N-(4-azido-2-nitrophenyl)amino)propionyl)amino-propionic acid hydrazone]; (arylazido-β-alanyl-β-alanyl-morpholino 5'-ATP); 5'-ATP-2',3'-dial-(4-azido-2,3,5,6, tetrafluorobenzoic acid hydrazone), (perfluorinated arylazido-morpholino 5'-ATP); and 5'-ATP-2',3'-dial-[3-(N-(4-azido-2,3,5,6,-tetrafluorobenzoyl)amino)propionic; acid hydrazone](perfluorinated arylazido-β-alanyl-morpholino 5'-ATP).

In another preferred embodiment of ribose derivatives of adenosine triphosphate, derivatives are used in which the ribose moiety is replaced by another carbohydrate moiety. Preferred, non-limiting examples include adenine 9-β-D-arabinofuranoside 5'-triphosphate, (Ara-A-5'-triphosphate).

In still another preferred embodiment of ribose derivatives of adenosine triphosphate, analogues with a pyrophosphate group at the 2' or 3'-position of the ribose are used. Simoncsits, A., and Tomasz, J. (Biochim. Biophys. Acta 340: 509–515, 1974) teach how to synthesize 2'(3'),5'-dipyrophosphate nucleotides. Preferred, non-limiting examples of adenosine analogues with a pyrophosphate group at the 2' or 3'-position of the ribose include adenosine 3',5'-dipyrophosphate; and adenosine 2',5'-dipyrophosphate.

III. 5.5. Phosphate Derivatives of Adenosine Triphosphates

In another preferred embodiment of adenosine triphosphate derivatives, phosphate derivatives of adenosine triphosphates are used. In one preferred embodiment of phosphate derivatives of adenosine triphosphate, analogues with thiophosphate groups are used. Preferred, non-limiting examples of adenosine triphosphate derivatives containing thiophosphate groups include adenosine 5'-(α-thio)-triphosphate (5'-ATPαS); and adenosine 5'-(γ-thio)-triphosphate (5'-ATPγS).

In another preferred embodiment of phosphate derivatives of adenosine triphosphate, analogues with cyclic phosphate groups are used. Preferred, non-limiting examples of adenosine triphosphate derivatives include adenosine 2',3'-cyclic monophosphate 5'-diphosphate.

In another preferred embodiment of phosphate derivatives of adenosine triphosphate, analogues containing a phosphoramidate moiety are used. Chollet, A., and Kawashima, E. H. (Nucleic Acid Res. 13: 1529–1541, 1985) teach how to synthesize stable 5'-aminoalkylphosphoramidate analogues of deoxynucleotides. Preferred, non-limiting examples of adenosine triphosphate analogues containing phosphoramidate groups include adenosine 5'-triphospho-amidate, 2'-deoxyadenosine 5'-(γ-aminoethylphosphoramidate)-diphosphate, 2'-deoxyadenosine 5'-(γ-aminopropylphosphoramidate)diphoshate, 2'-deoxyadenosine 5'-(γ-aminobutyl-phosphoramidate)diphosphate, 2'-deoxyadenosine 5'-(γ-amino-pentylphosphoramidate)diphosphate, 2'-deoxyadenosine 5'-(γ-aminohexylphosphoramidate) diphosphate.

In another preferred embodiment of phosphate derivatives of adenosine triphosphates, analogues modified at the γ-phosphate group with an ω-(acetyl)pyridino)-n-alkyl moiety or ω-(bromoacetyl)pyridino)-n-alkyl moiety are used. Woenckhaus, C., and Jeck, R. (Meth. Enzymol. 46: 249–258, 1977) teach how to synthesize [ω-(acetyl) pyridino)-n-alkyl]adenosine 5'-triphosphates and [ω-(bromoacetyl)-pyridino)-n-alkyl]adenosine 5'-triphosphates. Preferred, non-limiting examples of adenosine triphosphate analogues modified at the γ-phosphate group with an ω-(acetyl)-pyridino)-n-alkyl or ω-(bromoacetyl)pyridino)-n-alkyl moiety include [3-(2-acetylpyridino)-n-propyl]-5'-ATP, [3-(2-bromoacetylpyridino)-n-propyl]-5'-ATP, [3-(3-acetyl-pyridino)-n-propyl]-5'-ATP, [3-(3-bromoacetyl-pyridino)-n-propyl]-5'-ATP, [3-(4-acetylpyridino)-n-propyl]-5'-ATP, [3-(4-bromoacetyl-pyridino)-n-propyl]-5'-ATP, [4-(3-acetylpyridino)-n-butyl]-5'-ATP, and [4-(3-bromo-acetylpyridino)-n-butyl]-5'-ATP.

III. 5.6. Adenosine Triphosphate Derivatives Containing More Than One Modification In another preferred embodiment of adenosine triphosphate derivatives, analogues are used that contain a combination of the modifications listed above (sections III.5.1.–III.5.5.). Preferred, non-limiting examples of adenosine triphosphate derivatives with two modifications include analogues containing an adenine C8-azido group (or adenine-C2 azido group) and an arylazido group at the 3'-position of the ribose moiety.

Preferred, non-limiting examples of adenosine triphosphate derivatives with three modifications include analogues containing an adenine C8-azido group (or adenine-C2 azido group), an arylazido group at the 3'-position of the ribose moiety, and a γ-thiophosphate group.

III. 6. Adenosine Diphosphates and Derivatives

In another preferred embodiment, adenosine diphosphates (including adenosine 5'-diphosphate (5'-ADP), adenosine 3',5'-diphosphate (3',5'-ADP), and adenosine 2',5'-diphosphate (2',5'-ADP)) and derivatives of adenosine diphosphates are used for thermo-stabilization of the affinity component.

III. 6.1. Adenine-C2 Derivatives of Adenosine Diphosphates

In one preferred embodiment of adenosine diphosphate derivatives, adenine-C2 derivatives are used. Preferred, non-limiting examples of adenine-C2 derivatives of adenosine triphosphates include those listed in section III.5.1. in which the adenosine diphosphate moiety is replaced by an adenosine triphosphate moiety.

III. 6.2. Adenine-C8 Derivatives of Adenosine Diphosphates

In another preferred embodiment of adenosine diphosphate derivatives, adenine-C8 derivatives are used. Preferred, non-limiting examples of adenine-C8 derivatives of adenosine diphosphates include those listed in section III.5.2. in which the adenosine diphosphate moiety is replaced by an adenosine triphosphate moiety.

III. 6.3. Adenine-N6 Derivatives of Adenosine Diphosphates

In another preferred embodiment of adenosine diphosphate derivatives, adenine-N6 derivatives are used. Preferred, non-limiting examples of adenine-N6 derivatives of adenosine triphosphates include those listed in section III.5.3. in which the adenosine diphosphate moiety is replaced by an adenosine triphosphate moiety.

III. 6.4. Ribose Derivatives of Adenosine Diphosphates

In another preferred embodiment of adenosine diphosphate derivatives, ribose derivatives (including deoxy nucleotide analogues) are used. Preferred, non-limiting examples of ribose derivatives of adenosine triphosphates include those listed in section III.5.4. in which the adenosine diphosphate moiety is replaced by an adenosine triphosphate moiety.

III. 6.5. Phosphate Derivatives of Adenosine Diphosphates

In another preferred embodiment of adenosine diphosphate derivatives, phosphate derivatives are used. Preferred, non-limiting examples of phosphate derivatives of adenosine triphosphates include those listed in section III.5.5. in which the adenosine diphosphate moiety is replaced by an adenosine triphosphate moiety. Additional phosphate derivatives are comprised of molecules containing an arylazide moiety coupled to the 5'-phosphate group. Preferred, non-limiting examples of such derivatives, the synthesis of which is described in section IV.12 of Specific Examples include 5'-O-[2-(N-(4-azido-2-nitrophenyl)amino)ethylphosphate]2'-AMP(arylazido-aminoethyl 2',5'-ADP); 5'-O-[3-(N-(4-azido-2-nitrophenyl)amino)propylphosphate]2'-AMP(arylazido-aminopropyl 2',5'-ADP); 5'-O-[4-(N-(4-azido-2-nitrophenyl)amino)butylphosphate]2'-AMP(arylazido-aminobutyl 2',5'-ADP); 5'-O-[5-(N-(4-azido-2-nitrophenyl)-amino)pentylphosphate]2'-AMP (arylazido-aminopentyl 2',5'-ADP); 5'-O-[6-(N-(4-azido-2-nitrophenyl)amino)-hexylphosphate]2'-AMP(arylazido-aminohexyl 2',5'-ADP); 5'-O-[2-(3-(N-(4-azido-2-nitrophenyl)-amino)propionyl)aminoethylphosphate]-2'-AMP, (arylazido-b-alanyl-aminoethyl 2',5'-ADP); 5'-O-[3-(3-(N-(4-azido-2-nitrophenyl)amino)propionyl)-aminopropylphosphate]-2'-AMP, (arylazido-b-alanyl-aminopropyl 2',5'-ADP); 5'-O-[4-(3-(N-(4-azido-2-nitrophenyl)amino)propionyl)aminobutylphophate]-2'-AMP, (arylazido-b-alanyl-aminobutyl 2',5'-ADP); 5'-O-[5-(3-(N-(4-azido-2-nitrophenyl)amino-propionyl)aminopentylphosphate]-2'-AMP, (arylazido-b-alanyl-aminopentyl 2',5'-ADP); 5'-O-[6-(3-(N-(4-azido-2-nitrophenyl)amino)propionyl)aminohexylphosphate]-2'-AMP, (arylazido-b-alanyl-aminohexyl 2',5'-ADP); 5'-O-[2-(4-(N-(4-azido-2-nitrophenyl)amino)butyryl)aminoethylphosphate]-2'-AMP, (arylazido-butyryl-aminoethyl 2',5'-ADP); 5'-O-[3-(4-(N-(4-azido-2-nitrophenyl)-amino)butyryl)aminopropylphosphate]-2'-AMP, (arylazido-butyryl-aminopropyl 2',5'-ADP); 5'-O-[4-(4-(N-(4-azido-2-nitrophenyl)-amino)butyryl)aminobutylphosphate]-2'-AMP, (arylazido-butyryl-aminobutyl 2',5'-ADP); 5'-O-[5-(4-(N-(4-azido-2-nitrophenyl)amino)butyryl)aminopentylphosphate]-2'-AMP, (arylazido-butyryl-aminopentyl 2',5'-ADP); 5'-O-[6-(4-(N-(4-azido-2-nitrophenyl)amino)-butyryl)aminohexylphosphate]-2'-AMP, (arylazido-butyryl-aminohexyl 2',5'-ADP).

III. 6.6. Adenosine Diphosphate Derivatives Containing More Than One Modification In another preferred embodiment of adenosine diphosphate derivatives, analogues are used that contain a combination of the modifications listed above (sections III.6.1.–III.6.5.). Preferred, non-limiting examples of adenosine diphosphate derivatives with two modifications include analogues containing an adenine C8-azido group and an arylazido group at the 3'-position of the ribose moiety.

Preferred, non-limiting examples of adenosine diphosphate derivatives with three modifications include analogues containing an adenine C8-azido group, an arylazido group at the 3'-position of the ribose moiety, and a β-thiophosphate group.

III. 7. Adenosine Monophosphates and Derivatives

In another preferred embodiment, adenosine monophosphates (including adenosine 5'-monophosphate (5'-AMP), adenosine 3'-monophosphate (3'-AMP), and adenosine 2'-monophosphate (2'-AMP)) and derivatives of adenosine monophosphates are used for thermo-stabilization of the affinity component. Preferred examples of adenosine monophosphate analogues contain a modified adenine C2 position (for details see III.6.1.), a modified adenine C8 position (for details see III.6.2.), a modified adenine N6 position (for details see III.6.3.), a modified ribose moiety (for details see III.6.4.), modified phosphate residues (for details see III.6.5.), or a combination of the above listed modifications (for details see III.6.6.).

III. 8. Nicotinamide Mononucleotide and Derivatives

In another preferred embodiment, nicotinamide mononucleotide (NMN) and derivatives of NMN are used for thermo-stabilization of the affinity component. Preferred examples of NMN analogues contain a modified nicotinamide moiety (for details see III.1.6.), a modified phosphate residue (for details see III.6.5.), a modified nicotinamide ribose moiety (for details see III.1.5.), or a combination of the above listed modifications.

IV. Thermo-Stabilization of the Affinity Component by Covalent Binding of NADP(H)-Derived Ligands In another preferred embodiment, the tertiary structure of the affinity component, rhdhfr or rhdhfr derivatives, is thermo-stabilized by covalent crosslinking of structural components with NADP(H)-derived ligands.

One aspect of the present invention is directed to NADP(H)-derived ligands containing reactive groups for covalent conjugation to the affinity component. Preferred, non-limiting examples are NADP(H)-derived ligands modified with one or more halogen group (e.g. bromide groups) as listed in section III.

Another aspect of the present invention is directed to photoactivatable NADP(H)-derived ligands which are useful for covalent crosslinking of structural components of rhdhfr or rhdhfr derivatives. The photoactivatable groups on the NADP)H)-derived ligands are selected from arylazides, fluorinated arylazides, benzophenones, and diazo reagents. These photoactivatable groups, completely inert in the dark, are converted to reactive species upon absorption of a photon of appropriate energy. NADP(H)-derived ligands containing a single photoactivatable group crosslink structural components of rhDHFR or rhDHFR derivatives i) by covalent attachment of the photoactivatable group to the affinity component, and ii) by ionic interactions of their negatively charged phosphate groups with positively charged amino acid residues. NADP(H)-derived ligands containing more than one photoactivatable group introduce crosslinks by covalent attachment at more than one site and, in addition, by ionic interactions. Particularly preferred, non-limiting examples of NADP(H)-derived ligands useful for the introduction of covalent crosslinks are listed in the following sections.

IV. 1. Photoactivatable NADP(H) Derivatives

In one preferred embodiment, photoactivatable NADP(H) derivatives (β and α analogues) are used for crosslinking structural component of rhDHFR or rhDHFR derivatives.

IV. 1.1. Photoactivatable Adenine-C8 Derivatives of NADP (H)

In one preferred embodiment of photoactivatable NADP(H) derivatives, photoactivatable adenine-C8 azido derivatives are used. Holmes, R. E., and Robins, R. K. (J. Am. Chem. Soc. 87: 1772–1776, 1964) teach how to derivatize the adenine moiety with a C8-azido moiety. The synthesis of additional photoactivatable adenine-C8 arylazido derivatives is described in section III.1 of Specific Examples of this invention. Preferred, non-limiting examples of adenine-C8 azido derivatives of NADP(H) include nicotinamide 8-azidoadenine dinucleotide phosphate (8-$N_3$-NADP); nicotinamide 8-(p-azidosalicylamidoethyl)amino-adenine dinucleotide phosphate, (8-(p-azidosalicylamidoethyl)amino-NADP).

IV. 1.2. Photoactivable Nicotinamide Ribose Derivatives of NADP(H)

In another preferred embodiment, oxidized and reduced photoactivatable nicotinamide ribose derivatives of NADP(H) (β and α analogues) are used. In one preferred embodiment of photoactivatable nicotinamide ribose derivatives of NADP(H), analogues with a modified N3'-position are used. Chen, S., and Guillory, R. J. (J. Biol. Chem. 255: 2445–2453, 1980) teach how to synthesize NADP(H) derivatives containing an arylazido-β-alanyl moiety at the N3'-position of the nicotinamide ribose moiety. The synthesis of additional NADP(H) analogues containing a photoactivatable arylazido (or fluorinated arylazido) moiety at the N3'-position is described in section IV.3 of Specific Examples of this invention. Preferred, non-limiting examples include N3'-O-[3-(N-(4-azido-2-nitrophenyl)amino)propionyl]-NADP, (arylazido-β-alanyl NADP; ANPAP-NADP); N3'-O-[3-(3-(N-(4-azido-2-nitro-phenyl)amino)-propionyl)aminopropionyl]-NADP, (arylazido-β-alanyl-β-alanyl-NADP); N3'-O-[2-(N-(4-azido-2-nitrophenyl)amino)-3-(2-pyridyldithio)propionyl]-NADP, (arylazido-S-thiopyridyl)cysteinyl-NADP); and N3'-O-[3-(2-(N-(azido-2-nitrophenyl)amino)-3-(2-pyridyldithio)propionyl)-aminopropionyl]-NADP, (arylazido-(S-thiopyridyl)cysteinyl-β-alanyl-NADP).

In another preferred embodiment of photoactivatable nicotinamide ribose derivatives of NADP(H), analogues derived from N2',N3'-dialdehyde-containing NADP(H) derivatives are used. The synthesis of such derivatives is described in Example 14. Preferred, non-limiting examples of NADP(H) analogues derived from N2',N3'-dialdehyde-containing NADP(H) derivatives include NADP-N2',N3'-dial-[3-(N-(4-azido-2-nitrophenyl)amino)propionic acid hydrazone], (arylazido-β-alanyl-morpholino NADP); NADP-N2',N3'-dial-[3-(3-(N-(4-azido-2-nitrophenyl)amino)propionyl) amino-propionic acid hydrazone], (arylazido-β-alanyl-β-alanyl-morpholino NADP); NADP-N2',N3'-dial-(4-azido-2,3,5,6-tetrafluorobenzoic acid hydrazone), (perfluorinated arylazido-morpholino NADP); and NADP-N2',N3'-dial-[3-(N-(4-azido-2,3,5,6,-tetrafluorobenzoyl)amino)propionic acid hydrazone], (perfluorinated arylazido-β-alanyl-morpholino NADP).

IV. 1.3. Photoactivatable Nicotinamide Derivatives of NADP

In another preferred embodiment of photoactivatable NADP(H) derivatives, nicotinamide derivatives of NADP(H) (β and α analogues) are used. A review of Guillory, R. J., et al. (Annals N.Y. Acad. Sci. 346: 244–279, 1980) teaches how to synthesize photoactivatable nicotinamide derivatives of NADP. Preferred, non-limiting examples photoactivatable nicotinamide derivatives of NADP(H) include 3-diazoacetoxymethyl-pyridine adenine dinucleotide phosphate, and 3-azido-pyridine adenine dinucleotide phosphate.

IV. 1.4. Photoactivatable NADP(H) Derivatives Containing More Than One Modification In another preferred embodiment, derivatives of photoactivatable NADP(H) (β and α analogues) are used that contain a combination of the modifications listed above (sections IV.1.1.–IV.1.3.).

Preferred, non-limiting examples of photoactivatable NADP(H) derivatives with two modifications include NADP(H) analogues containing an adenine C8-azido group and an arylazido-β-alanyl group at the nicotinamide ribose moiety.

Preferred, non-limiting examples of NADP(H) derivatives with three modifications include NADP (H) analogues containing an adenine C8-azido group, an arylazido-β-alanyl group at the nicotinamide ribose moiety, and a 3-diazoacetoxymethyl-pyridine moiety (or 3-azido-pyridine moiety) instead of nicotinamide.

In another preferred embodiment, oxidized and reduced derivatives of photoactivatable NADP(H) (β and α analogues) are used that contain a combination of photoactivatable groups (listed above in sections IV.1.1.–IV.1.3.) and other modifications (listed in sections III.1.1.–III.1.6.).

IV. 2. Photoactivatable Adenosine 2'-Mono-Phospho-5'-Diphosphoribose Derivatives In another preferred embodiment, photoactivatable adenosine 2'-monophospho-5'-diphosphoribose (phospho-ADPR) derivatives are used for thermo-stabilization of the affinity component. Preferred examples of photoactivatable phospho-ADPR analogues are derived from photoactivatable NADP analogues (IV.1.1.–IV.1.4.). Kaplan, N. O. (Meth. Enzymol. 2: 664–668, 1955) teaches how to prepare phospho-ADPR derivatives by treatment of NADP and the corresponding NADP derivatives with *Neurospora crassa* NADase (NAD glycohydrolase).

IV. 3. Photoactivatable NAD(H) Derivatives

In another preferred embodiment, photoactivatable NAD(H) derivatives (β and α analogues) are used for crosslinking structural component of rhDHFR or rhDHFR derivatives.

IV. 3.1. Photoactivatable Adenine-C2 Derivatives of NAD(H)

In one preferred embodiment of NAD(H) derivatives, photoactivatable adenine-C2 derivatives of NAD(H) (β and α analogues) are used. Kim, H., and Haley, B. E. (J. Biol. Chem. 265: 3636–3641, 1990) teach how to synthesize 2-azido-NAD. Preferred, non-limiting examples of photoactivatable adenine-C2 derivatives of NAD(H) include nicotinamide 2-azido-adenine dinucleotide (2-N$_3$-NAD).

IV. 3.2. Photoactivatable Adenine-C8 Derivatives of NAD(H)

In another preferred embodiment of photoactivatable NAD(H) derivatives, photoactivatable adenine-C8 azido derivatives of NAD(H) (β and α analogues) are used. Preferred, non-limiting examples of photoactivatable adenine-C8 derivatives of NAD(H) include those listed in section IV.1.1. in which the NAD(H) moiety is replaced by an NADP(H) moiety.

IV. 3.3. Photoactivatable Adenine Ribose Derivatives of NAD(H)

In another preferred embodiment of NAD(H) derivatives, oxidized and reduced photoactivatable adenine ribose derivatives of NADP(H) (β and α analogues) are used. A review of Guillory, R. J. (Annals N.Y. Acad. Sci. 346: 244–279, 1980) teaches how to synthesize an arylazido-β-alanyl derivative of NAD. Preferred, non-limiting examples include A3'-O-[3-(N-(4-azido-2-nitrophenyl)amino)-propionyl]-NAD, (arylazido-β-alanyl NAD; ANPAP-NAD).

IV. 3.4. Photoactivatable Nicotinamide Derivatives of NAD(H)

In another preferred embodiment of photoactivatable NAD(H) derivatives, nicotinamide derivatives of NAD(H) (β and α analogues) are used. Preferred, non-limiting examples of photoactivatable nicotinamide derivatives of NAD(H) include those listed in section IV.1.3. in which the NAD(H) moiety is replaced by an NADP(H) moiety.

IV. 3.5. Photoactivatable NAD(H) Derivatives Containing More Than One Modification In another preferred embodiment, oxidized and reduced derivatives of photoactivatable NAD(H) (β and α analogues) are used that contain a combination of the modifications listed above (sections IV.1.1.–IV.1.4.).

Preferred, non-limiting examples of photoactivatable NAD(H) derivatives with two modifications include NAD(H) analogues containing an adenine C8-azido group (or adenine C2-azido group) and an arylazido-β-alanyl group at the adenine ribose moiety.

Preferred, non-limiting examples of NAD(H) derivatives with three modifications include NAD(H) analogues containing an adenine C8-azido group (or adenine-C2 azido group), an arylazido-β-alanyl group at the adenine ribose moiety, and a 3-diazoacetoxymethylpyridine moiety (or 3-azido-pyridine moiety) instead of nicotinamide.

In another preferred embodiment, oxidized and reduced derivatives of photoactivatable NAD(H) (β and α analogues) are used that contain a combination of photoactivatable groups (listed above in sections IV.3.1.–IV.3.4.) and other modifications (listed in sections III.3.1.–III.3.6.).

IV. 4. Photoactivatable Adenosine 5'-Diphosphoribose Derivatives

In another preferred embodiment, photoactivatable adenosine 5'-diphosphoribose (ADPR) derivatives are used for thermo-stabilization of the affinity component. Preferred examples of photoactivatable ADPR analogues are derived from photoactivatable NAD analogues (IV.3.1.–IV.3.5.). Kaplan, N. O. (Meth. Enzymol. 2: 664–668, 1955) teaches how to prepare ADPR derivatives by treatment of NADP and corresponding NADP derivatives with *Neurospora crassa* NADase (NAD glycohydrolase).

IV.5. Photoactivatable Adenosine Triphosphate Derivatives

In another preferred embodiment, photoactivatable adenosine triphosphate derivatives (including derivatives of adenosine 5'-triphosphate (5'-ATP), adenosine 3'-monophosphate-5'-diphosphate, and adenosine 2'-monophosphate-5'-diphosphate) are used for thermo-stabilization of the affinity component.

IV. 5.1. Photoactivatable Adenine-C2 Derivatives of Adenosine Triphosphates

In one preferred embodiment of photoactivatable adenosine triphosphate derivatives, adenine-C2 derivatives are used. Kim, H., and Haley, B. E. (J. Biol. Chem. 265: 3636–3641, 1990) teach how to synthesize 2-azido-5'-AMP, from which 2-azido-5'-ATP is synthesized according to standard procedures. Preferred, non-limiting examples of photoactivatable adenine-C2 derivatives of adenosine triphosphates include 2-azido-adenosine 5'-triphosphate.

IV. 5.2. Photoactivatable Adenine-C8 Derivatives of Adenosine Triphosphates

In another preferred embodiment of photoactivatable adenosine triphosphate derivatives, adenine-C8 derivatives of adenosine triphosphates are used. Preferred, non-limiting examples of photoactivatable adenine-C8 derivatives of adenosine triphosphates include those listed in section IV.1.1. in which the adenosine triphosphate moiety is replaced by an NADP(H) moiety.

IV. 5.3. Photoactivatable Ribose Derivatives of Adenosine Triphosphates

In another preferred embodiment of photoactivatable adenosine triphosphate derivatives, ribose derivatives (including deoxy nucleotide analogues) are used. In one preferred embodiment of photoactivatable ribose derivatives of adenosine triphosphates, derivatives containing an arylazide moiety at the 3'-position are used. Jeng, S. J., and Guillory, R. J. (J. Supramol. Structure 3: 448–468, 1975) teach how to synthesize derivatives of adenosine triphosphates modified at the 3'-position with an arylazido group via different spacer molecules. Preferred, non-limiting examples include 3'-O-[3-(N-(4-azido-2-nitrophenyl)amino)propionyl]-5'-ATP (ANPAP-5'-ATP); 3'-O-[4-(N-(4-azido-2-nitrophenyl)-amino)butyryl]-5'-ATP (ANPAB-5'-ATP); and 3'-O-[6-(N-(4-azido-2-nitrophenyl)amino)-caproyl]-5'-ATP (ANPAC-5'-ATP).

In another preferred embodiment of photoactivatable ribose derivatives of adenosine triphosphates, analogues derived from 2',3'-dialdehyde-containing derivatives are used. Preferred, non-limiting examples include 5'-ATP-2',3'-dial-[3-(N-(4-azido-2-nitrophenyl)amino)propionic acid hydrazone], (arylazido-β-alanyl-morpholino 5'-ATP); 5'-ATP-2',3'-dial-[3-(3-(N-(4-azido-2-nitrophenyl)amino)propionyl)amino-propionic acid hydrazone], (arylazido-β-alanyl-β-alanyl-morpholino 5'-ATP); 5'-ATP-2',3'-dial-(4-azido-2,3,5,6-tetrafluorobenzoic acid hydrazone), (perfluorinated arylazido-morpholino 5'-ATP); and 5'-ATP-2',3'-dial-[3-(N-(4-azido-2,3,5,6,-tetrafluorobenzoyl)amino)propionic acid hydrazone], (perfluorinated arylazido-β-alanyl-morpholino 5'-ATP).

IV. 5.4. Photoactivatable Phosphate Derivatives of Adenosine Triphosphates

In another preferred embodiment of photoactivatable adenosine triphosphate derivatives, phosphate derivatives of adenosine triphosphates are used. In one preferred embodiment of photoactivatable phosphate derivatives of adenosine triphosphates, analogues containing an arylazide group (or fluorinated arylazide group) via an aminoalkylphosphoramidate residue are used. Preferred, non-limiting examples of adenosine triphosphate analogues containing an arylazide group (or fluorinated arylazide group) via an aminoalkylphosphoramidate residue include adenosine 5'-O-[γ-(p-azidosalicyl)amidoethyl)diphosphate], adenosine 5'-O-[γ-(p-azidosalicylamidopropyl)diphosphate], adenosine 5'-O-[γ-(p-azidosalicylamido-butyl)diphosphate], adenosine 5'-O-[γ-(p-azidosalicylamidopentyl)diphosphate], adenosine 5'-O-[γ-(p-azidosalicylamidohexyl)diphosphate].

IV. 5.5. Photoactivatable Adenosine Triphosphate Derivatives Containing More Than One Modification In another preferred embodiment of photoactivatable adenosine triphosphate derivatives, analogues are used that contain a combination of the modifications listed above (sections IV.5.1.–IV.5.4.). Preferred, non-limiting examples of photoactivatable adenosine triphosphate derivatives with two modifications include analogues containing an adenine-C8 azido group (or an adenine-C2 azido group) and an arylazido group at the 3'-position of the ribose moiety.

Preferred, non-limiting examples of photoactivatable adenosine triphosphate derivatives with three modifications include analogues containing an adenine-C8 azido group (or an adenine-C2 azido group), an arylazido group at the 3'-position of the ribose moiety, and a (fluorinated) arylazido group attached to the γ-phosphate group via an aminoalkylphosphoramidate residue.

IV. 6. Photoactivatable Adenosine Diphosphate Derivatives

In another preferred embodiment, photoactivatable adenosine diphosphate derivatives (including derivatives of adenosine 5'-diphosphate (5'-ADP), adenosine 3'-monophosphate-5'-monophosphate, and adenosine 2'-monophosphate-5'-monophosphate) are used for thermo-stabilization of the affinity component.

IV. 6.1. Photoactivatable-Adenine-C2 Derivatives of Adenosine Diphosphates

In one preferred embodiment of photoactivatable adenosine diphosphate derivatives, adenine-C2 derivatives are used. Preferred, non-limiting examples of photoactivatable adenine-C2 derivatives of adenosine diphosphates include those listed in section IV.5.1. in which the adenosine diphosphate moiety is replaced by an adenosine triphosphate moiety:

IV. 6.2. Photoactivatable Adenine-C8 Derivatives of Adenosine Diphosphates

In another preferred embodiment of photoactivatable adenosine diphosphate derivatives, adenine-C8 derivatives of adenosine diphosphates are used. Preferred, non-limiting examples of photoactivatable adenine-C8 derivatives of adenosine diphosphates include those listed in section IV.5.2. in which the adenosine diphosphate moiety is replaced by an adenosine triphosphate moiety.

IV. 6.3. Photoactivatable Ribose Derivatives of Adenosine Diphosphates

In another preferred embodiment of photoactivatable adenosine diphosphate derivatives, ribose derivatives (including deoxy nucleotide analogues) are used. Preferred, non-limiting examples of photoactivatable ribose derivatives of adenosine diphosphates include those listed in section IV.5.3. in which the adenosine diphosphate moiety is replaced by an adenosine triphosphate moiety.

IV.6.4. Photoactivatable Phosphate Derivatives of Adenosine Diphosphates

In another preferred embodiment of photoactivatable adenosine diphosphate derivatives, phosphate derivatives of adenosine diphosphates are used. Preferred, non-limiting examples of photoactivatable phosphate derivatives of adenosine diphosphates include those listed in section IV.5.4. in which the adenosine diphosphate moiety is replaced by an adenosine triphosphate moiety. The synthesis of additional phosphate derivatives, comprised of analogues of adenosine 3'-monophosphate-5'-monophosphate or adenosine 2'-monophosphate-5'-monophosphate with an arylazide moiety coupled to the 5'-phosphate group, is described section IV.12 of Specific Examples of this invention. Preferred, non-limiting examples of such derivatives include 5'-O-[2-(N-(4-azido-2-nitrophenyl)-amino)ethylphosphate] 2'-AMP, (arylazidoaminoethyl 2',5'-ADP); 5'-O-[3-(N-(4-azido-2-nitrophenyl)amino)propylphosphate] 2'-AMP, (arylazido-aminopropyl 2',5'-ADP); 5'-O-[4-(N-(4-azido-2-nitrophenyl)amino)-butylphosphate] 2'-AMP, (arylazido-aminobutyl 2',5'-ADP); 5'-O-[5-(N-(4-azido-2-nitrophenyl)amino)pentylphosphate] 2'-AMP, (arylazido-aminopentyl 2',5'-ADP); 5'-O-[6-(N-(4-azido-2-nitrophenyl)amino)hexylphosphate] 2'-AMP, (arylazido-aminohexyl 2',5'-ADP); 5'-O-[2-(3-(N-(4-azido-2-nitrophenyl)amino)propionyl)-aminoethylphosphate]-2'-AMP, (arylazido-β-alanyl-aminoethyl 2',5'-ADP); 5'-O-[3-(3-(N-(4-azido-2-nitrophenyl)amino)propionyl)aminopropylphosphate]-2'-AMP, (arylazido-β-alanyl-aminopropyl 2',5'-ADP); 5'-O-[4-(3-(N-(4-azido-2-nitrophenyl)amino)propionyl)aminobutylphosphate]-2'-AMP, (arylazido-β-alanyl-aminobutyl 2',5'-ADP); 5'-O-[5-(3-(N-(4-azido-2-nitrophenyl)-amino)propionyl) aminopentylphosphate]-2'-AMP, (arylazido-β-alanyl-aminopentyl 2',5'-ADP); 5'-O-[6-(3-(N-(4-azido-2-nitrophenyl)amino)propionyl)-aminohexylphosphate]-2'-AMP, (arylazido-β-alanyl-aminohexyl 2',5'-ADP); 5'-O-[2-(4-(N-(4-azido-2-nitrophenyl)amino)butyryl) aminoethylphosphate]-2'-AMP, (arylazido-butyryl-aminoethyl 2',5'-ADP); 5'-O-[3-(4-(N-(4-azido-2-nitrophenyl)amino)butyryl)-aminopropylphosphate]-2'- (arylazido-butyryl-aminopropyl 2',5'-ADP); 5'-O-[4-(4-(N-(4-azido-2-nitrophenyl)amino)butyryl) aminobutylphosphate]-2'-AMP, (arylazido-butyryl-aminobutyl 2',5'-ADP); 5'-O-[5-(4-(N-(4-azido-2-nitrophenyl)-amino)-butyryl)aminopentylphosphate]-2'-AMP, (arylazido-butyryl-aminopentyl 2',5'-ADP); and 5'-O-[6-(4-(N-(4-azido-2-nitrophenyl)amino)butyryl) aminohexylphosphate]-2'-AMP, (arylazido-butyryl-aminohexyl 2',5'-ADP).

IV. 6.5. Photoactivatable Adenosine Diphosphate Derivatives Containing More Than One Modification In another preferred embodiment of photoactivatable adenosine diphosphate derivatives, analogues are used that contain a combination of the modifications listed above (sections IV.6.1.–IV.6.4.). Preferred, non-limiting examples of photoactivatable adenosine diphosphate derivatives containing more than one modification include those listed in section IV.5.5. in which the adenosine diphosphate moiety is replaced by an adenosine triphosphate moiety.

IV. 7. Photoactivatable Adenosine Monophosphate Derivatives

In another preferred embodiment, photoactivatable adenosine monophosphate derivatives (including derivatives of adenosine 5'-monophosphate (5'-AMP), adenosine 3'-monophosphate (3'-AMP), and adenosine 2'-monophosphate (2'-AMP)) are used for thermo-stabilization of the affinity component. Preferred examples of photoactivatable adenosine monophosphate analogues include those listed in sections IV.5.1.–IV.5.5. in which the adenosine monophosphate moiety is replaced by an adenosine triphosphate moiety.

IV. 8. Photoactivatable Nicotinamide Mononucleotide Derivatives

In another preferred embodiment, photoactivatable nicotinamide monocucleotide (NMN) derivatives are used for thermo-stabilization of the affinity component. Preferred examples of photoactivatable NMN analogues include those listed in section IV.1.2. (nicotinamide ribose derivatives), IV.1.3. (nicotinamide derivatives), IV.5.4. (phosphate derivatives), or analogues that contain a combination of these modifications.

V. Stabilization of the Affinity Component by Noncovalent Binding of Folate-Derived Ligands In another preferred embodiment, the tertiary structure of the affinity component, rhDHFR or rhDHFR derivatives is thermo-stabilized by non-covalent binding of folate and folate-derived ligands. One aspect of the present invention is directed to folate-derived ligands which are useful for providing thermal stability to the affinity component when non-covalently bound. The synthesis of particularly useful, non-limiting examples of folate-derived ligands are described in many publications (e.g. , Domin, B. et al., Molecular Pharmacol., 21:231–238 1981; Riper et al., J. Med. Chem., 25:182–187, 1982; Rosowsky et al., J. Med. Chem. 16:1190–1193, 1973; Rosowsky et al., J. Med. Chem., 21:380–386, 1978; Rosowsky et al., J. Med. Chem. 24:1450–1455, 1981; Chaykovsky et al., J. Med. Chem. 17:1212–1216, 1974; The Anti-Cancer Drugs (William B. Pratt & Raymond W. Ruddon, eds), pp. 98–147, Oxford University Press, NY, 1979.

V. 1. Folates

In one preferred embodiment, folates including folic acid, dihydrofolate, tetrahydrofolate, and folates containing more than one glutamate residue are used for thermo-stabilization of the affinity component.

V. 2. MTX and MTX Derivatives

In another preferred embodiment, 4-amino-4-deoxy-$N^{10}$-methylpteroyl-L-glutamic acid (MTX) and MTX derivatives are used for thermo-stabilization of the affinity component. Particularly useful, non-limiting examples of MTX derivatives are listed in the following sections.

V. 2.1 α-Carboxyl Substituted MTX Derivatives

In one preferred embodiment of MTX derivatives, α-carboxyl-substituted MTX derivatives including α-carboxylester derivatives, α-carboxylamide derivatives, α-carboxylpeptide derivatives, and α-carboxylhydrazide derivatives are used for thermo-stabilization of the affinity component.

V. 2.1.1 α-Carboxylamide Derivatives

Preferred, non-limiting examples of α-carboxylester derivatives of MTX include the α-methylester, α-ethylester, α-propylester, α-butylester, α-pentylester, α-hexylester, α-heptylester and α-octylester of MTX. The esters may be formed from the n- or iso-form of the corresponding alcohols. Further examples include other ester derivatives such as the α-benzylester of MTX.

V. 2.1.2 α-Carboxylamide Derivatives

Preferred, non-limiting examples include the α-amide, α-butylamide, α-benzylamide, and the α-amidoethane sulfonic acid derivative of MTX.

V. 2.1.3 α-Carboxylpeptide Derivatives

Preferred, non-limiting examples include the α-glycyl derivative, α-aspartyl derivative, α-glutamyl derivative and the α-polyglutamyl [1–5] derivative of MTX.

V. 2.1.4 α-Carboxylhydrazide Derivatives

Preferred, non-limiting examples include the α-carboxylhydrazide derivative of MTX.

V. 2.2 γ-Carboxyl Substituted MTX Derivatives

In another preferred embodiment of MTX derivatives, γ-carboxyl-substituted MTX derivatives including γ-carboxylester derivatives, γ-carboxylamide derivatives, γ-carboxylpeptide derivatives, and γ-carboxylhydrazide derivatives are used for thermo-stabilization of the affinity component.

V. 2.2.1 γ-Carboxylester Derivatives

Preferred, non-limiting examples of γ-carboxylester derivatives include the γ-methylester, γ-ethylester, γ-propylester, γ-butylester, γ-pentylester, γ-hexylester, γ-heptylester; and the γ-octylester of MTX. Such esters may be synthesized from the n- or iso-form of the corresponding alcohols. Further examples include other ester derivatives such as the γ-benzylester derivative of MTX.

V. 2.2.2 γ-Carboxylamide Derivatives

Preferred, non-limiting examples include the γ-amide, γ-butylamide, γ-benzylamide, and the γ-amidoethane sulfonic acid derivative of MTX.

V. 2.2.3 γ-Carboxylpeptide Derivatives

Preferred, non-limiting examples include the γ-glycyl derivative, γ-aspartyl derivative, γ-glutamyl derivative, and the γ-polyglutamyl [1–5] derivative of MTX.

V. 2.2.4 γ-Carboxylhydrazide Derivatives

Preferred, non-limiting examples include the γ-carboxylhydrazide derivative of MTX.

V. 2.3 α,γ-Homobisubstituted MTX Derivatives

In another preferred embodiment of MTX derivatives, α,γ-homobisubstituted MTX derivatives including α,γ-dicarboxylester derivatives, α,γ-dicarboxylamide derivatives, α,γ-dicarboxylpeptide derivatives, and α,γ-dicarboxylhydrazide derivatives are used for thermo-stabilization of the affinity component.

V. 2.3.1 α,γ-Dicarboxylester Derivatives

Preferred, non-limiting examples include the α,γ-dimethylester, α,γ-diethylester, α,γ-dipropylester, α,γ-dibutylester, α,γ-dipentylester α,γ-dihexylester, α,γ-diheptylester, and the α,γ-dioctylester of MTX. Such esters may be synthesized from the n- or iso-form of the corresponding alcohols. Further examples include other diester derivatives such as the α,γ-dibenzylester derivative of MTX.

V. 2.3.2 α,γ-Dicarboxylamide Derivatives

Preferred, non-limiting examples include the α,γ-diamide, α, γ-dibenzylamide, and the α,γ-diamidomethane sulfonic acid derivative of MTX.

V. 2.3.3 α,γ-Dicarboxylpeptide Derivatives

Preferred, non-limiting examples include the α,γ-diglycyl, α,γ-diaspartyl, α,γ-diglutamyl, and the α,γ-dipolyglutamyl [1–5] derivative of MTX.

V. 2.3.4 α,γ-Dicarboxylhydrazide Derivatives

Preferred, non-limiting examples include the α,γdicarboxylhydrazide derivative of MTX.

V. 2.4 α,γ-Heterobisubstituted MTX Derivatives

In another preferred embodiment of MTX derivative, α,γheterobisubstituted MTX derivatives including α,γ-dicarboxylester derivatives, α-ester, γ-amide derivatives, and α-ester, γ-hydrazide derivatives.

V. 2.4.1 α,γ-Dicarboxylester Derivatives

Preferred, non-limiting examples include the α-methylester, γ-butylester of MTX and the α-methylester, γ-benzylester of MTX.

V. 2.4.2 α-Ester, γ-Amide Derivatives

Preferred, non-limiting examples include the α-benzylester, γ-butylamide derivative; α-benzylester, γ-benzylamide derivative; α-benzylester, γ-butylamide-p-toluene sulfonic acid derivative; and the α-benzylester, γ-benzylamide-p-toluene sulfonic acid derivative of MTX;

V. 2.4.3 α-Ester, γ-Hydrazide Derivatives

Preferred, non-limiting examples include the α-t-butylester, γ-hydrazide derivative of MTX.

V. 2.4.4 Other α,γ-Heterobisubstituted Derivatives

Preferred, non-limiting examples include the α,γ-diamide derivatives; α,γ-dipeptide derivatives; α,γ-dihydrazide derivatives; α-ester, γ-amide derivatives; α-ester, γ-peptide derivatives; α-amide, γ-ester derivatives; α-amide, γ-peptide derivatives; α-amide, γ-hydrazide derivatives; α-peptide, γ-ester derivatives; α-peptide, γ-ester derivatives; α-peptide, γ-amide derivatives; α-peptide, γ-hydrazide derivatives; α-hydrazide, γ-ester derivatives; α-hydrazide, γ-amide derivatives; and the α-hydrazide, γ-peptide derivatives of MTX.

V. 3. Aminopterin and Aminopterin Derivatives

In another preferred embodiment, 4-amino-4-deoxy-pteroyl-L-glutamic acid (aminopterin) and derivatives thereof are used for thermo-stabilization of the affinity component. Preferred, non-limiting examples include those listed in section V.2 where MTX is replaced by aminopterin.

V. 4. Other Folate Analogs

In another preferred embodiment, other folate analogs, including those derivatized at position 6 (Chaykovsky et al., J. Med. Chem. 17:1212–1216, 1974), are used for thermo-stabilization of the affinity component.

VI. Thermo-Stabilization of The Affinity Component by a Combination of Covalently Bound Crosslinking Reagents or Ligands and Non-Covalently Bound Nadp(H)- or Folate-Derived Ligands In another preferred embodiment, the tertiary structure of the affinity component, rhdhfr or rhdhfr derivatives, is thermo-stabilized by a combination of the stabilization procedures described in sections II–V.

VI. 1. Combinations of Two Stabilization Procedures.

Preferred, non-limiting combinations include a combination of cross-linking reagents and folate-derived ligands; a combination of covalently bound NADP(H)-derived ligands and folate-derived ligands; and a combination of cross-linking reagents and covalently bound NADP(H)-derived ligands.

VI. 2. Combinations of Three Stabilization Procedures

Preferred, non-limiting combinations include a combination of covalently bound NADP(H)-derived ligands, folate-derived ligands, and cross-linking reagents.

VII. Thermo-Stabilization of the Affinity Component by Mutagenesis

In another preferred embodiment, the tertiary structure of the affinity component is thermo-stabilized by mutagenesis.

VII. 1. Site Directed Mutagenesis

In one aspect of this embodiment, the affinity component, recombinant human DHFR, is modified by genetic engineering techniques to create specific cysteine residues in numerous locations within the molecule, separate from the ligand binding site, to facilitate intrachain disulfide bond formation upon oxidation. In one aspect of the invention, a cysteine residue can be engineered at amino acid 133 (Leu 133→Cys 133), to facilitate formation of an intrachain disulfide bond with the native cysteine residue located at amino acid 6 of human DHFR. In another aspect of the invention, amino acids Thr39 and Gly69 are converted by oligonucleotide mutagenesis to cysteine residues facilitating disulfide bond formation within the DHFR molecule. In a third aspect of the invention, amino acids Met52 and Asp94 are changed to cysteine residues. Additional regions of the molecule where intrachain disulfide bond formation can occur via modification of residues to cysteine include, but are not necessarily limited to, amino acids Gly 20 with Ser 119, amino acids Val 120 with Ser 59, amino acids Met11 with Asn49, amino acids Arg 65 with Ala 96, and amino acids Pro 66 with Ala 96. Furthermore, the DHFR can be modified to contain any combination of the mutations described above.

Preferably, the DHFR molecule containing any one of these site-directed mutations is comprised of an active site which binds with an affinity that is comparable to that of the wild type rhdhfr and is thermo-stabilized by intrachain disulfide bond(s) unlike the wild type rhdhfr.

VII. 2. Random Mutagenesis

In another aspect of this embodiment, random mutagenesis is used to thermo-stabilize the affinity component. Several techniques for the introduction of random mutations are described in the literature. The classical technique of utilizing an error prone Taq polymerase results in 1.5 to 2% of all molecules within a given PCR template to contain random mutations. Other random mutagenesis techniques are described by Hermes, et al., Gene 84:143–151 (1989); Mossing, M. C., et al., Methods Enzymol. 208:564 (1991), and in *Current Protocols in Molecular Biology* 1(8), Ausubel, F. M., Brent, R., Kingston, R. E., Moore, D. D., Seidman, J. G., Smith, J. A., and Struhl, K (eds.), John Wiley and Sons, 1994.

VIII. Choice of Enzyme Inhibitor Molecules

Several considerations are important for the choice of enzyme inhibitors suitable for use in the present invention. High affinity binding of the inhibitor to the corresponding enzyme is the most important requirement. The overall binding constant ($K_{off}/K_{on}$) should be in the low nanomolar to picomolar range to guarantee tight binding of radionuclide-derivatized enzyme inhibitor molecules to targeted antibody-enzyme conjugates. Methotrexate represents one example of such an inhibitor. Methotrexate binds to human dihydrofolate reductase with an overall binding constant ($K_{off}/K_{on}$) of $2.1 \times 10^{-10}$ M and competitively inhibits the enzyme with a $K_i$ value of $3.4 \times 10^{-12}$ M (M. R. Appleman, N. Prendergast, T. J. Delcamp, J. H Freisheim, R. L. Blakley, "Kinetics of the Formation and Isomerization of Methotrexate Complexes of Recombinant Human Dihydrofolate Reductase", J. Biol. Chem. 263, 10304–10313m 1988).

One approach to increasing the affinity of enzyme inhibitors is the construction of multisubstrate adduct inhibitors. In principle, such inhibitors can be designed for any enzyme that binds two or more substrates simultaneously (cofactors are considered to be substrates in this context). This includes, but is not limited to, methyl-, formyl- and acetyl-transferases, dehydrogenases, hydroxylases, kinases, and various other enzymes such as dihydropteroate synthase, ATP:L-methionine S-adenosyl transferase, and spermidine synthase. For example, multisubstrate adduct inhibitors for enzymes catalyzing bimolecular reactions can be synthesized by covalent conjugation of both substrates. As demonstrated in several studies, some of these substrate conjugates possess the binding stabilization of both individual substrates, in addition to the entropic advantage of reduced molecularity (see, for example, J. Inglese, R. A. Blatchly, S. J. Benkovic., "A Multisubstrate Adduct Inhibitor of a Purine Biosynthetic Enzyme with a Picomolar Dissociation Constant", J. Med. Chem. 32, 937–940, 1989). Typically, the binding affinity of potent multisubstrate adduct inhibitors is $10^3$–$10^6$ times the binding affinity of either substrate. Another approach to increasing the affinity of the inhibitor-enzyme interaction is to combine a multisubstrate adduct inhibitor with an enzyme complex consisting of two or more copies of the enzyme binding site in sufficiently close position to allow the simultaneous binding of the inhibitors coupled together.

Alternatively, suicide or mechanism-based irreversible enzyme inhibitors may be used. These inhibitors require catalytic conversion by the target enzyme. The inhibitor itself is chemically unreactive, but the product of the enzymic conversion is a highly reactive molecule. This product immediately reacts with an active-site moiety, resulting in covalent attachment of the inhibitor to the enzyme and, thereby, in irreversible inactivation of the enzyme. Due to this mechanism, the efficacy of these inhibitor molecules is determined, not only by their binding affinity, but also by their capability to serve as a substrate for the target enzyme. Enzymes that function by covalent catalysis, especially pyridoxal phosphate and flavin-linked enzymes, are preferred but not the only targets for mechanism-based irreversible inhibitors. Examples of such inhibitors are beta, gamma-unsaturated amino acids used for the irreversible inhibition of pyridoxal-linked aspartate aminotransferase, gamma-cysthathionase, and tryptophan synthetase. Other examples include 2-chloroallylamine and cis-3-chloroallylamine, irreversible inhibitors of nonflavin-linked monoamine oxidase and flavin-linked monoamine oxidase, respectively (R. R. Rando. Mechanism-based irreversible enzyme inhibitors. Meth.Enzymol. 46, 28–41, 1977).

Further important considerations for the choice of suitable enzyme inhibitors include a) minimal reactivity with normal tissues, b) low molecular weight, c) solubility in aqueous solutions, and d) the feasibility of chemical conjugation of the inhibitor to effector molecules without impairment of the binding affinity. Preferred for use in the invention are water-soluble, small molecular weight inhibitors that are capable of fast distribution through the body tissues and that can be cleared rapidly by the kidneys. In order to prevent the development of antibodies against radionuclide-derivatized enzyme inhibitor molecules, inhibitors with molecular weights less than approximately 5,000 daltons are preferred. In one embodiment of the invention, methotrexate (L-4-amino-$N^{10}$-methylpteroyl-glutamic acid), a water-soluble compound with a molecular weight of 508.5 daltons, is used as inhibitor of human dihydrofolate reductase. The gamma-carboxyl group of the glutamate moiety of this inhibitor can be derivatized without impairing its binding to the enzyme.

Although small molecular weight inhibitors are preferred, enzyme inhibitors with molecular weights larger than 5,000 daltons are also included in this invention. For example human placental ribonuclease inhibitor (PRI) is a 50 Kd protein that forms tight complexes with both secretory and intracellular ribonucleases (P. Blackburne, S. Moore. In: The Enzymes (P. D. Boyer, ed.) vol. 15, pp. 317–433, Academic Press, New York, 1982). As a protein with a molecular weight of 50,000 daltons PRI does not meet the desired properties of preferred inhibitors with regard to fast distribution through body tissues and rapid clearance by the kidneys. However, PRI is of human origin and competitively inhibits Rnase A with an extremely low $K_i$ value of $4\times10^{-14}$M, approaching the affinity of avidin for biotin. Moreover, PRI binds to human angiogenin, a blood vessel-inducing protein with 35% sequence homology to pancreatic Rnase, with an even lower $K_i$ value of $7\times10^{-16}$ M (F. S. Lee, R. Shapiro, B. T. Vallee. Tight-binding inhibition of angiogenin and ribonuclease A by placental ribonuclease inhibitor. Biochemistry 28, 225–230, 1989).

IX. Choice of Effector Molecules

Effector molecules used in the practice of the present invention are pharmacologically active agents, such as radionuclides, drugs, hormones, and anti-metabolites. They are selected according to the purpose of the intended application, such as whether for imaging or killing tumor cells. Furthermore, the selection involves the consideration of properties such as water solubility and the ease of covalent attachment to enzyme inhibitors without loss of activity.

One important class of therapeutic and diagnostic agents useful in the invention is chelated metals, including chelated radionuclides useful for tumor therapy, such as $^{186}$Re, $^{90}$Y or $^{212}$Bi, radionuclides useful for radioimaging, such as $^{99m}$Tc or $^{111}$In, chelated paramagnetic ions useful for magnetic resonance imaging, such as Gd or Mn, and radio-sensitizing chelated metals, such as chelated iron or ruthenium. Effector molecules may also include, for example, anti-tumor agents, such as DNA alkylating or cross-linking agents, toxins, and anti-microbial agents, such as polyene antibiotics (exemplified by amphotericin B). Finally, a combination of compounds may be used. This list of examples is in no way intended to be exhaustive nor meant to limit the scope of this invention. Many other effector molecules may be suitable for the purposes of the present invention. An advantage of the pre-targeting concept with therapeutic radionuclides is that longer lived isotopes may have a therapeutic advantage. In the future, radionuclides previously considered too long lived for radioimmunotherapy may be preferred (e.g., $^{225}$Ac, $^{32}$P).

X. Linkage of Enzyme Inhibitor to Effector Molecule

The methods by which enzyme inhibitors and diagnostic or therapeutic agents may be derivatized and covalently coupled are numerous and well known in the art. For example, enzyme inhibitors containing nucleophilic moieties such as primary amine, a thiol, or a hydroxyl group may be reacted with effector molecules that contain electrophilic moieties or have been derivatized with such a moiety. Examples of electrophilic moieties include alkyl halides, alkyl sulfonates, active esters such as N-hydroxysuccinimide esters, aldehydes, ketones, and other electrophilic moieties such as isothiocyano, maleimido, or carboxylic acid chloride residues. Vice versa, effector molecules containing a nucleophilic moiety can be reacted with an electrophilic moiety on the enzyme inhibitor molecule. Thus, any of a wide range of functional groups on both the enzyme inhibitor and the effector molecule may be utilized for conjugation, provided these groups are complementary. Alternatively, effector molecules may be coupled to enzyme inhibitors using hetero- or homobifunctional cross-linking reagents. Suitable reactions would be well known to one skilled in the art based on the nature of the reactive groups that are available or have been introduced to both molecules and information about the active site requirements of the inhibitor and the effector molecule.

Preferred for the coupling of radionuclides to enzyme inhibitors are chelating agents capable of forming a tight metal complex with a variety of pharmaceutically useful metals. Typically, the chelate moiety is coupled to the enzyme inhibitor by reaction with a nucleophilic moiety, such as a primary amino group, or with an electrophilic moiety, such as an active ester.

XI. Conjugation of the Targeting Moiety and the Affinity Component by Recombinant Technology In another aspect of this invention, the affinity component is conjugated by genetic engineering technology to a targeting agent and expressed as a fusion protein. The term "fusion protein" refers to a genetically engineered protein whose coding region is comprised of the coding region residues of a first protein fused, in frame, to the coding region residues of a second protein. In a preferred embodiment of this invention, the fusion protein consists of a protein whose coding region is comprised of the coding region residues of a targeting agent fused, in frame, to the coding region of rhdhfr, mutants, and/or fragments (all of these referred to as DHFR) thereof. In one aspect of this preferred embodiment, the fusion protein is composed of DHFR fused to the immunoglobulin heavy chain in the hinge region, such that when combined with the appropriate light chain, the said fusion protein comprises a Fab fragment linked to DHFR. In another aspect of this embodiment, the said fusion protein is composed of DHFR fused to an immunoglobulin heavy chain in the CH1 region, such that when combined with an appropriate light chain the said fusion protein comprises a Fab fragment linked to DHFR. In another aspect of this embodiment, the said fusion protein can be comprised of DHFR fused to the immunoglobulin heavy chain region in either the CH2 or the CH3 domain. Alternatively, the said fusion protein can be comprised of DHFR fused directly either to the carboxy terminal amino acid or the amino terminal amino acid of the intact immunoglobulin heavy chain. In yet another aspect of this embodiment, the fusion protein is comprised of DHFR fused to the amino terminus or to the carboxy terminus of a immunoglobulin single chain construct ($F_v$ fragment).

In another preferred embodiment of this invention, the human immunoglobulin IgG$_3$ hinge, which consists of 60 amino acid residues, either in its entirety or a portion thereof, may be used as a flexible linker for facilitating linkage of DHFR to the targeting agents described above. In addition, other established flexible linkers known to those skilled in the art may be used.

In still another preferred embodiment, the said fusion protein is comprised of more than one DHFR molecule fused to the targeting agent. In a more preferred embodiment, the said fusion protein is comprised of more than one DHFR molecule fused to the amino and/or carboxy terminal amino acid of an intact immunoglobulin heavy chain or fragments thereof, with and without a flexible linker between the targeting agent and DHFR.

In another preferred embodiment, fusion proteins comprised of DHFR and immunoglobulin heavy chain fragments, are used to synthesize bivalent fusion proteins. Fab'-DHFR fusion proteins may be converted to a bivalent F(ab')$_2$-DHFR molecule by oxidation. An Fv construct may also harbor an available cysteine residue either at its carboxyl terminus or within the $V_H$ and/or $V_L$ fragment to facilitate the formation of a dimeric Fv-DHFR fusion protein by oxidation or by sulfhydryl-reactive crosslinking reagents. The same technology can be used to construct bispecific-DHFR fusion proteins.

XII. Modifications of the Effector Complex

In one preferred embodiment, the effector complex comprises a binding partner to the affinity component and an effector molecule as represented by the following formula:

$$(B)_x-(L)_y-(E)_z$$

where

B is a binding partner that binds non-covalently to the affinity component,

L is a chemical bond or a linking group that may contain one or more functional groups, E is the effector molecule, and x, y, and z are integers greater than zero.

In one aspect of this embodiment, the binding partners is MTX, and MTX derivative, aminopterin, an aminopterin derivative, or another folate derivative as described in section V. In another aspect of this embodiment, L is a chelator moiety capable of binding the effector molecule E, e.g., a radiometal.

XIII. Chelator Moieties Suitable for Covalent Attachment to the Binding Partner In a preferred embodiment, the chelator moiety binds effector molecule (e.g., a radiometal) strongly such that under physiological conditions the rate of loss is very low or negligible. Preferred, non-limiting examples of chelating agents suitable for attachment to the binding partners include polyphosphates (e.g., hexametaphosphoric acid), aminocarboxylic acids (e.g., ethylenediaminetetraacetic acid (EDTA); N-(2-hydroxyethyl)ethylene/diaminetriacetic acid; N,N-di(2-hydroxyethyl)glycine; ethylenebis(hydroxyphenylglycine), diethylenetriamine-pentaacetic acid (DTPA); 1,4,7,10-tetraazacyclododecane-N,N',N'',N'''-tetracetic acid (DOTA); 1,4,7,10-teraazacyclododecane-N,N',N''-triacetic acid; 1-oxa-4,7,10-triazacyclododecane-N,N',N''-triacetic acid; trans(1,2) cyclohexaneodiethylenetriamine pentacetic acid (CDTPA); 1,4,7,10-tetraazacyclododecane-N,N',N''-triacetic acid (D03A); 1-oxa-4,7,10-triazacyclododecane-N,N',n''-triacetic acid (OTTA); 1,3-bis[N-[N-(2-aminoethyl)-2-aminoethyl]-2-aminoacetamido]-2-(4-isothiocyanatobenzyl)propane-N,N,N',N'', N''',N'''',N''''',N''''''-octaacetic acid (LiLo); 3-(4-isothiocyanatobenzyl)-6,16-dioxo-1,5,8,11,14-pentaazacyclohexadecane-N,N',N''-triacetic acid (HETA) (LiLo and HETA are described in U.S. Pat. No. 5,292,868 and U.S. patent application Ser. No. 08/197,086, both of which are incorporated by reference); 1,3-diketones (e.g., trifluoroacetylacetone); aromatic heterocyclic bases, (e.g., 2,2'-dipyridyl, 2,2'-diimidazole, dipicoline amine and 1,10-phenanthroline); oximes (e.g., dimethylglyoxime and salicylaldoxime); peptides containing chelating functionality (e.g., polycysteine, polyhistidine, polyaspartic acid, polyglutamic acid, or combinations of such amino acids); sulfur compounds (e.g., diethyldithiophosptoric acid), etc. Further examples of chelating agents suitable for attachment to the binding partner are derived from $N_3S$ and $N_2S_2$ containing compounds, as described in U.S. Pat. Nos. 4,444,690; 4,670,545; 4,673,562; 4,897,255; 4,965,392; 4,980,147; 4,988,496; 5,021,556 and 5,075,099, all of which are incorporated by reference.

XIV. Synthesis of $(L)_Y$-Complexes

In another preferred embodiment, the effector complex contains multiple chelating moieties that are linked together by one or more linking groups. Such linking groups include amino, imido, nitrilo, and imino groups provided by crosslinking reagents (see above), polyamino acids, oligosaccharides, and synthetic polymers.

XV. Synthesis of $(B)_X$-Complexes

In another preferred embodiment, the effector complex contains more than one MTX molecule joined together via linker molecules with two or more functionalities including crosslinking reagents (see above), polyamino acids, oligosaccharides, and synthetic polymers.

XVI. In Vivo Administration of the System Components

A. Biodistribution of the Targeting Moiety

The administration of the targeting moiety, comprised of the targeting reagent and the affinity component, is the first step in the two step pre-targeting approach. In a preferred embodiment, the targeting moiety shows similar binding activity and similar tumor and normal organ biodistribution when compared to the unconjugated targeting reagent. In one aspect of this embodiment, the targeting moiety is administered in vivo and evaluated with regards to its biodistribution. A model that is useful for the evaluation of tumor and normal tissue targeting is the athymic nude mouse with subcutaneously grown, carcinoembryonic antigen (CEA) producing human colon adenocarcinoma cells. The targeting reagent used in this model is an antibody. A particularly useful antibody to demonstrate tumor targeting in this model is the anti-CEA SC-20 mouse monoclonal antibody. In this embodiment, an effective dose of the targeting moiety in a pharmaceutically acceptable medium is administered in vivo. In another aspect of this embodiment, the targeting moiety is formulated into a composition together with non-toxic, physiologically acceptable carriers or adjuvants for parenteral injection, oral administration in solid or liquid form, or topical administration. Useful compositions for parenteral injection include physiologically compatible sterile aqueous or nonaqueous solutions, dispersions, suspensions or emulsions.

B. Biodistribution of the Effector Complex

The administration of the effector complex, comprised of the binding partner MTX, and a chelator with a complexed effector molecule (radionuclide), is the second step in the two step pre-targeting approach. In a preferred embodiment, the effector complex is cleared rapidly from the normal circulation and normal organs. Preferably, the effector complex is cleared in a similar manner to the chelator-radionuclide complex without the binding partner. In one aspect of this embodiment, the effector complex is administered in vivo and evaluated with regards to its biodistribution. The athymic nude mouse and the rabbit are two models which are useful to determine the normal biodistribution and clearance of the effector complex. In this embodiment, an effective dose of the effector complex in a pharmaceutically acceptable medium is administered in vivo. In another aspect of this embodiment, the effector complex is formulated into a composition together with non-toxic, physiologically acceptable carriers or adjuvants for parenteral injection, oral administration in solid or liquid form, or topical administration. Useful compositions for parenteral injection include physiologically compatible sterile aqueous or nonaqueous solutions, dispersions, suspensions or emulsions.

C. Two Step Delivery of Radionuclides

In a preferred embodiment, an effective dose of the targeting moiety is administered in vivo, followed, after an appropriate period of time, by the administration of an effective dose of the effector complex. During the time between administration of the targeting moiety and the effector complex, the targeting moiety binds to the tumor site and unbound targeting moiety is removed from the circulation. In one aspect of this embodiment, the thermostabilizing ligands such as folate-derived ligands (as described in Part I) are co-injected and maintained at the minimum level in circulation necessary for thermostabilization of the affinity component. In another aspect of this embodiment agents that enhance clearance of the targeting moiety from circulation by uptake through the reticuloendothelial system are included. In yet another aspect of this embodiment, the efficacy of the two step delivery approach is evaluated in tumor bearing athymic nude mice. Preferably, the two step procedure is evaluated with subcutaneously grown CEA positive human colon adenocarcinoma cells in athymic nude mice using the anti-CEA SC-20 monoclonal antibody-rhDHFR conjugate as the targeting moiety.

The following examples are included as illustrative of the present invention and are not considered in any way to limit the scope of the embodiments disclosed herein.

EXAMPLE 1
Incorporation of a Spacer with a Terminal Sulfhydryl Group Through Amino Groups on the Antibody Using SPDP SPDP modified 16.88 was prepared by reacting a 15 molar excess of sulfo-LC-SPDP with the antibody in 0.1 M phosphate, 0.1 M NaCl, pH 7.2 for 30 min. at room temperature with intermittent mixing. A typical reaction contained 5 mg of IgM antibody (6.7 nmoles) and 53 μg of sulfo-LC-SPDP (100 nmoles) in a volume of 2 mL. After derivatization, the SPDP modified antibody was purified on a Sephadex G-25 column equilibrated in 0.1 M phosphate, 0.1 M NaCl pH 7.2, subsequently concentrated on a Centricon-30, and stored at 4° C. at no less than 2 mg/mL. SPDP incorporation was determined by adding dithiothreitol (DTT) to final concentration of 10 mM to an aliquot of the SPDP modified antibody and monitoring the release of 2-pyridylthione at 343 nm. The release of 1 mole of 2-pyridylthione is equivalent to the incorporation of 1 mole of sulfhydryl and can be quantitated with an extinction coefficient of 8,080 $M^{-1}$ $cm^{-1}$. Protein concentration was determined using the BCA protein assay and the degree of sulfhydryl incorporation determined. Immunoreactivity of the SPDP modified 16.88 was determined by measuring binding to the tumor antigen CTAA-16.88 and comparing to the activity of native 16.88 (FIG. 39).

EXAMPLE 2
Incorporation of a Spacer with a Terminal Sulfhydryl Group Through Amino Groups on Dihydrofolate Reductase Using SPDP SPDP modified recombinant human dihydrofolate reductase (rhDHFR) was prepared by reacting a 10 molar excess of sulfo-LC-SPDP with rhDHFR in 0.1 M phosphate, pH 7.5 for 30 minutes at room temperature with intermittent mixing. A typical preparation contained 0.5 mg of rhDHFR (24 nmoles) and 126 μg of sulfo-LC-SPDP (240 nmoles) in a volume of 2 mL. After derivatization, the SPDP modified rhDHFR was purified on a Sephadex G-25 column equilibrated in 0.1 M phosphate, 0.1 M NaCl, pH 7.2 and concentrated on a Centricon-3. Sulfhydryl incorporation (FIG. 40) and protein concentration determination were performed as described for the antibody. Since rhDHFR contains no disulfide bonds, the SPDP's incorporated onto the enzyme could be deprotected with dithiothreitol (DTT) without detrimental effects to the enzyme. To do this, SPDP-rhDHFR was treated with DTT at a final concentration of 10 mM for 20 min. at room temperature in 0.1 M phosphate, 0.1 M NaCl 1 mM EDTA pH 7.2, purified on a Sephadex G-25 column equilibrated in degassed 0.1 M phosphate, 0.1 M NaCl, 1 mM EDTA, pH 7.2., and then concentrated on a Centricon-3. After determining the protein concentration by absorbance at 280 nm, the derivatized rhDHFR was immediately used to prepare the final immunoconjugate. The activity of rhDHFR following sulfo-LC-SPDP modification and following reduction with DTT was evaluated to determine the effects of the treatment on the activity of the enzyme (FIG. 41).

EXAMPLE 3
Formation of the Antibody-Enzyme Complex

The immunoconjugate was prepared by adding a 10–15 molar excess of derivatized rhDHFR to 16.88-SPDP. The reaction was performed in a volume of 2.5 mL of 0.1 M phosphate, 0.1 M NaCl, 1 mM EDTA, pH 7.2 at 4° C. for 3–4 days under $N_2$. One to two mg of 16.88-SPDP (1.3–2.6 nmoles) was used in a typical reaction and the amount or derivatized rhDHFR used determined by the antibody quantity used. After incubation at 4° C., the mixture was concentrated to 1 mL or less and the immunoconjugate purified on a Fractogel 55S column equilibrated in 0.1 M phosphate, 0.1 M, NaCl, pH 7.2. The immunoconjugate was concentrated on a Centriprep-30 membrane and stored at 4° C. The immunoreactivity and protein concentration were determined as described earlier. FIG. 42 shows the immunoreactivity of two preparations of 16.88-DHFR. FIGS. 43 and 44 show the beneficial effects of using the LC-SPDP spacer compared to normal SPDP in three different conjugate preparations. In all cases, the number of active DHFR's on the IgM was improved by using LC-SPDP.

EXAMPLE 4
Assay of Dihydrofolate Reductase Activity

Dihydrofolate reductase concentrations of $10^{-7}$–$10^{-9}$M are easily assayed by monitoring the time dependent decrease in $A_{340}$ caused by the reduction of dihydrofolate and the oxidation of the cofactor nicotinadenine dinucleotide phosphate (NADPH). The assay is performed at 22° C. (room temperature) in 50 mM Tris, pH 7.5 and 60 μM NADPH and initiated by adding dihydrofolate to 50 μM. One enzyme unit is equivalent to the amount of enzyme required to reduce 1 μmole of dihydrofolate to 1 μmole tetrahydrofolate in 1 min. at 22° C. and can be quantitated using an extinction coefficient of 12,300 $M^{-1}$ $cm^{-1}$.

The inhibition rate of DHFR by MTX and its derivatives is determined by the decrease in the conversion of dihydrofolate to tetrahydrofolate. The assay conditions are identical to the assay conditions above with only the addition of methotrexate or its derivatives at [MTX]≦[DHFR]. Derivatives of methotrexate are evaluated by comparing inhibition rates to the inhibition rate of MTX at equivalent concentrations. Inhibition constants ($K_i$) for MTX and its derivatives can be determined by plotting 1/V (v=velocity (μmole)) vs 1/[S] ([S]=substrate concentration, i.e., DHF) at different inhibitor concentrations, determining $Km_{app}$ $$\left(Km_{app} = \frac{1}{x\text{-intercept}}\right), \text{ and using the equation}$$

$$-\frac{1}{Km_{app}} = -\frac{1}{K_i + \left(1 + \frac{[I]}{K_i}\right)} \text{ to solve for } K_i;$$

$$(Km = Km_{app} \text{ at } [I] = 0.$$

EXAMPLE 5
Assay of the Inhibitory Activity of Methotrexate-DTPA on Dihydrofolate Reductase The effects of modifying methotrexate with DPTA were unknown and required a comparison of the activity of equimolar concentrations of methotrexate and DTPA-MTX. Since the opterin ring had not been modified and no additional chromophores had been placed on methotrexate during DTPA modification, the extinction coefficient of MTX (E=22,100 M$^{-1}$cm$^{-1}$ at 302 nm)) was used to determine the concentration of DTPA-MTX. The inhibition of rhDHFR by MTX and DTPA-MTX were then measured under the assay conditions mentioned earlier and compared. FIG. 45 shows that at 1×10$^{-8}$M and 5×10$^{-9}$M inhibitor concentration, the inhibitory effects of DTPA-MTX were virtually identical to MTX inhibition; as indicated by the decreased rates of dihydrofolate reduction.

EXAMPLE 6
Analysis of the Inhibitory Activity of MTX and DTPA-MTX on DHFR Bound in an Antibody DHFR Complex As shown earlier, 16.88-DHFR conjugates have been prepared which possessed easily assayable quantities of rhDHFR. Although the reductase activity was measurable, there was no guarantee that the MTX binding properties of the conjugated enzyme had not been affected during the modification steps. To confirm that MTX binding was proportional to the dihydrofolate reductase activity in 16.88-DHFR, the DHFR activity in the conjugate was titrated to an equivalent amount of native rhDHFR and these activity equivalents were compared for their ability to be inhibited by MTX and DTPA-MTX. FIG. 46 shows the results of MTX inhibition of equivalent activities of native rhDHFR and 16.88 bound rhDHFR and indicates that MTX binding is proportional to the reductase activities regardless of whether it is free or in conjugate form. An identical experiment performed using DTPA-MTX (FIG. 47) confirmed the methotrexate data. From these results, not only has the reductase activity been maintained in the conjugate, but also the ability of MTX and DTPA-MTX to bind to and inhibit the conjugated rhDHFR.

EXAMPLE 7
Synthesis of DTPA-MTX

Much effort has been devoted toward potent folate analogues and it is well known that the glutamate moiety contributes to the binding of MTX to dihydrofolate reductase while the γ-carboxyl does not. We have designed MTX analogues that contain a chelator molecule at the γ-carboxyl group of the glutamic acid portion.

The synthesis of DTPA-MTX is shown schematically in FIG. 48. The MTX-AB-GH was prepared using the general method of Rosowsky et al., J. Med. Chem., 1981, 24, 1450–1455. The DTPA dianhydride (9.3 mg, 25μmol) was dissolved in DMF and stirred with Et$_3$N (0.1 mL) for 5 min. MTX-AB-GH 6.8 mg (13 μmol) in 2 mL of CH$_3$CN was added to the above mixture and stirred overnight at room temperature. Solvents were evaporated and the residue was heated to 50° C. with 1N HCl for 1 hour. The reaction mixture was evaporated to dryness and the residue was purified by HPLC (a C$_{18}$, reversed-phase silica gel column, absorbance at 280 nm, the mobile phase was formed with 2% acetic acid (pump A) and 2% acetic acid in 50% methanol (pump B); t$_R$=17.56 min (cf. t$_R$ of MTX=25.26 min) to give 4.1 mg (38%) of product; FAB-MS m/z=844 (M+H)$^+$; $^1$H NMR (D$_2$O)δ8.49 (s,1H),δ 7.52 (d,J=8.6 Hz, 2H)δ6.72 (d, j=8.6 Hz, 2H), δ4.4 (m, 1H), δ3.0–3.95 (m, 18H)δ3.7 (s,2H),δ3.1(s, 3H), δ2.39(t, 2H),δ1.9–2.3 (m, 2H).

EXAMPLE 8
Clearance of $^{111}$In-DTPA-MTX from Athymic Mice
Radiolabeling DTPA-MTX with In-111

$^{111}$InCl$_3$ (1.5 mCi) is mixed with 0.06 mL (0.6mg) DTPA-MTX, 0.02 mL 0.06 sodium citrate pH 5.5, and 0.01 mL 0.60 sodium acetate pH 5.5 for 30 minutes to 215 minutes at room temperature. Thin layer chromatography on plastic backed silica gel strips (1.1 ammonium acetate : methanol) using 0.001 mL of the final reaction solution showed greater than 95% incorporation of $^{111}$In into the $^{111}$In-DTPA-MTX complex. FIG. 49 shows the migration of $^{111}$In-DTPA-MTX in the silica gel with an R$_f$ of 0.5 to 0.7. Free $^{111}$In does not migrate from the origin in this system.

This example compares the whole body clearance of $^{111}$In-DTPA-MTX with that of $^{111}$In-DTPA. $^{111}$In-DTPA is known to clear rapidly from the circulation with little retention in normal tissues. Clearance of the $^{111}$In-DTPA-MTX at a rate similar to that of $^{111}$In-DTPA would indicate that rapid body clearance of the portion of the conjugate not bound in tumor tissue by antibody-DHFR may be expected. Such rapid clearance would ensure that nearly all the unbound radionuclide would decay outside the body.

Three athymic nu/nu mice were injected via the lateral tail vein with 50 uCi $^{111}$In-DTPA-MTX in 0.5 mL 10% normal mouse serum in phosphate buffered normal saline. A second group of three animals received 50 uCi $^{111}$In-DTPA by the same route. All animal were examined for whole body retention of In-111 in a Capintec dose calibrator at 0.5, 1, 2, 3, 4, and 24 hours after injection.

Figure 50:
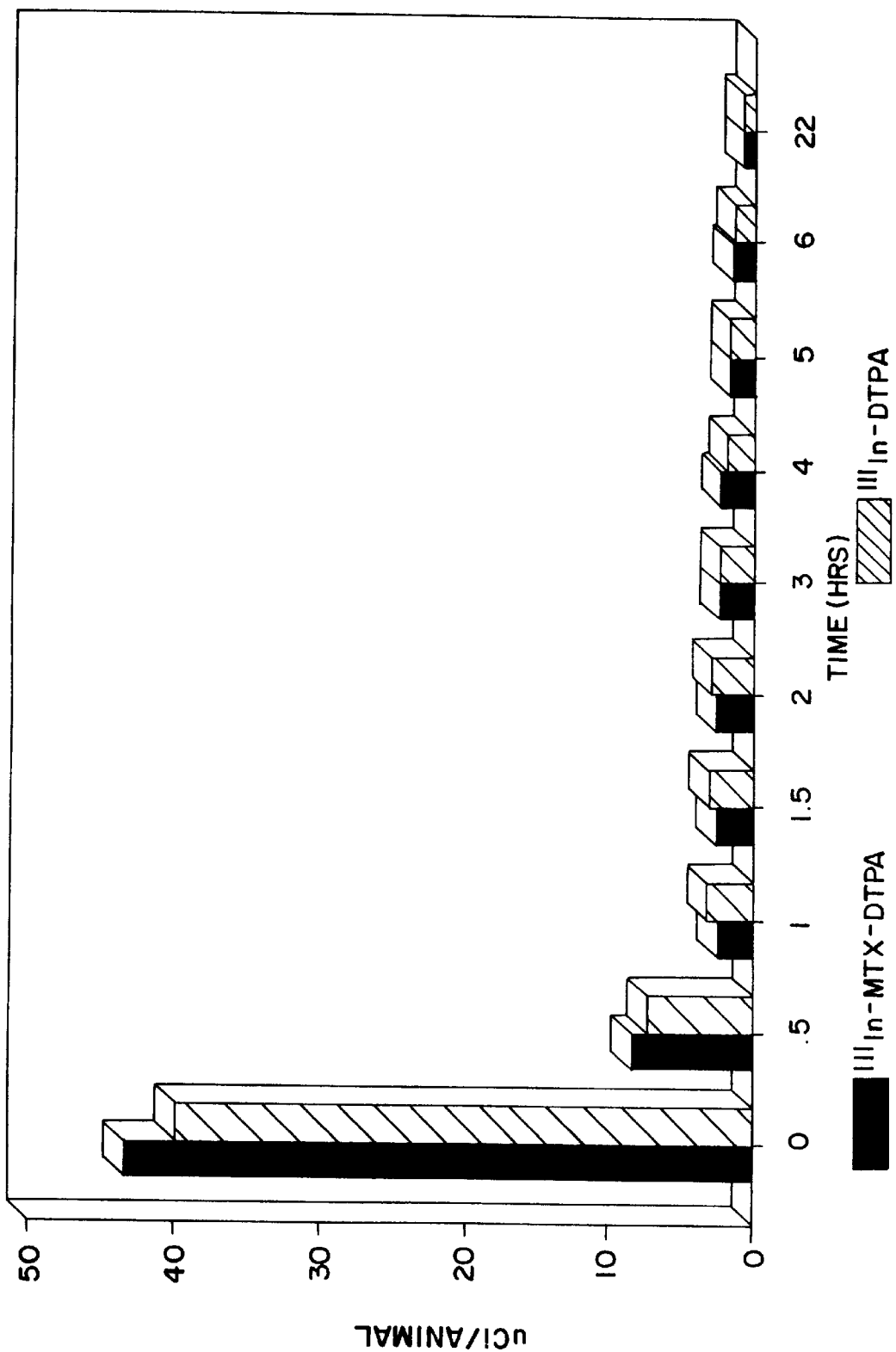

Results shown in FIG. 50 indicate that the $^{111}$In-DTPA-MTX and the $^{111}$In-DTPA clear from the mice at similar rates indicating the likelihood of rapid urinary excretion of a DTPA-MTX not bound to antibody-DHFR.

EXAMPLE 9
Binding of $^{111}$In-DTPA-MTX to Tumor Cell-Bound Antibody-DHFR

This example examines the targeting of $^{111}$In-DTPA-MTX to antibody-DHFR bound to K562 cultured erythroleukemia cells in vitro. For this demonstration, DHFR was coupled to the murine antibody to the human transferrin receptor (5E9C11) using the methods described in example 1. This antibody rather than the human anti-colon carcinoma antibody 16.88 was used since an antibody that binds to epitopes on the surface of cultured cells was required for this in vitro demonstration.

In the first study binding of antibody-DHFR to the target cells was assessed in a titration using concentrations of antibody-DHFR of 1.5, 3.0, 6.0, 12.0, and 24.0 ug/mL mixed at 4° C. with 1×10$^6$ K562 cells in a medium consisting of Hanks Balanced Salt Solution containing 1% bovine serum albumin (protease-free). The reaction volume was 0.2 mL reacted for 60 minutes in an ice bath to prevent internalization of the antibody bound to the transferrin receptor. After washing away excess antibody, 10 ng $^{111}$In-DTPA-MTX (0.53 uCi) was added and the reaction continued for 30 minutes in an ice bath.

Results of the titration are shown in FIG. 51. Non-specific binding of the $^{111}$In-DTPA-MTX, determined with antibody to which no DHFR was conjugated, averaged 0.85% at all antibody concentrations. The study demonstrated that $^{111}$In-DTPA-MTX can bind to antibody-DHFR bound to tumor cells. The extent of binding was sufficient to saturate all available DHFR sites as determined from estimates of the amount of DHFR bound to the cells and the specific activity of the $^{111}$In-DTPA-MTX. As no plateau level was reached it is apparent that at an antibody-DHFR concentration of 24 ug/mL the available binding sites on the tumor cells were not saturated in this study.

In the second study, the lowest concentration of antibody-DHFR giving significant binding above the background level (6.0 ug/Ml) was used in a titration of the $^{111}$In-DTPA-MTX using concentrations of 12.5, 25, 50, 100, or 200 ng/Ml (0.31 to 3.7 Uci/Ml) with conditions identical to those described for the first study. Results are shown in FIG. 52.

Again binding of $^{111}$In-DTPA-MTX to cell-bound antibody-DHFR was demonstrated. At concentrations above 50 ng/Ml, binding reached a plateau level indicating saturation of the available DHFR binding sites, in agreement with the conclusions of the first study.

EXAMPLE 10
Stabilization of Dihydrofolate Reductase (rhDHFR)

In our most preferred embodiment we use stabilized rhDHFR (Dr. James Freisheim, Medical College of Ohio, Toledo, Ohio.) as the enzyme. DHFR was stabilized through covalent conjugation of the enzyme with a photoaffinity analog of NADP$^+$(ANPAP-NADP) followed by photoactivation using a tungsten halogen lamp (615 W; DVY; 3400° K).

A 10-fold molar excess of the photoaffinity analog was mixed with the enzyme, and the volume adjusted to a protein concentration of 1 mg/ml using 10 mM Tris-HCl buffer (pH 7.5). The mixture was kept in ice at a 10 cm distance from the light source while photoactivation was carried out for 5 minutes with occasional stirring. An aliquot was assayed for DHFR activity before and after photoactivation. The NADP$^+$-linked enzyme was purified by gel-filtration using 10 mM sodium phosphate buffer, pH 7.2, containing 20 mM NaCl. Fractions were assayed for DHFR activity before they were pooled for protein estimation (using Pierce BCA reagent) and determination of incorporation of NADP$^+$ moieties per enzyme molecule.

Stability of the conjugated enzyme was determined by incubating at 37° C. for several hours. Percent stability was calculated by comparing with a sample kept at 4° C.

Results
Conjugation
  Photoactivation Time: 5 minutes
  Percent remaining activity following photoactivation: 100%
  Number moieties per enzyme molecule 2.21:1

| | Stability | | | | | |
|---|---|---|---|---|---|---|
| | Time (minutes) | | | | | |
| Sample | 0 | 30 | 60 | 120 | 180 | 1080 |
| ANPAP-NADP$^+$-rhDHFR | 100[1]% | N.T.[2] | 82[1]% | 78[1]% | 78[1]% | 67[3]% |
| rhDHFR | 100[1]% | 18[1]% | 10[1]% | N.T. | N.T. | N.T. |

[1]Values represent percent enzyme activity remaining after incubation at 37° C.
[2]N.T. - Not Tested.
[3]Values represent percent enzyme activity remaining after incubation at 23° C.

Synthesis of the stabilizer of N3'-O-[3-(4-azido-2-nitrophenyl)amino]propionyl NADP$^+$(ANPAP-NADP)

A modified procedure of the Chen and Guillory's method (Chen, S. and Guillory, R. J., J. Biol. Chem., 1980, 255, 2445–2453) was used and the detailed procedure was as follows: A dimethyl formamide (DMF) solution of carbodiimidazole (CDI) (324 mg, 2 mmol) and 3-(4-azido-2-nitrophenylamino) propionic acid (Jeng, S. J. and Guillory, R. J., J. Supramolecular Structure, 1975, 3, 445–468) (15 mg, 0.6 mmol) was stirred at room temperature for 15 min. Then about 3 ml aqueous solution of NADP$^+$(64.6 mg, 0.08 mmol) was added to the DMF solution. Stirring was continued overnight under a nitrogen atmosphere. The solvent was then removed by a rotary evaporator and the residue was washed with acetone by centrifugation. The residue was then dissolved in a small amount of water and purified by preparative thin layer chromatography (Taper® plate; solvent system: 1-butanol/water/HOAc=5/3/2). The material ($R_F$=0.4) was recovered. The compound was further purified by HPLC (Reverse Phase $C_{18}$ column UV@ 260 nm).

EXAMPLE 11
Functional Activities and Thermo-stability of the Affinity Component A. Binding Activity The catalytic activity of the affinity component is measured spectrophotometrically at 25° C. in a total volume of 1.0 ml containing 40 mM Tris-HCl (pH 7.5), 0.07 mM NADPH, 60 mM dihydrofolate and an aliquot of the affinity component. The activity is determined from decreasing the absorbance at 340 nm using the linear portion of the slope. A control reaction mixture without dihydrofolate, is used to determine the background.

B. Catalytic Activity

Equimolar amounts of affinity component and its binding partner [$^3$H]-MTX are incubated in 0.02 ml of 10 Mm Tris-HCl (pH 7.5) for 1 hr at room temperature. The reaction mixture is then passed through 0.8 ml of Sephadex G-25 equilibrated with phosphate buffered saline and pre-washed with 1% (w/v) bovine serum albumin. The amount of affinity component bound [$^3$H]-MTX is calculated from the radioactive counts in the void volume of the column. Heat inactivated affinity component is used to determine background values.

C. Thermo-Stability Assay

The affinity component (0.03 mg) is incubated in 10 mM Tris-HCl (pH 7.5) at 37° C. and 4° C. Aliquots (0.01 ml), withdrawn at different time points, are assayed for both binding and catalytic activity of the affinity component as described (Example 11, A and B).

Figures 1, 2:
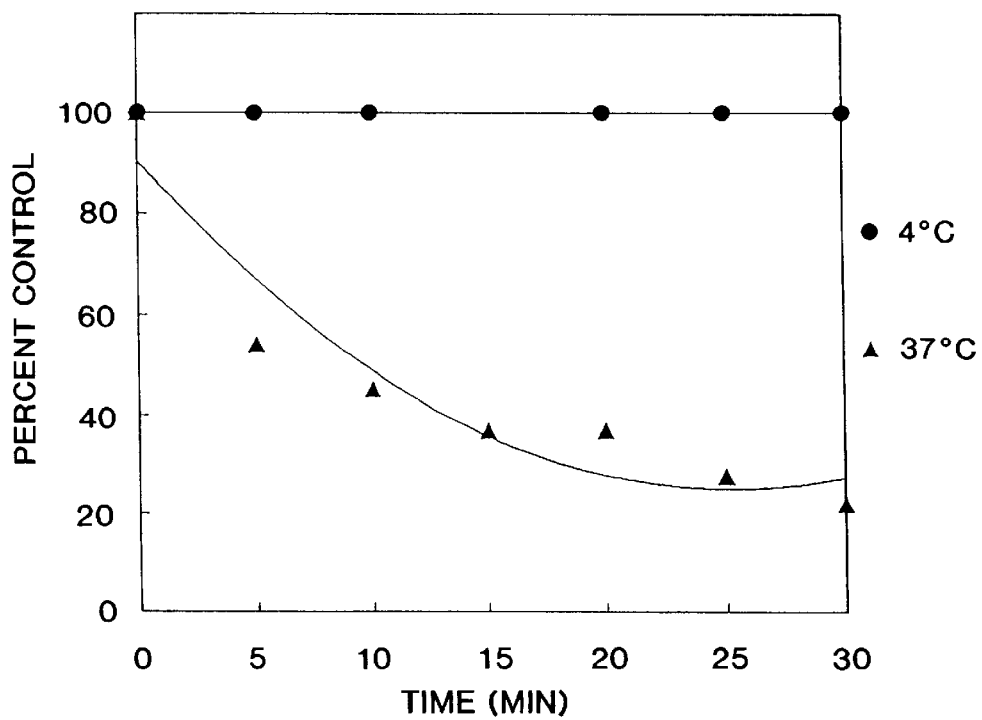
FIG. 1 shows the effect of temperature on the binding activity of the affinity component.
FIG. 2 shows the effect of temperature on the catalytic activity of the affinity component.

FIGS. 1 and 2 show the effect of temperature on the binding and the catalytic activity of the affinity component.

EXAMPLE 12
Thermo-stabilization of the Affinity Component by Covalent Binding of Crosslinking Reagents A. Carbodiimide-Mediated Crosslinking A 20–50 fold molar excess of 1-ethyl-3-(3dimethylaminopropyl)carbodiimide is added to 1.0 ml of 0.05 M sodium acetate buffer (pH 4.5) solution containing 0.5 mg of affinity component (0.024 nmol) and 32.25 nmol of NADP$^+$. After two hours reaction at room temperature, the modified affinity component is purified by gel-filtration on Sephadex G-25 (column volume: 3 ml). The fractions containing binding activity are pooled and concentrated in vacuo.

B. Crosslinking with Homobifunctional Imidoesters

A 100–200 fold molar excess of the crosslinking reagent (DMP, DMS, or DMA) is added to 1.0 ml of 50 mM sodium borate buffer (pH 8.4) containing 0.5 mg of the affinity component (0.024 nmol) and 32.25 nmol of NADP$^+$. After a one hour reaction at room temperature, the modified affinity component is purified by gelfiltration on Sephadex G-25 (column volume 3.0 ml). The fractions containing binding activity are pooled and concentrated in vacuo.

C. Crosslinking with Homobifunctional N—Hydroxysuccinimide Esters

A 10–15 fold molar excess of the crosslinking reagent (sulfo-DST) is added to 1.0 ml of 50 mM sodium borate buffer (pH 8.5) containing 0.5 mg of the affinity component (0.024 nmol) and 32.25 nmol of NADP$^+$. After a 45 min reaction at room temperature, the affinity component is purified by gel filtration on Sephadex G-25 (column volume: 3 ml). The fractions containing binding activity are pooled and concentrated in vacuo.

D. Crosslinking with Heterobifunctional Reagents Containing an
Amine-Reactive and a Sulfhydryl-Reactive Group A 5–20 fold molar excess of the crosslinking reagent (SPDP, or SIAB) is added to 1.0 ml of 50 mM sodium borate buffer (pH 8.5) containing 0.5 mg of the affinity component (0.024 nmol) and 32.25 nmol $NADP^+$. After a 45 min reaction at room temperature, the modified affinity component is purified by gel filtration on Sephadex G-25 (column volume : 3 ml). The fractions containing binding activity are pooled and concentrated in vacuo.

E. Crosslinking with Amine-Reactive Photoactivatable Heterobifunctional Reagents A 10–20 fold molar excess of the crosslinking reagent (sulfo-SANPAH, or sulfo-SAND) is added to 1.0 ml of 50 mM sodium borate buffer (ph 8.5) containing 0.5 mg (0.024 nmol) of the affinity component, and 32.25 nmol of $NADP^+$. After a 45 min at room temperature, the modified affinity component is purified by gel filtration on Sephadex G-25 (column volume: 3 ml) and fractions containing binding activity are pooled. The pooled fractions are then photolyzed for 5–10 min using a tungsten halogen lamp (650W, DVY, 3400K°) (distance between sample and lamp is 10–12 cm). During photolysis, the affinity component is kept in ice and continuously stirred.

EXAMPLE 13

Thermo-Stability Assays of Crosslinker-derivatized Affinity Component

A. Thermo-Stability of the Affinity Component Darivatized with Carbodiimide

An aliquot (0.075 ml) of the modified affinity component (see section III.1) is mixed with equal volume of either PBS or normal human serum, and the mixture is incubated at 37° C. for several hours. At different time points, an aliquot (0.025 ml) is withdrawn from the reaction mixture and is frozen immediately at −20° C. until the catalytic assay and binding assay of the affinity component are carried out as described in Example 11.

FIG. 3 shows the thermo-stabilizing effect of carbodiimide-mediated crosslinking on the catalytic activity of the affinity component.

B. Thermo-Stability of the Affinity Component Derivatized with Homobifunctional imidoesters An aliquot (0.075 ml) of the modified affinity component (see Example 12) is mixed with equal volume of either buffer or normal human serum, and the mixture is incubated at 37° C. for several hours. At different time points, an aliquot (0.025 ml) is withdrawn from the reaction mixture and is frozen immediately at −20° C. until the catalytic assay and binding assay of the affinity component are carried out as described in Example 11.

FIG. 3 shows the thermo-stabilizing effect of crosslinking with homobifunctional imidoesters on the catalytic activity of the affinity component.

Figure 4A:
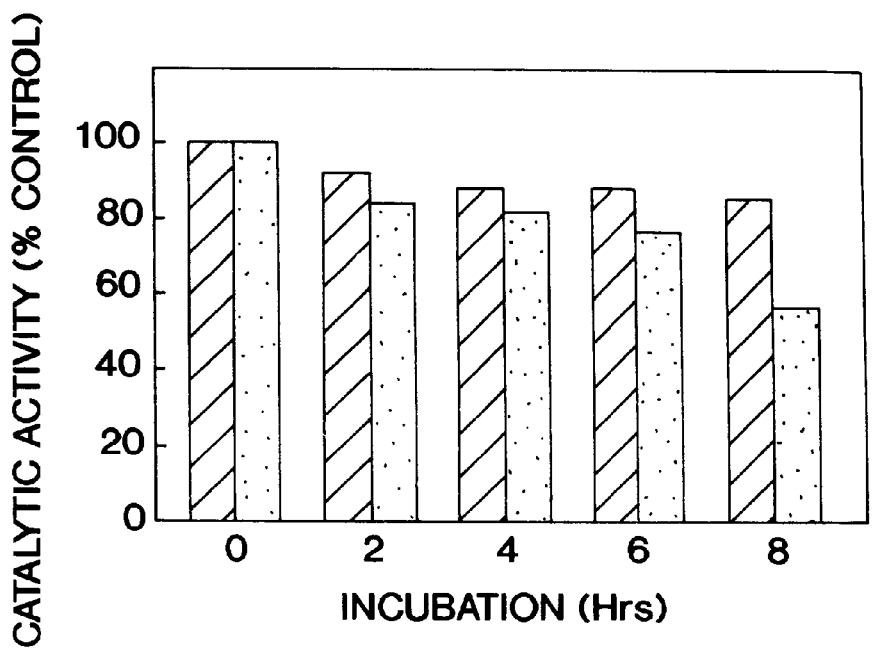
FIGS. 4(A) & (B) show the thermo-stability of the affinity component derivatized with dimethylpimelimidate. The hatched bars refer to incubation in buffer, and the dotted bars refers to incubation in normal human serum.
Figure 4B:
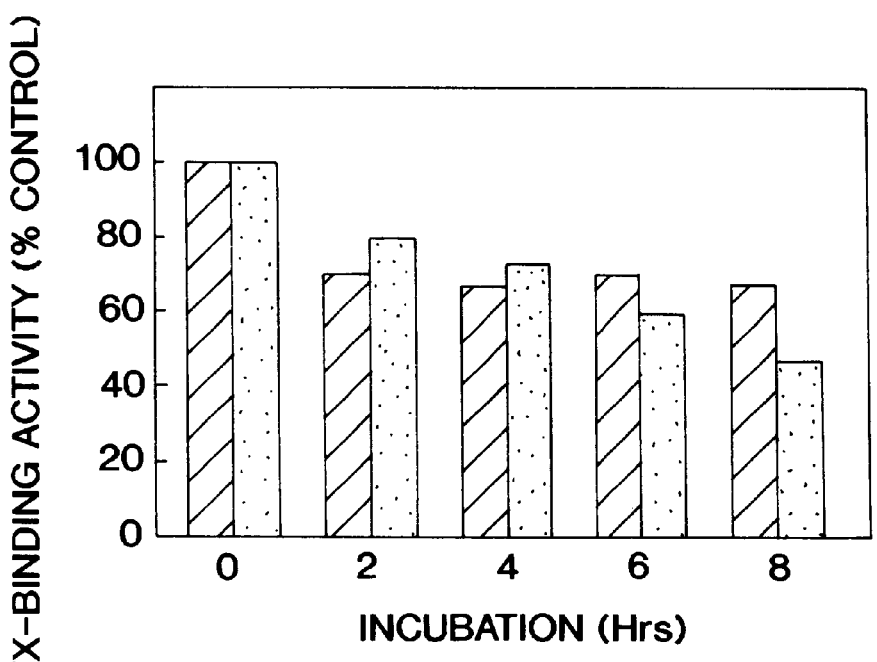

FIG. 4 compares the stabilizing effect of crosslinking with the homobifunctional imidoester, DMP, with respect to the catalytic and binding activity of the affinity component.

C. Thermo-Stability of the Affinity Component Derived with Homobifunctional N—Hydroxysuccinimide Esters An aliquot (0.075 ml) of the modified affinity component (see Example 12) is mixed with equal volume of either PBS or normal human serum, and the mixture is incubated at 37° C. for several hours. At different time points, an aliquot (0.025 ml) is withdrawn from the reaction mixture and is frozen immediately at −20° C. until the catalytic assay and binding assay of the affinity component are carried out as described in Example 11.

FIG. 3 shows the thermo-stabilizing effect of crosslinking with homobifunctional N-hydroxysuccinimide esters on the catalytic activity of the affinity component.

D. Thermo-Stability of the Affinity Component Derivatized with Heterobifunctional Reagents Containing an Amine-Reactive and a Sulfhydryl-Reactive Group An aliquot (0.075 ml) of the modified affinity component (see Example 12) is mixed with an equal volume of either PBS or normal human serum, and the mixture is incubated at 37° C. for several hours. At different time points, an aliquot (0.025 ml) is withdrawn from the reaction mixture and is frozen immediately at −20° C. until the catalytic assay and binding assay of the affinity component are carried out as described in Example 11.

E. Thermo-Stability of the Affinity Component with Amine-Reactive Photoactivatable Heterobifunctional Reagents An aliquot (0.075 ml) of the modified affinity component (see section III.5) is mixed with equal volume of either buffer or normal human serum, and the mixture is incubated at 37° C. for several hours. At different time points, an aliquot (0.025 ml) is withdrawn from the reaction mixture and is frozen immediately at −20° C. until the catalytic assay and binding assay of the affinity component are carried out as described in Example 11.

FIG. 3 shows the thermo-stabilizing effect of crosslinking with amine-reactive photoactivatable heterobifunctional reagents on the catalytic activity of the affinity component.

EXAMPLE 14

Synthesis of NADP(H)-Derived Ligands

A. Synthesis of 8-Br-NADP

To a cooled solution of NADP (787 mg) in 10 ml acetic acid/sodium acetate (0.5 M, pH 4.5) is added a volume of 160 $\mu$l bromine solution in the dark. The reaction mixture is allowed to warm to room temperature in about two hours. After addition of 10 ml water, the excess of bromine is removed by extraction with HCL. The crude product is purified by ion-exchange chromatography.

B. Synthesis of 8-Br-NADPH

Three hundred fifty milligrams (350 mg) of $Na_2S_2O_4$ is added in two portions over a 30 min period to 10 ml of a 1.0 M $NH_4HCO_3$ solution containing 270 mg of 8-Br-NADP. Following addition of $BaCl_2$-$H_2O$ (484 mg) to the reaction mixture, the precipitate is removed by centrifugation. The product is isolated by precipitation with three volumes of cold (−20° C.) acetone.

C. Synthesis of 8-aminoethylamino-NADPH (8-AEA-NADPH)

To a 0.1 ml aqueous solution of 8-Br-NADP (40 mg), 0.4 ml each of 1,2-diaminoethane and DMSO are added. The reaction mixture is stirred for three days at room temperature and the product is purified by ion-exchange chromatography.

Other diaminoalkanes, like 1,4-diaminobutane or 1,6diaminohexane, can be used in place of 1,2 diaminoethane.

D. Synthesis of (8-p-Azidosalicylicamidoethyl)-Amino-NADPH (8ASAEA-NADPH)

Figure 5:
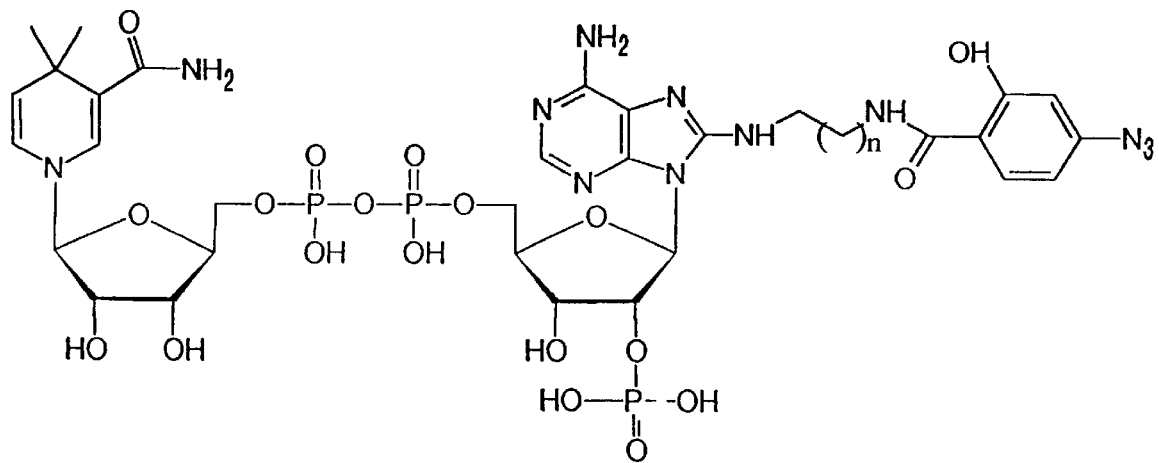
FIG. 5 gives the structure of 8-ASAEA-NADPH. (The "n" indicates the number of carbon atoms.)

Azidosalicylic acid (6.4 mg) is added to the aqueous solution (3.4 ml) containing 20 mg of 8-AEA-NADPH and the reaction is allowed to proceed in the dark for 12 hours with continuous stirring. The product is purified by ion-exchange chromatography. The structure of 8-ASAEA-NADPH is shown in FIG. 5 (n represents the number of carbon atoms).

E. Synthesis of 3-(N-(4-Azido-2-Nitrophenyl)-Amino) Propionic Acid (ANPAP)

4-azido-1-fluoro-2-nitro-benzene (90 mg) is mixed with an aqueous solution (0.5 ml) containing 3-aminopropionic acid (53 mg) and $Na_2CO_3$ (106 mg). Following addition of 2 ml of ethanol and 0.5 ml of water, the solution is heated for 24 h at 55° C. After removal of the unreacted materials by several ether extractions, the product (3-(N-(4-azido-2-nitrophenyl)-amino)propionic acid) is obtained by ether extraction of the acidified (pH 2.0) aqueous phase.

The synthesis can also be performed with other ω-aminocarboxylic acids, e.g., 4-aminobutyric acid or 6-aminohexanoic acid or small polyamides, e.g. 3-(N-(3-aminopropionyl)amino)propionic acid.

F. Synthesis of ANPAP-NADP

ANPAP (37.5 mg) is activated with carbonyldiimidazole (81 mg) in dry dimethylformamide (0.5 ml) for 15 min prior to the addition of 0.5 ml water containing 16 mg $NADP^+$. Following stirring overnight, the product is purified by reversed phase chromatography.

Figure 6:
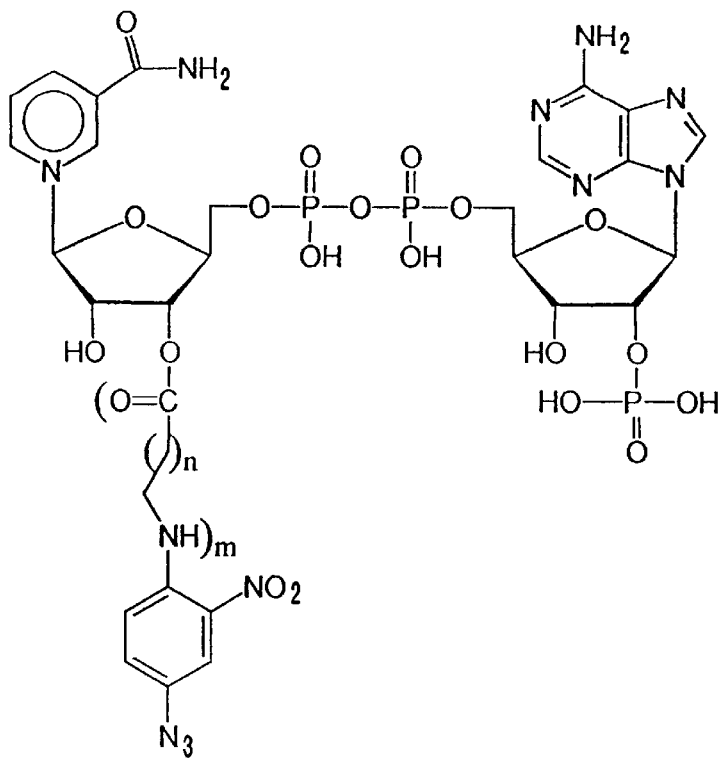
FIG. 6 gives the structure of ANPAP-NADP. (The "n" indicates the number of carbon atoms, and the "m" indicates the number of nitrogen atoms.)

The structure of N3'-O-[3-(N-(4-azido-2-nitrophenyl)amino)propionyl]-NADP (ANPAP-NADP) is shown in FIG. 6 (n represents the number of carbon atoms and m represents the number of nitrogen atoms). Analogues of ANPAP-NADP are easily synthesized when the 3-amine-propionic acid moiety (see V.5) is replaced by other ω-aminocarboxylic acids (n. represents the numbers of carbon atoms and m represents the number of nitrogen atoms).

G. Synthesis of ANPAPDP

Cystine (96 mg) self dissolved in 0.9 ml of 0.1 M NaOH, is allowed to react with 4-azido-1-fluoro-2-nitro-benzene (182 mg) taken in 900 μl dioxane. Following reaction for 24 h at 55° C., the mixture is evaporated and the residue is extracted with ether to remove excess 4-azido-1-fluoro-2-nitro-benzene. After the crude product is purified by column chromatography on silica, the product is reduced with tri-n-butylphosphine in methanol for 30 min prior to addition of 2,2'-dithiopyridine. The crude product is purified by column chromatography on silica.

Analogues of 2-(N-(4-azido-2-nitrophenyl)amino)-3-(2-pyridyldithio)propionic acid (ANPAPDP) are easily synthesized by replacing cystine with small polyamides such as cystinyl-di(3-aminopropionic acid).

H. Synthesis of ANPAPDP-NADP

ANPAPDP (37.5 mg) is activated with carbonyldiimidazole (81 mg) in dry dimethylformamide (0.5 ml) for 15 min prior to addition of 0.5 ml water containing 16 mg $NADP^+$. After stirring for overnight, the product is purified by reverse phase chromatography.

Figure 7:
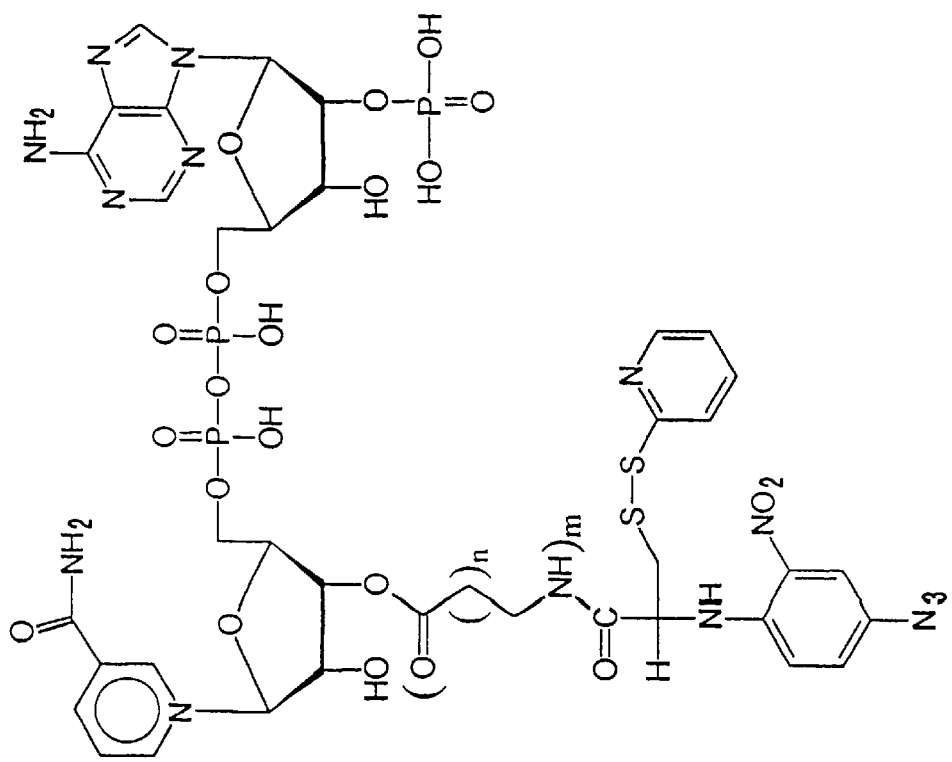
FIG. 7 gives the structure of ANPAPDP-NADP. (The "n" indicates the number of carbon atoms, and the "m" indicates the number of nitrogen atoms.)

The structure of N3-O-[2-(N-(4-azido-2-nitrophnyl)-amino)-3-(2-pyridyldithio)propionyl]-NADP (ANPAPDP-NADP) is shown in FIG. 7 (n represents the number of carbon atoms, m represents the number of nitrogen atoms).

I. Synthesis of 4-Azido-2,3,5,6-Tetraflurobenzioc Acid Hydrazide (ATFBH)

4-Azido-2,3,5,6-tetrafluorobenzioic acid (25 mg) is activated with equimolar amounts of N-hydroxy succinimide and a 20% molar excess of dicyclohexylcarbodiimide in tetrahydrofuran. The resulting ester is treated with an equimolar amount of hydrazine for the formation of hydrazide.

J. Synthesis of NADP N2',N3'-DIAL-(4-2,3,5,6-Tetrafluorobenzioic Acid Hydrazone)

Figure 8:
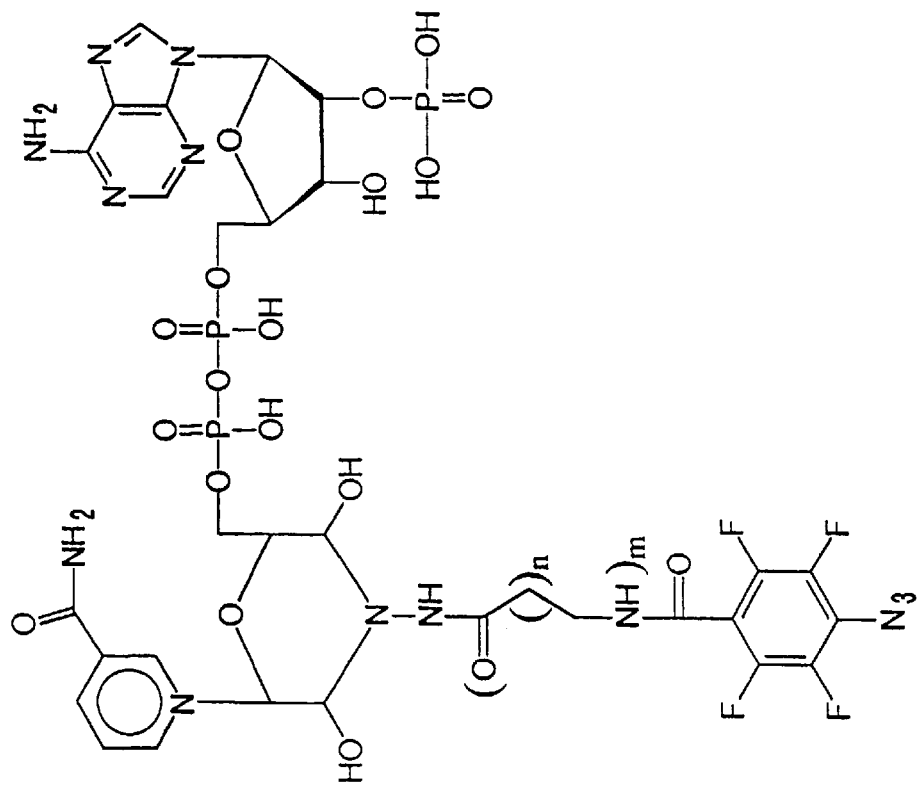
FIG. 8 gives the structure of NADP N2',N3'-DIAL (4-AZIDO-2,3,5,6-TETRAFLUOROBENZOIC ACID HYDRAZONE). (The "n" indicates the number of carbon atoms, and the "m" indicates the number of nitrogen atoms.)

Twenty milligrams of N2',N3'-NADP-dialydehyde (prepared by mild periodate oxidation) is reacted with an equimolar amount of ATFBH. The product is isolated by reverse phase chromatography. The structure of this NADP derivative is shown in FIG. 8 (n represents the number of carbon atoms, m represents the number of nitrogen atoms).

K. Synthesis of NADP[2'S'α,S]

2'3-O-isopropylidene-nicotinamide is synthesized by shaking a solution of nicotinamide mononucleotide (25 mg) for three hours in a HCl-saturated mixture of 2,2-dimethyoxypropane and dioxane. Following evaporation of the solvent, tri-n-octylamine and pyridine are added and the solution is evaporated. Addition of pyridine is followed by mixing with an equimolar amount of 5'(α-thio)AMP, previously activated with diphenylphosphorochloridate in N-methylpyrrolidone. The solution is evaporated after 4 days and the protecting group is removed with 1M hydrochloric acid. The product is purified by ion exchange chromatography. The α-thio-NADP is phosphorylated with NAD-kinase in the presence of ATP.

Figure 9:
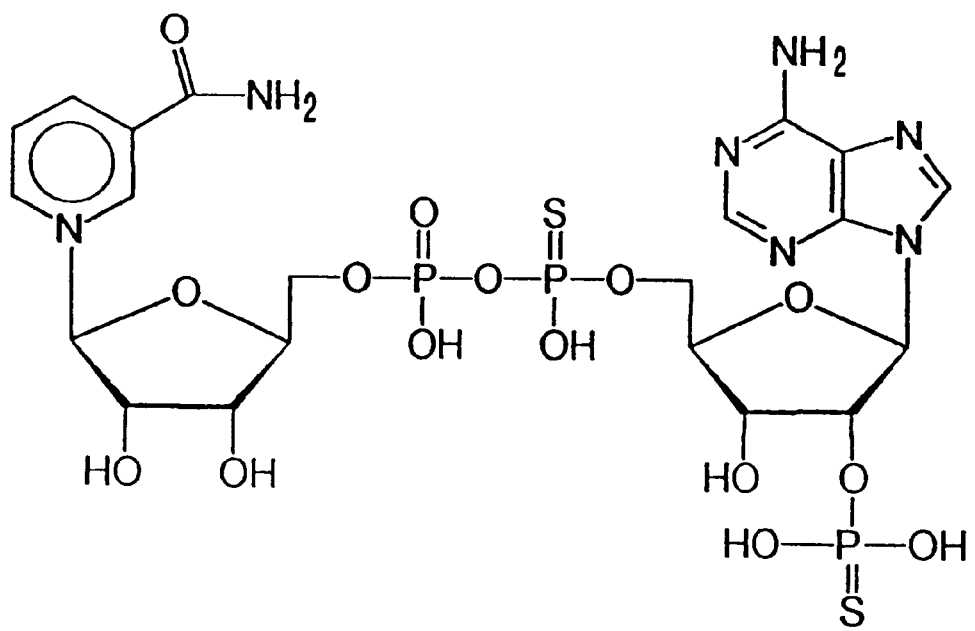
FIG. 9 gives the structure of (NADP [2'-S,α-S].

The structure of adenosine-2'-thiophospho-5'(α-thiodiphospho-5'ribofuranosyl-nicotinamide (NADP[2'-S, α-S]) is shown in FIG. 9.

L. Synthesis of ANPAEP-2'-AMP

4-Azido-1-fluoro-2-nitro-benzene (91 mg) is heated for 24 hrs at 55° C. in a 3 ml solution containing 2-aminoethanol and ethanol at a 1:1 ratio. After evaporation, the crude product is purified by column chromatography on silica. The H-phosphonate, formed by reaction with $PCl_3$, is activated with pivaloylchloride prior to coupling with 2'-AMP. Following oxidation with iodine/water, the resulting phosphate is purified by ion-exchange chromatography.

Instead of 2-aminoethanol, any ω-aminoalcohol can be used, e.g. 4-aminobutanol or 6-aminohexanol.

Figure 10:
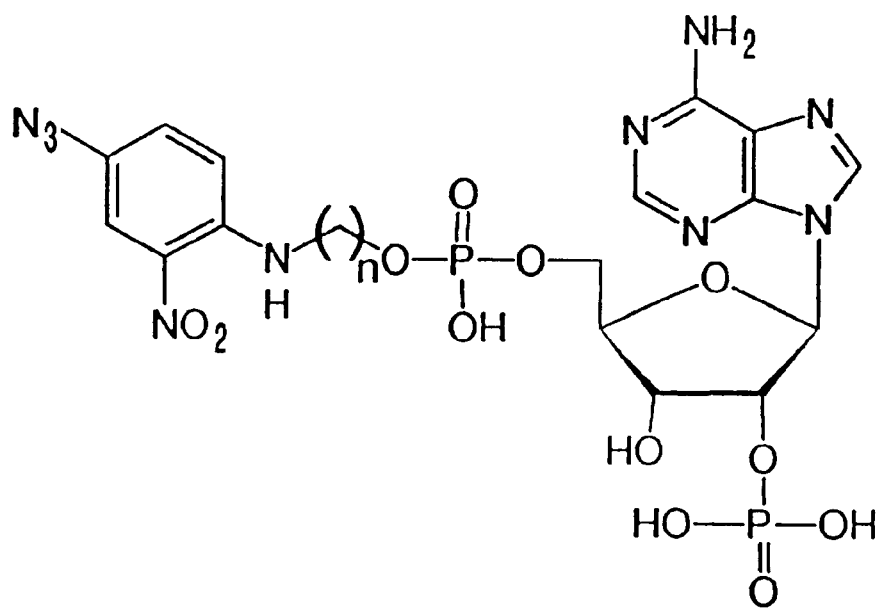
FIG. 10 gives the structure of ANPAEP-2'-AMP.

The structure of 5'-O-[2-(N-(4-azido-2-nitrophenylamino) thylphosphate]2;-AMP (ANPAEP-2'-AMP) is shown in FIG. 10 (n represents the number of carbon atoms).

EXAMPLE 15

Non-Covalent Binding of NADP(H)-Derived Ligands to the Affinity Component

Figure 11:
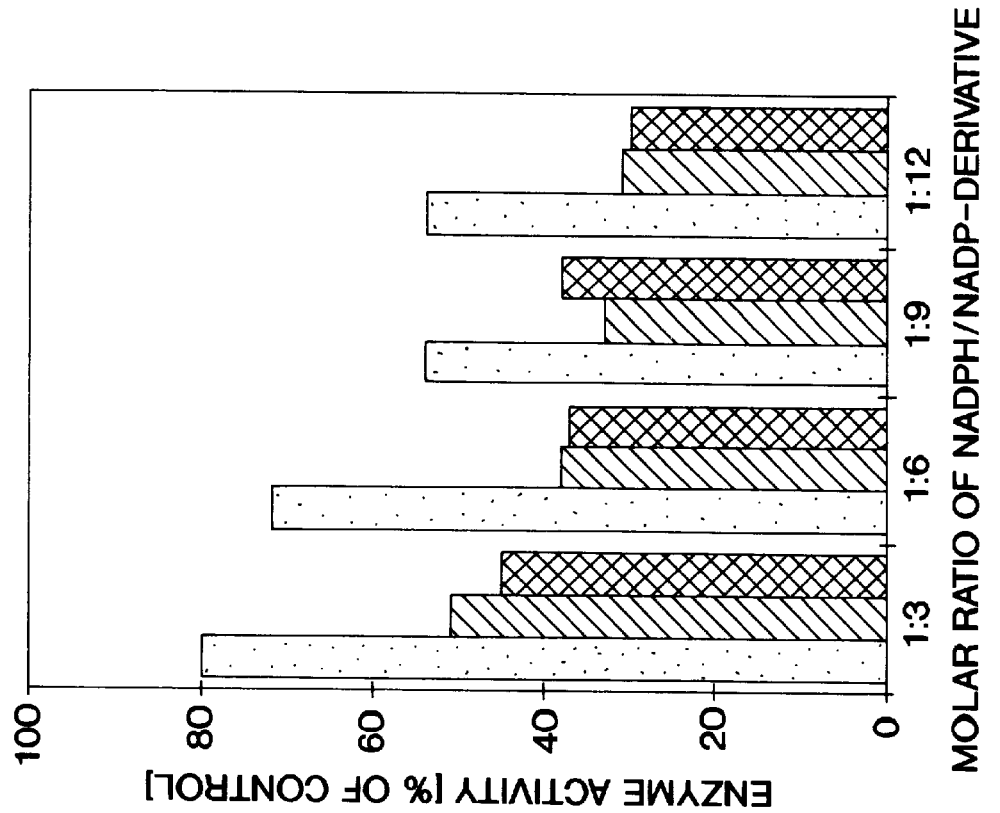
FIG. 11 shows the inhibition of the catalytic activity of the affinity component by (NADPH)-DERIVED LIGANDS. The dotted bars refer to ANPAP-NADP, the hatched bars refer to NADP, and the crosshatched bars refer to 8-$N_3$NADP.

A. Inhibition of the Catalytic Activity of the Affinity Component by NADP(H)-Derived Ligands The activity of the affinity component is assayed in the absence (control) and presence of 3-to 12-fold molar excess of $NADP^+$, $8-N_3-NADP^+$ or $ANPAP-NADP^+$ over NADPH concentration (as described in Example 11.). FIG. 11 shows the inhibitory activity of NADP(H)-derived ligands on the catalytic activity of the affinity component.

B. Coenzymatic Activity of NADPH-Derived Ligands

Figure 12:
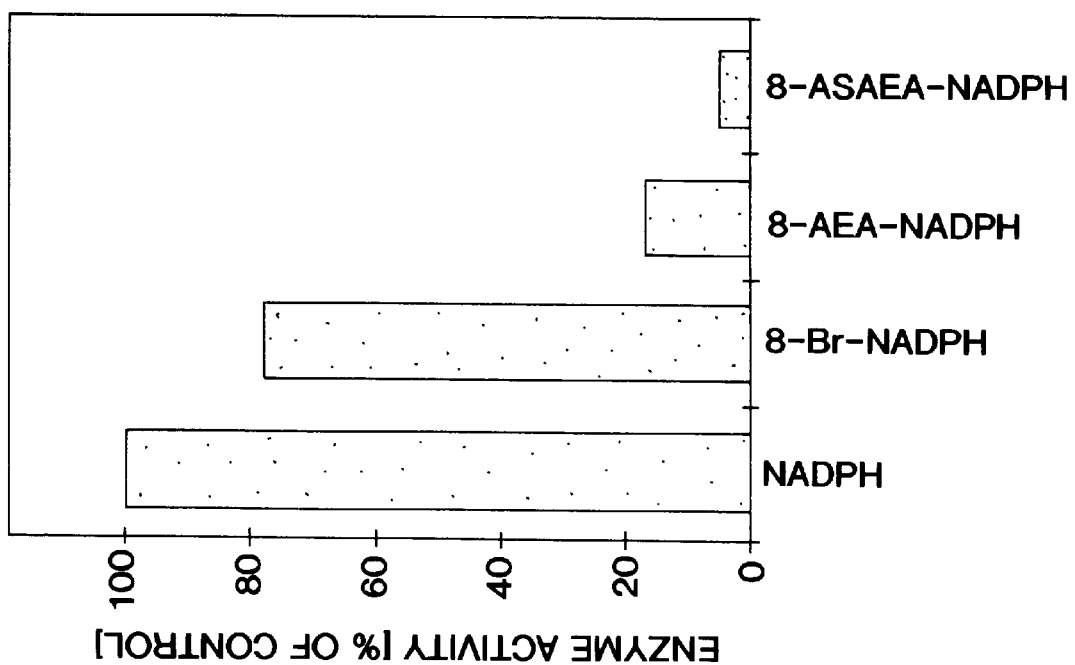
FIG. 12 shows the coenzymatic activity of NADPH-derived ligands.

The coenzymatic activity of 8-Br-NADPH, 8-AEA-NADPH and 8-ASAEA-NADPH is determined by substituting NADPH with the derivatives in the activity assay as described in Example 11. FIG. 12 shows the coenzymatic activity of NADPH-derived ligands.

Figure 13:
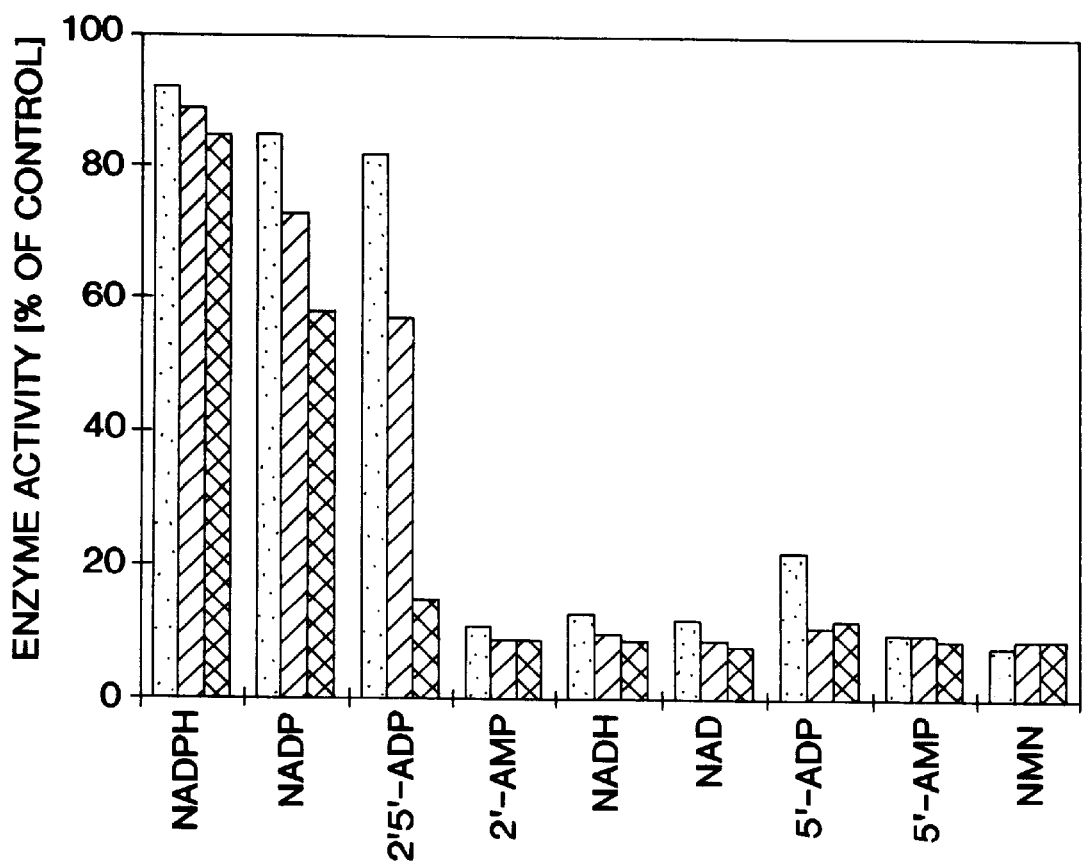
FIG. 13 shows the thermo-stabilization of the affinity component by non-covalent binding of NADP(H) and NADP(H)-derived moieties. The dotted bars refer are 1 mM, the hatched bars are 100 uM, and the cross hatched bars are 10 uM.

C. Thermo-stabilization of the Affinity Component by Non-covalent Binding of NADP(H) and NADP(H)-Derived Ligands Three different concentrations of various NADP(H)-derived moieties (final concentrations: 10, 100 and 1000 μM) are added td the incubation mixture containing 0.005 mg of the affinity component in a total volume of 0.025 ml of 10 mM phosphate buffered saline, pH 7.2. Following incubation at 37° C. for 30 min., the catalytic activity of the affinity component is assayed as described in see Example 11. FIG. 13 shows the effect of non-covalent binding of NADP(H) and various NADP(H)-derived moieties on the thermo-stability of the affinity component.

D. Thermo-stabilization of the Affinity Component by Non-covalent Binding of Azido-derivatives of NADP(H)

Figure 14:
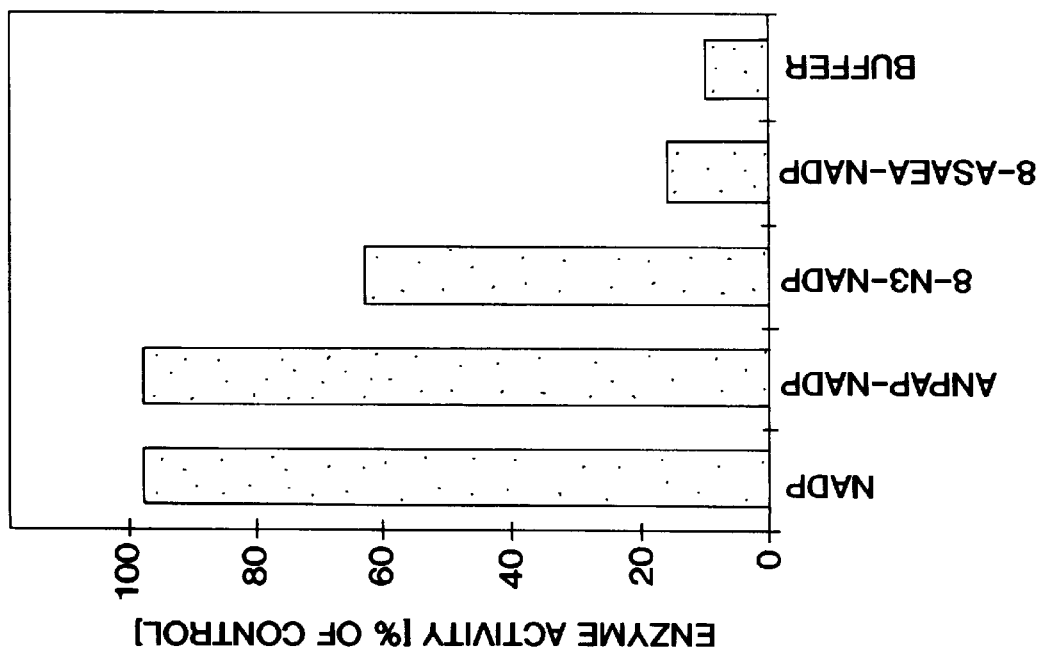
FIG. 14 shows the thermo-stabilization of the affinity component by non-covalent binding of azido-derivatives of NADP(H).

The affinity component (0.005 mg) is incubated at 37° C. in the presence of 5 nmol of azido-derivatives of NADP(H) in a total volume of 0.025 ml of phosphate-buffered saline, pH 7.2. Following incubation for 30 min, the affinity component is assayed as described in Example 11. FIG. 14 shows the effect of non-covalent binding of azido-derivatives of NADP(H) on the thermo-stability of the affinity component.

EXAMPLE 16
Covalent Binding of Azido-Derivatives of NADP(H) to the Affinity Component A. Covalent Binding of Azido-derivatives of NADP(H) to the Affinity Component by Photolysis A 5–50 fold molar excess of the azido-derivatives of NADP(H) is added to the affinity component and the volume is adjusted with 10 Mm Tris-Hcl (Ph 7.5) to a final protein concentration of 1.0 mg/ml. The reaction mixture, in a Reacti-Vial, is placed at a distance of 12 cm from a light source (600 W, DVY, 1200 K°). During photolysis (5–12.5 min) the reaction mixture is kept on ice with continuous stirring. Following photolysis, the reaction mixture is subjected to size exclusion chromatography on Sephadex G-25 equilibrated with PBS. Fractions containing catalytic activity are pooled and concentrated using a SpeedVac concentrator.

Figure 15:
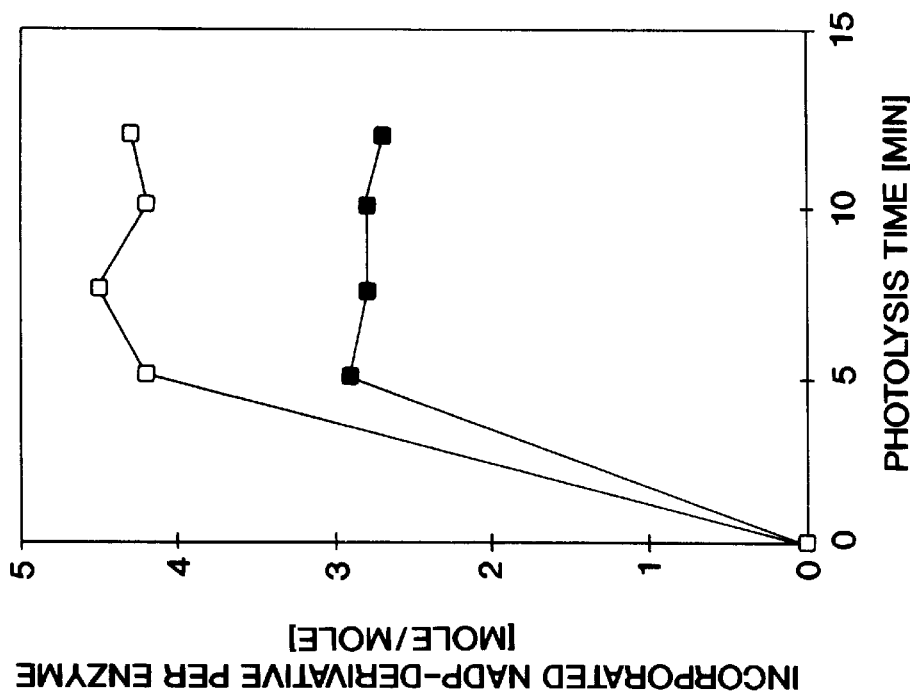
FIG. 15 shows covalent binding of azido-derivatives of NADP to the affinity component as a function of photolysis time. The empty square refers to 8-$N_3$NADP, and the filled square refers to ANPAP-NADP.
Figure 16:
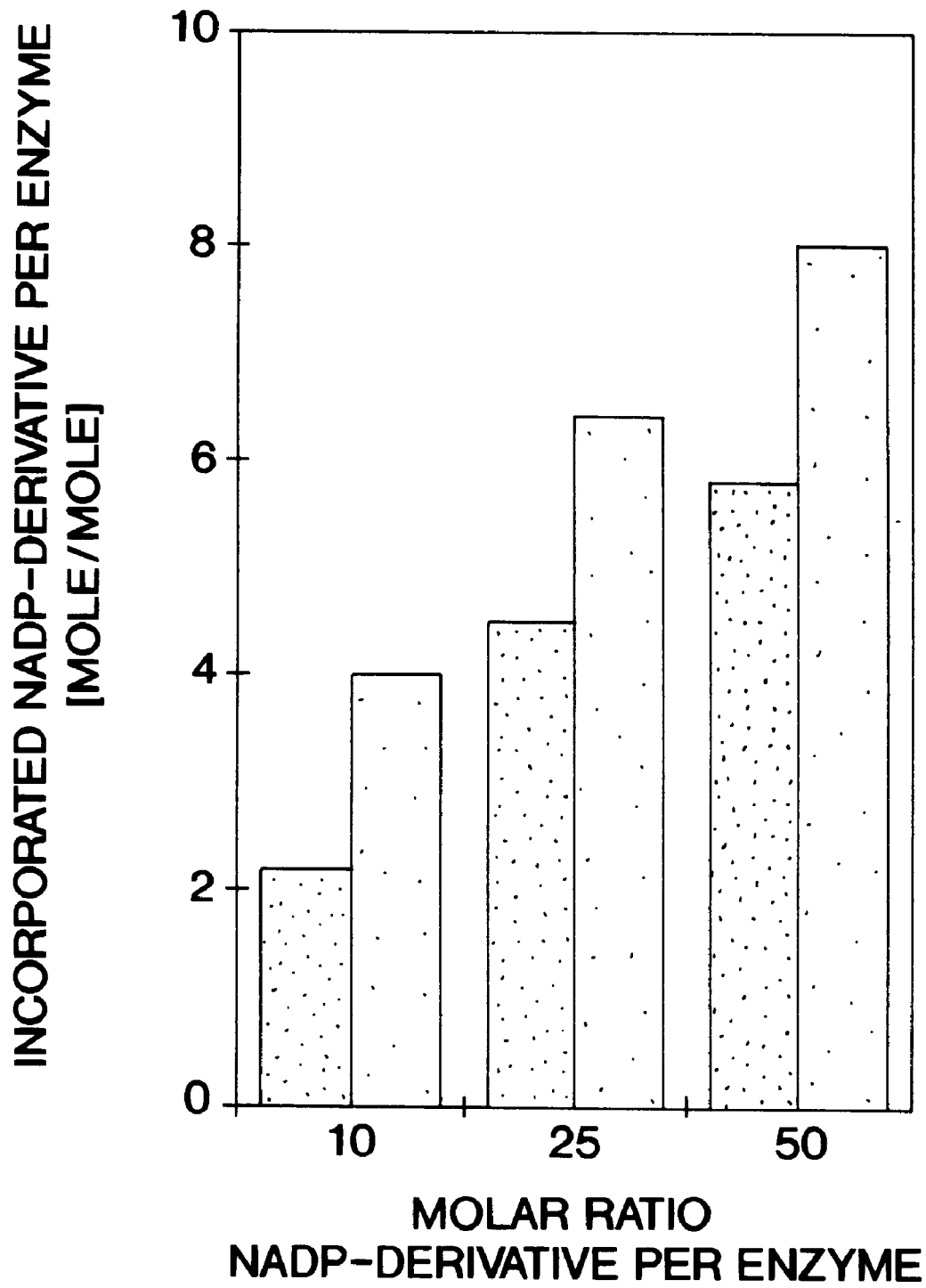
FIG. 16 shows covalent binding of azido-derivatives of NADP to the affinity component using different concentrations of the derivatives. The darkly shaded bars refer to ANPAP-NADP, and the lightly shaded bars refer to 8$N_3$NADP.

The number of azido-derivatives of NADP(H) incorporated per molecule of the affinity component is determined from the absorbance at 260 nm and the protein concentration of the derivatized affinity component. Molar extinction coefficients of the NADP(H)-derivatives at 260 nm used are $18.0 \times 10^3$ $M^{-1} cm^{-3}$ and $45.4 \times 10^3$ $M^{-1}$ $cm^{-1}$ for 8-$N_3$-NADP$^+$ and ANPAP-NADP$^+$ respectively. Protein concentrations are determined by bicinchoninic acid method (Smith, P. K., Krohn, R. I., Hermanson, G. T., Mallia, A. K., Gartner, F. H., Provenzano, M. D., Fujimoto, E. K., Goeke, N. M., Olson, B. J., and Keenk, D. C. Anal. Biochem. 150:76–85, 1985) using bovine serum albumin as standard. FIG. 15 shows the extent of covalent binding of ANPAP-NADP and 8-$N_3$-NADP to the affinity component as a function of photolysis time. FIG. 16 shows the extent of covalent binding of ANPAP-NADP and 8-$N_3$-NADP to the affinity component using different concentrations of the azido-derivatives of NADP.

Figure 17B:
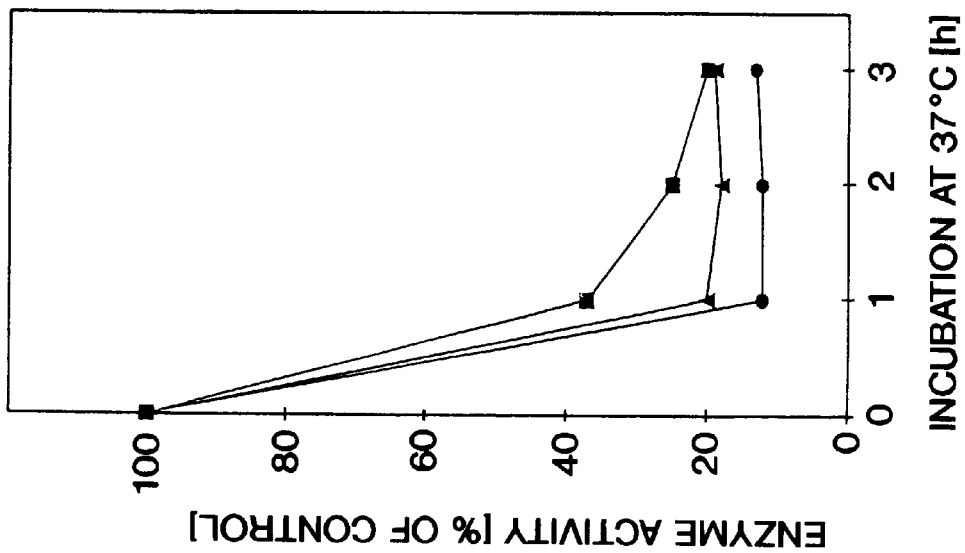
FIG. 17B refers to the affinity component derivatized with 8$N_3$NADP.
Figure 17A:
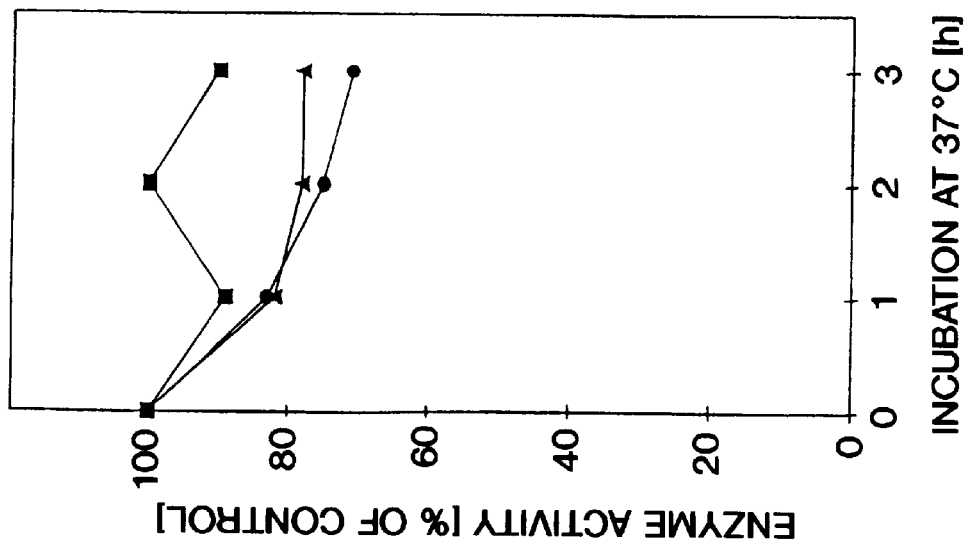
FIG. 17A refers to the affinity component derivatized with ANPAP-NADP.

B. Thermo-Stability of the Affinity Component Covalently Derivatized with Azido-Derivatives of NADP: Determiniation of its Catalytic Activity The affinity component, covalently linked to different amounts of azido-derivatives of NADP$^+$ (2.4 to 5.8 ANPAP-NADP$^+$ or 4.2 to 8.0 8-$N_3$-NADP$^+$) is incubated at 37° C. in PBS. An aliquot is withdrawn at each hour of incubation and is frozen immediately. The catalytic activity of the affinity component is assayed as described in Example 11. FIG. 17 shows the thermo-stability of the affinity component covalently derivatized with ANPAP-NADP$^+$ or 8-$N_3$-NADP$^+$, as determined by its remaining catalytic activity.

Figure 18C:
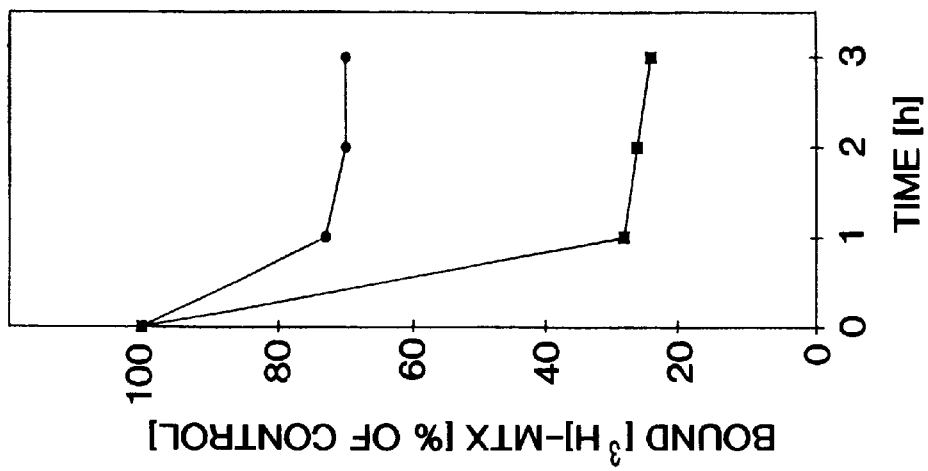
In FIG. 18C, the amount of bound MTX was calculated from the void volume of each SEPHADEX G-25 fractionation. The filled squares refer to kept in ice, the diamonds refer to incubation at 37° C. for 1 hour, the circles refer to incubation at 37° C. for 2 hours, and the triangles refer to incubation at 37° C. for 3 hours.
Figure 18B:
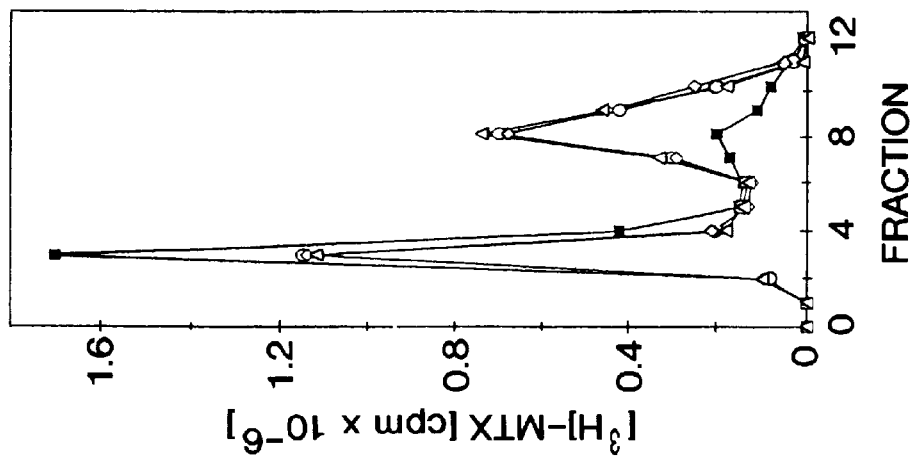
FIG. 18B refers to the affinity component derivatized with ANPAP-NADP.
Figure 18A:
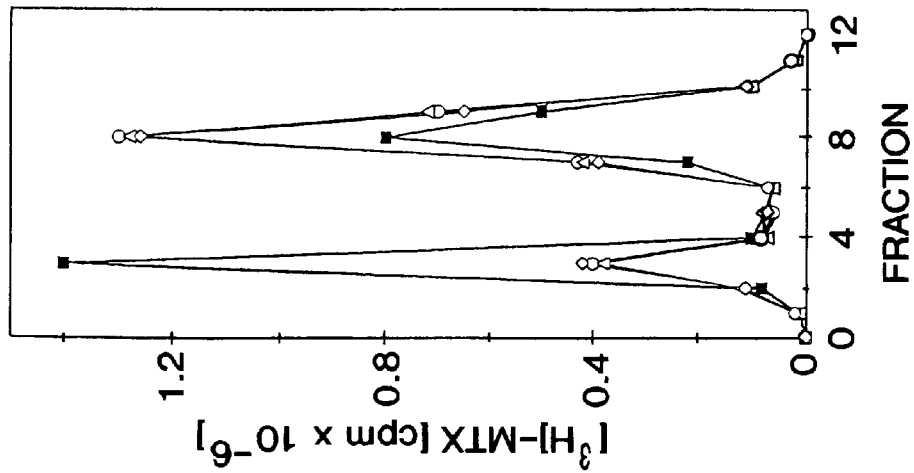
FIG. 18A shows the affinity component derivatized with 8$N_3$NADP.

C. Thermo-Stability of the Affinity Component Covalently Derivatized with Azido-Derivatives of NADP: Determination of its Binding Activity The affinity component covalently linked to 8-$N_3$-NADP$^+$ (4.0 molecules per molecule of affinity component) or ANPAP-NADP$^+$ (2.4 molecules per molecule of affinity component) is incubated at 37° C. in PBS. An aliquot (0.01 ml; 0.476 nmol) is withdrawn after each hour of incubation and is assayed for binding (as described in Example 11) with 0.01 ml of the [$^3$H]-labeled binding partner (0.46 n mole). The binding activity of the affinity component with its binding partner is determined from the radioactive counts in the void volume. A control experiment is performed in each case with the derivatized affinity component incubated at 4° C. FIG. 18 shows the thermo-stability of the affinity component covalently derivatized with ANPAP-NADP$^+$ or 8-$N_3$-NADP$^+$ as determined by its remaining [$^3$H] MTX binding activity.

EXAMPLE 17
Synthesis of Folate-Derived Ligands

A. Synthesis of the α,γ-Dicarboxylethylester Derivative of MTX

Figure 19:
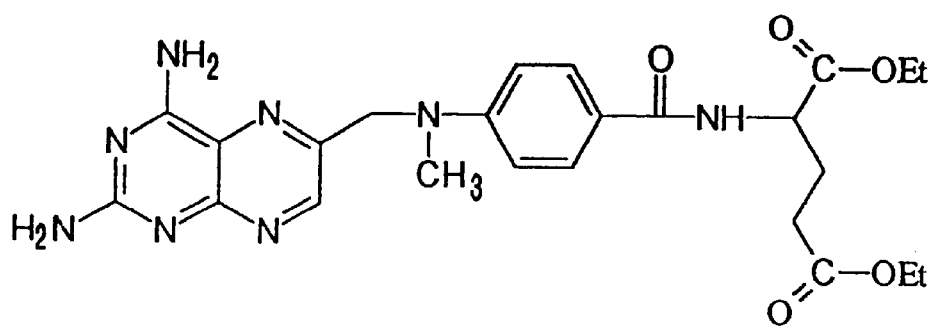
FIG. 19 gives the structure of the α, γ-Dicarboxyl ethyl ester of MTX.

MTX (100 mg) is stirred with 5 ml of ethanol saturated with HCl to form the corresponding diethylester derivative. Once the suspension is clear, the solvent is evaporated and the crude product is extracted twice with ethanol to remove the Hcl. Other alcohols like 1-butanol or 1-hexanol can also be used to obtain long chain ester derivative. FIG. 19 shows the structure of the α,γ-dicarboxylethylester derivative of MTX.

B. Synthesis of the α,γ-Dicarboxylhydrazide Derivative of MTX

Figure 20:
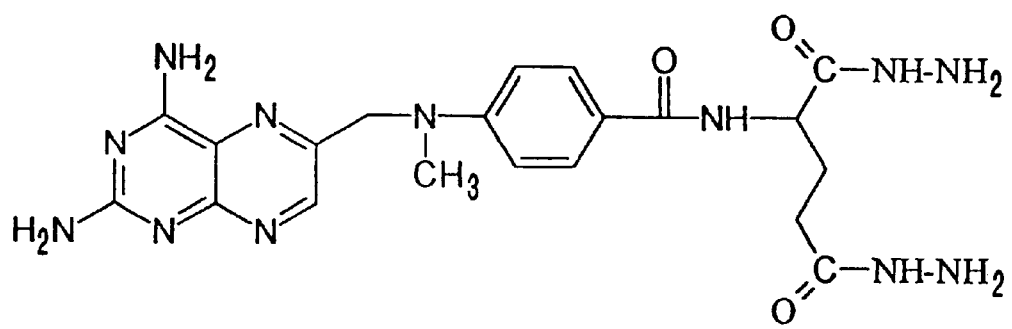
FIG. 20 gives the structure of the α, γ-Dicarboxyl hydrazide derivative of MTX.

To a solution of MTX diethylester (40 mg) in ethanol, 0.05 ml of hydrazine is added and the mixture is stirred for 12 hours. Following removal of the solvent, the compound is dissolved twice in ethanol and evaporated. FIG. 20 shows the structure of the α,γ-dicarboxylhydrazide derivative of MTX.

C. Synthesis of the α,γ-Dicarboxylamidomethane/sulfonic Acid Derivative of MTX

Figure 21:
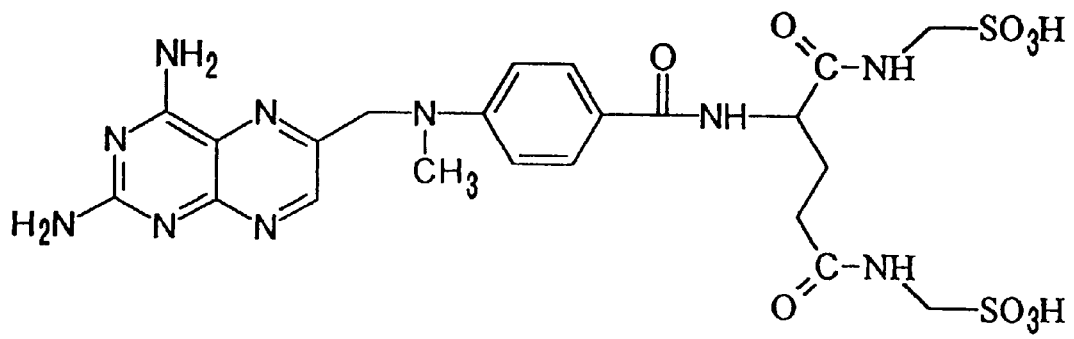
FIG. 21 gives the structure of the α, γ-Dicarboxyl aminomethane sulfonic acid derivative of MTX.

An excess of carbonyldiimidalzole is added to 3 ml of dimethylformamide (DMF) containing 50 mg of MTX. The mixture is stirred for 15 min before 20 mg of aminomethane sulfonic acid is added and the stirring is continued for four days. After evaporation of the solvent, the crude product can be purified by column chromatography on silica. FIG. 21 shows the structure of the α,γ-dicarboxyl-amidomethanesulfonic acid derivative of MTX.

Figure 22:
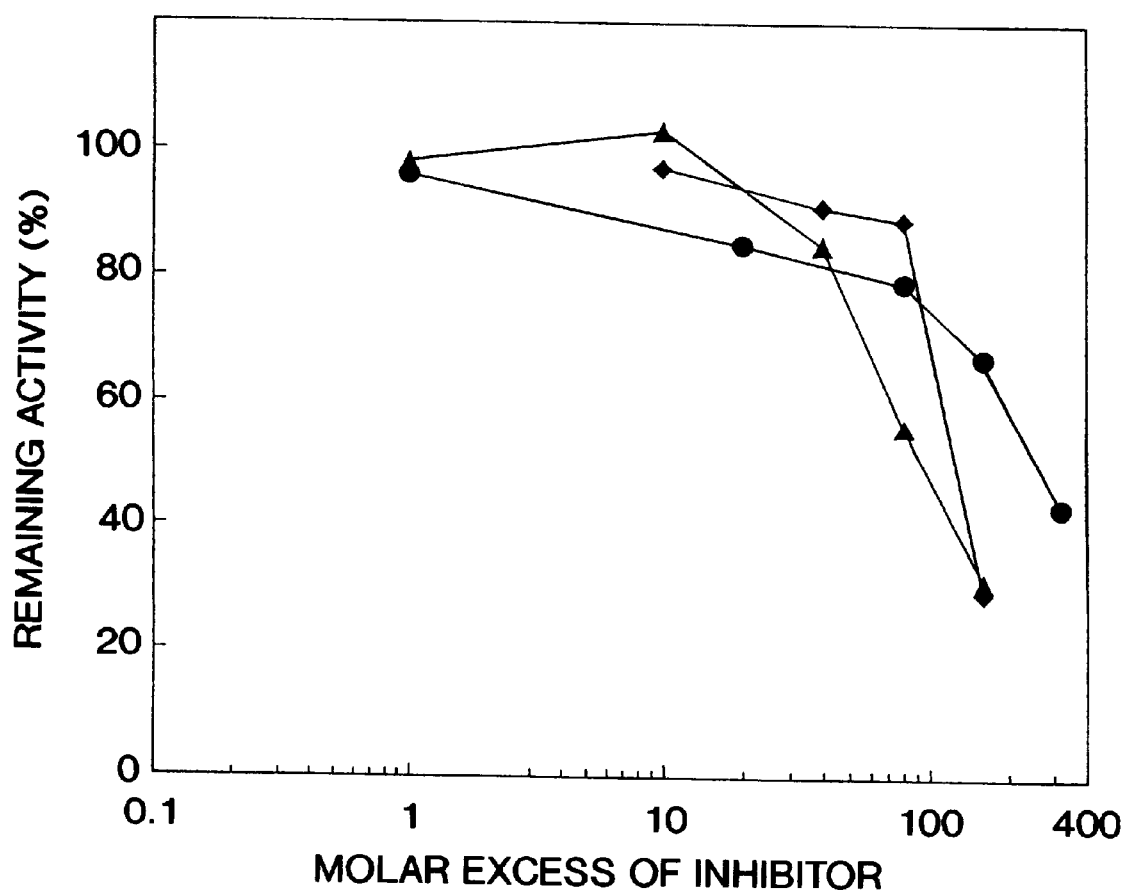
FIG. 22 shows the inhibition of catalytic activity of the affinity component by MTX derivatives. The diamond refers to dihydrazide derivative of MTX, the circle refers to diethylester derivative of MTX, and the triangle refers to diaminomethane sulfonic acid derivative of MTX.

EXAMPLE 18
Non-covalent Binding of MTX Derivatives to the Affinity Component A. Inhibition of the Catalytic Activity of the Affinity Component by MTX Derivatives The MTX derivatives (10–360 fold molar excess over the affinity component) are added to the reaction mixture containing the affinity component, NADPH, and dihydrofolate at concentrations as described in Example 11. The inhibition of the catalytic activity of the affinity component is determined by assaying the affinity component in the absence of any derivative. FIG. 22 shows the inhibitory effect of three α,γ-dicarboxyl derivatives of MTX (diethylester derivative, diamino derivative, and dihydrazide derivative) on the catalytic activity of the affinity component.

Figure 23A:
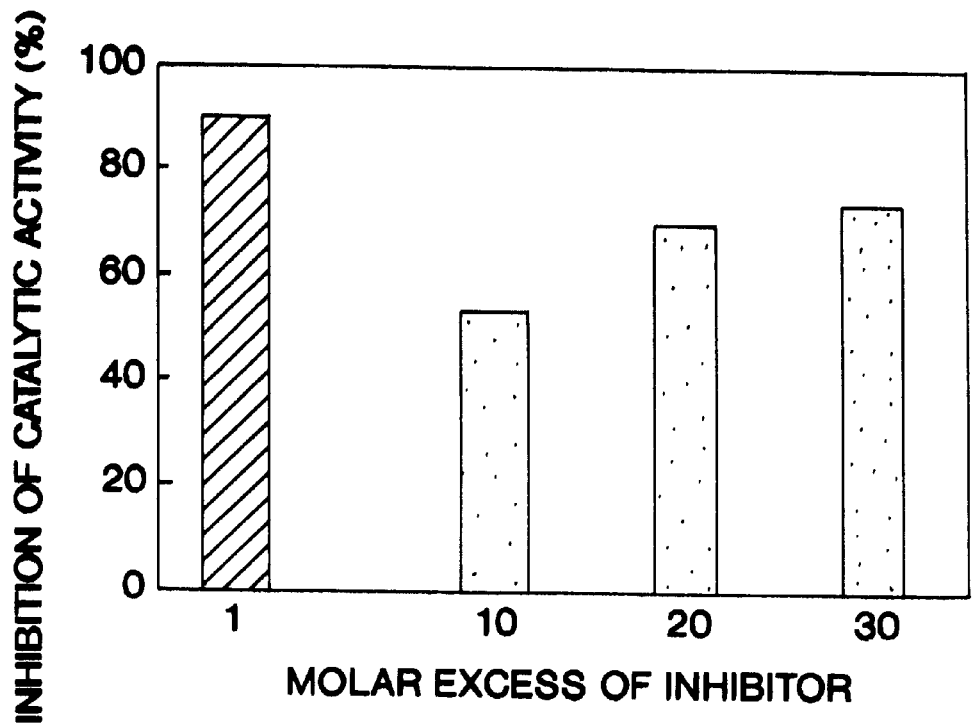
FIGS. 23 (A and B) show the inhibition of the binding and catalytic activities of the affinity component by MTX and its diamido methane sulfonic acid derivative. The dotted bars refer to derivative, and the hatched bars refer to MTX.
Figure 23B:
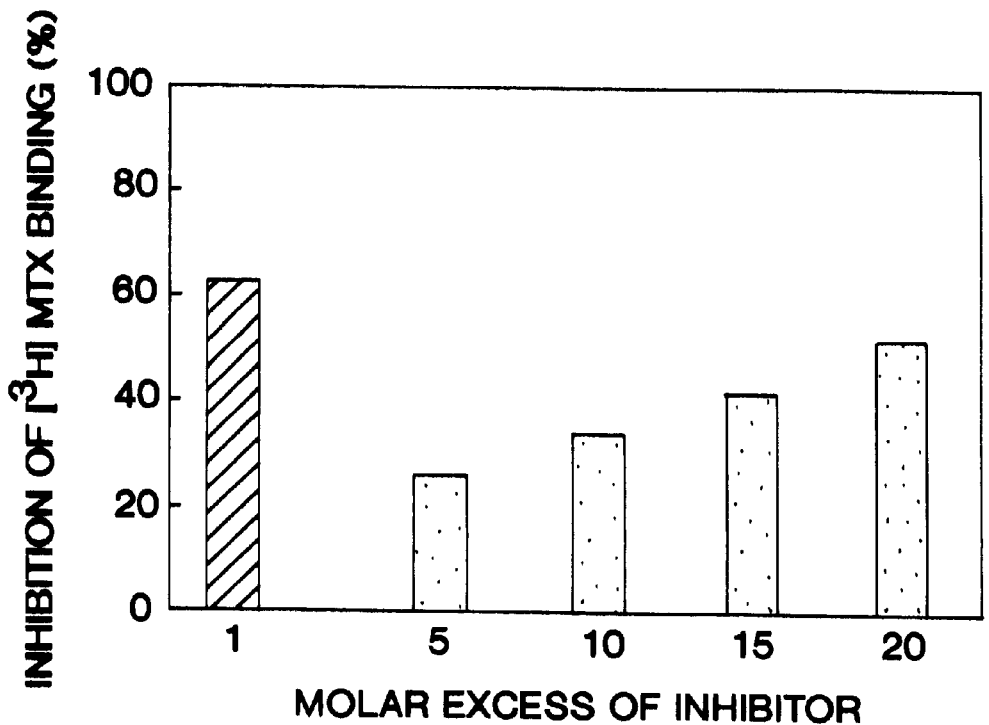

B. Inhibition of the Binding and Catalytic Activities of the Affinity Component by MTX and its Diaminomethane-sulfonic Acid Derivative The binding activity of the affinity component to its [$^3$H]-labeled binding partner is determined in the presence of a 5- to 20-fold molar excess of the diaminomethanesulfonic acid derivative of MTX. The reaction mixture contains an equimolar concentrations (0.076 nmol) of the affinity component, its [$^3$H]-labeled binding partner, and the MTX derivative in a total volume of 0.1 ml. The reaction mixture is kept at room temperature for 1.5 hrs, followed by gel filtration on Sephadex G-25 (bed volume: 1 ml). The inhibition of binding activity is determined from the control experiment where the binding study is carried out without the derivative. FIG. 23 compares the inhibitory effect of non-derivatized MTX and the α,γ-dicarboxylamidomethanesulfonic acid derivative of MTX on both the binding and the catalytic activities of the affinity component.

Figure 24:
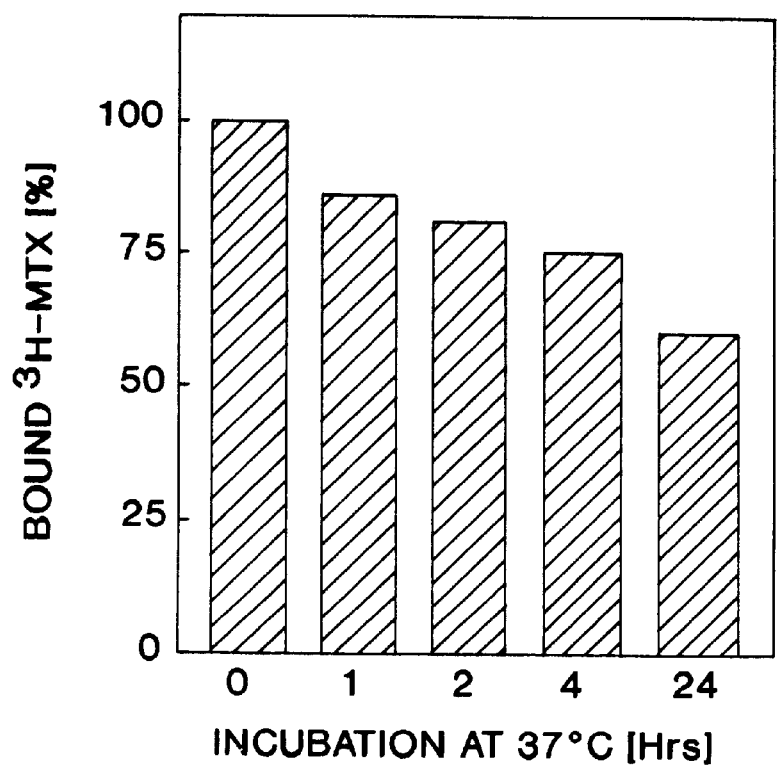
FIG. 24 shows the thermo-stabilization effect of MTX on the affinity component in buffer.

C. Thermo-stabilizing Effect of MTX on the Affinity Component in Phosphate Buffered Saline Equimolar amounts of the affinity component and its [$^3$H]-labeled binding partner are incubated in 0.02 ml of 10 mM Tris-HCl (pH 7.5) for 1 hr at room temperature. Following removal of unbound [$^3$H]-labeled binding partner by gel exclusion chromatography on Sephadex G-25, the fractions in the void volume containing radioactive counts are concentrated. An aliquot of the concentrated fractions is then incubated at 37° C. in PBS for 24 hrs. The remaining radioactivity associated with the affinity component is determined from the counts in the void volume using a second gel filtration on Sephadex G-25. FIG. 24 shows the thermo-stabilizing effect of MTX on the affinity component in PBS.

Figure 25:
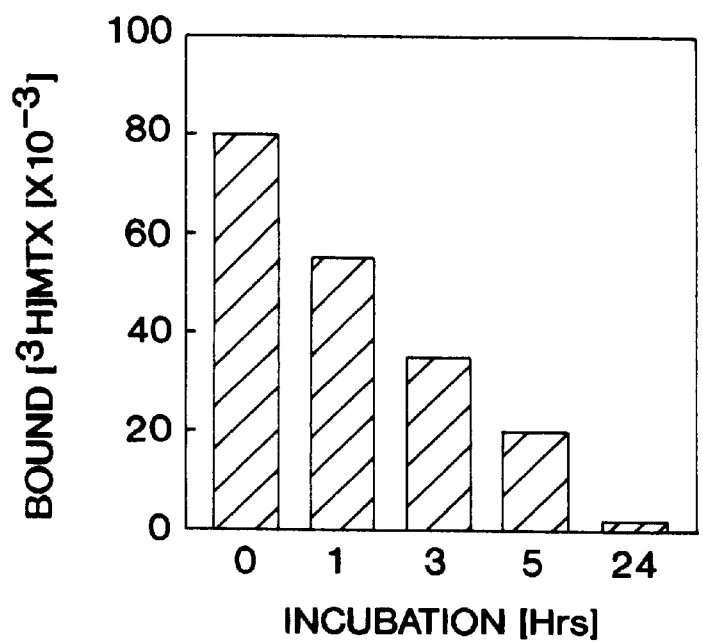
FIG. 25 shows the thermo-stabilization effect of MTX on the affinity component in normal human serum.

D. Thermo-stabilizing Effect of MTX on the Affinity Component in Normal Human Serum Equimolar amounts of the affinity component and its [$^3$H]-labeled binding partner are incubated in 0.02 ml of 10 mM Tris-HCl (pH 7.5) for 1 hr at room temperature. Following removal of unbound [$^3$H]-labeled binding partner by gel exclusion chromatography on Sephadex G-25, the fractions in the void volume containing radioactive counts are concentrated. An aliquot of the concentrated fractions is then incubated at 37° C. in presence of normal human serum (NHS) (final concentration: 50%) for 24 hrs. The remaining radioactivity associated with the affinity component is determined from the counts in the void volume of a gel filtration column on Sephadex G-25. FIG. 25 shows the thermo-stabilizing effect of MTX on the affinity component in normal human serum.

E. Effect of Different MTX Concentrations on the Thermo-Stability of the Affinity Component in Normal Human Serum Methotrexate is added at different concentrations to the reaction mixture containing 0.761 n mole of the affinity component in 0.05 ml of serum and 10 mM PBS (pH 7.2) in a total volume of 0.1. Following incubation at 37° C. for 24 hrs, the non-bound binding partner is removed by gel exclusion chromatography as described in Example 11. The fractions in the void volume are collected and concentrated. The [$^3$H]-labeled binding partner (0.8 nmol) is added to the concentrated affinity component, and the volume adjusted with water to 0.1 ml. After incubation at room temperature for 1.5 hrs, the binding activity of the affinity component is determined by a gel filtration on Sephadex G-25 as described in Example 11. FIG. 26 shows the thermo-stabilizing effect of different MTX concentrations on the affinity component in normal human serum.

EXAMPLE 19

Figure 27:
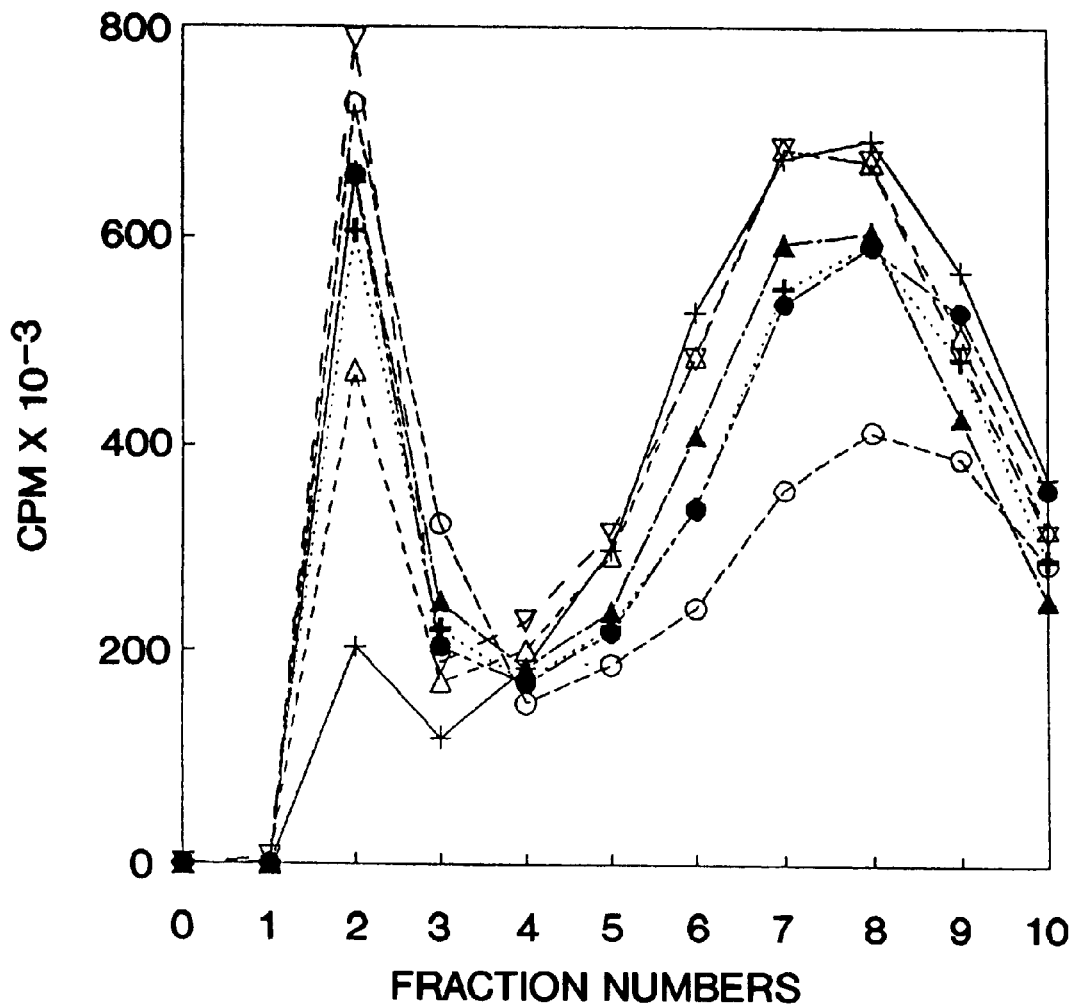
FIG. 27 shows the thermo-stabilization of the affinity component by covalent binding of DIMETHYLPIMELIMIDATE (DMP) and non-covalent binding of MTX. The light cross refers to incubation in buffer at 37° C. without MTX; the dark cross refers to incubation in serum at 37° C. in the presence of 3-fold molar excess of MTX; the empty triangle refers to incubation in buffer at 37° C. in the presence of 1.2-fold molar excess of MTX; the filled triangle refers to incubation in serum at 37° C. in the presence of 6-fold molar excess of MTX; the empty circle refers to incubation in serum at 4° C. in the presence of 1.3-fold molar excess of MTX; the filled circle refers to incubation in serum at 37° C. in the presence of 9-fold molar excess of MTX; and the inverted triangle refers to incubation in buffer at 4° C.

Thermo-stabilization of the Affinity Component by a Combination of Crosslinking Reagents and Folate-Derived Ligands A. Thermo-stabilization of the Affinity Component by Covalent Binding of DMP and Non-covalent Binding of MTX The affinity component is modified with DMP as described in Example 12. An aliquot (0.075 ml) of the modified affinity component is mixed with an equal volume of either PBS or normal human serum, and the mixture is incubated at 37° C. After 24 hr, an aliquot (0.025 ml) is withdrawn from the reaction mixture and is immediately frozen until the binding assay of the affinity component is carried out as described in Example 11. FIG. 27 shows the thermo-stabilizing effect of covalently bound DMP and different concentrations of MTX on the affinity component in PBS and in human serum. FIG. 28 summarizes the results shown in FIG. 27.

EXAMPLE 20

Figure 29:
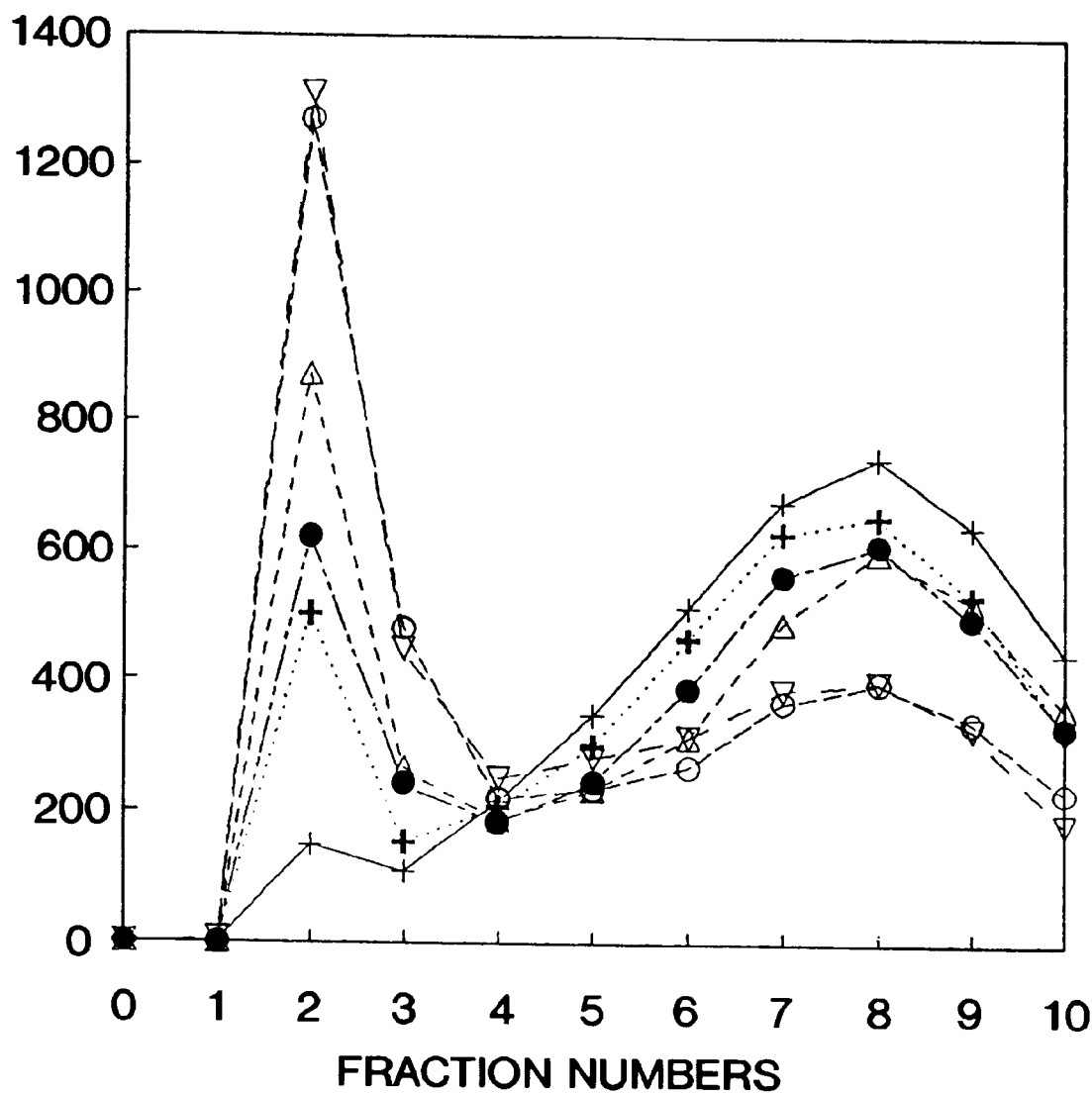
FIG. 29 shows the thermo-stabilization of the affinity component by covalent binding of ANPAP-NADP and non-covalent binding of MTX. The light cross refers to incubation in buffer at 37° C. without MTX; the dark cross refers to incubation in serum at 37° C. in the presence of 3-fold molar excess of MTX; the empty triangle refers to incubation in buffer at 37° C. in the presence of 1.2-fold molar excess of MTX; the filled triangle refers to incubation in serum at 37° C. in the presence of 6-fold molar excess of MTX; the empty circle refers to incubation in serum at 4° C. in the presence of 1.3-fold molar excess of MTX; the filled circle refers to incubation in serum at 37° C. in the presence of 9-fold molar excess of MTX; and the inverted triangle refers to incubation in buffer at 4° C.
Figure 32:
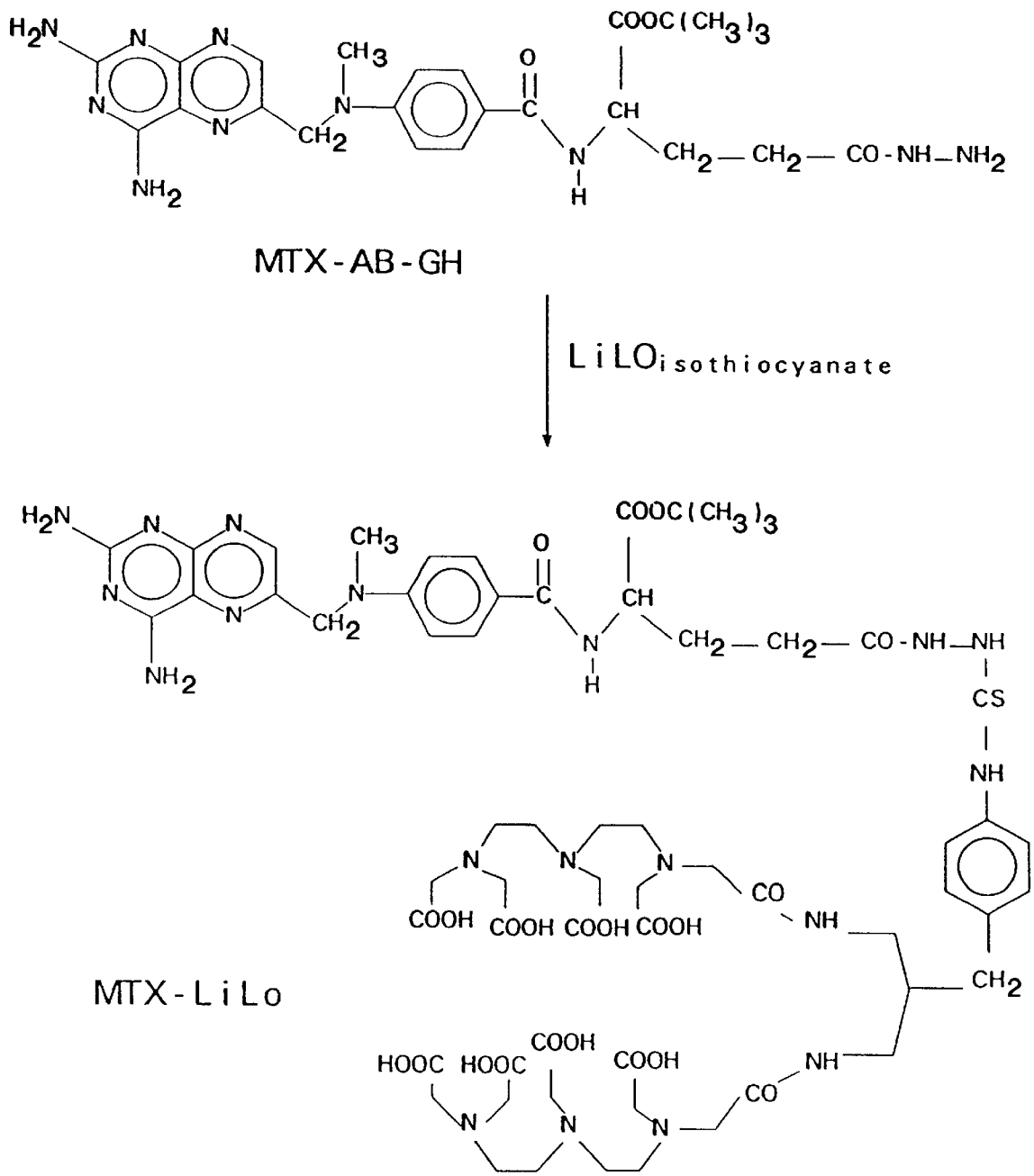
FIG. 32 is the scheme for the synthesis of MTX-LILO.

Thermo-Stabilization of the Affinity Component by a Combination of Covalently Bound NADP Derivatives and Non-Covalently Bound Folate-Derived Ligands A. Thermo-stabilization of the Affinity Component by Covalent Binding of ANPAP-NADP and Non-Covalent Binding of MTX ANPAP-NADP is covalently attached to the affinity component by photolysis as described in Example 16. The derivatized affinity component (0.7 nmol; 3.2 nmol NADP$^+$ derivative per mol affinity component) is incubated in presence of 0.05 ml normal human serum or PBS and a several fold (3–9) molar excess of its binding partner in a total volume of 0.1 ml. Following incubation at 37° C. for 24 hrs, the non-bound binding partner is removed by gel filtration chromatography as described in Example 11. The fractions in the void volume are concentrated and mixed with 0.8 nmol of the [$^3$H]-labeled binding partner. After adjusting the volume with water to 0.1 ml, the reaction mixture is incubated at room temperature for 1.5 hrs. The binding activity is determined from the radioactivity in the void volume of the second gel filtration column on Sephadex G-25 as described in Example 11. FIG. 29 shows the thermo-stabilizing effect of covalently bound ANPAP-NADP and different concentrations of MTX on the affinity component in PBS in normal human serum. FIG. 30 summarizes the results shown in FIG. 29.

EXAMPLE 21

Thermo-stabilization of the Affinity Component by Mutagenesis

A. PCR Cloning of Human DHFR

The cloning of the human DHFR is accomplished by isolation of total RNA from human hepatocyte HepG2.8 cells. cDNA is synthesized from 100 μg total RNA using the Gibco BRL CDNA synthesis system (LTI, Gaithersburg, Md.), according to the manufacturer's instructions. After purification by phenol extraction, chloroform extraction, and ethanol precipitation, cDNA is resuspended in 20 μl of distilled H$_2$O. A 4 μl aliquot is used for PCR cloning of human DHFR. The primer pair consists of a 5' oligonucleotide (5' GATCCCATGGTTGGTTCGCTAAACGT 3') containing an anchored NcoI site and codons encoding amino terminal amino acids 1 through 6 of rhDHFR and a 3' oligonucleotide (5' GATCCATGGCTATTAATCATTCT-TCTCATATAC 3') containing an anchored NcoI site, two translation termination codons and codons encoding the carboxy terminal amino acids 181–186 of rhDHFR. PCR is performed for 30 cycles of one minute at 94° C., one minute at 47° C., one minute at 72° C. The reaction mixture is loaded onto a 0.8% low melt agarose gel and a 600 bp fragment containing rhDHFR is excised and purified. An additional 30 cycles of amplification are performed with an aliquot of the gel purified rhDHFR fragment under the same conditions described except the annealing temperature is performed at 50° C. Following phenol extraction and purification via Amicon-100 filtration, the hDHFR fragment is digested with NcoI and ligated to the NcoI cleaved pET 11d cloning vector. Transformants of *E. coli* strain HB101 are screened with $^{32}$p labeled hDHFR fragment using standard methods. Positive clones are confirmed by digestion of mini-prep DNAs with NcoI.

B. Site-Directed Mutagenesis of rhDHFR: Introductior of a cysteine Residue at the LEU-133 Position The rhDHFR fragment is excised from pET lid via BglII and BamHI digestion and is ligated into BamHI cleaved pTZ19U. The Biorad Mutagene kit (BioRad, Hercules Calif.) is used to create specific amino acid alterations within the rhDHFR molecule. Single stranded DNA is prepared according to the manufacturer's instructions from the pTZ19U containing wild type rhDHFR in the *E. coli* dut ung strain CJ236, which results in incorporation of uracil residues on the wild type template. For the creation of a cysteine residue at amino acid Leu133 which is capable of disulfide bonding with the native cysteine at amino acid 6 of rhDHFR, an oligonucleotide 5' CCATCTTAAATGCTTTGTGAC 3' is annealed to the pTZ19U template, extended with T7 DNA polymerase and ligated with T4 DNA ligase according to the manufacturer's instructions. The ligated product is transformed into strain MV1190, whose active uracil-N-glycosylase inactivates the parental uracil containing strand, facilitating replication of the non-uracil containing mutant strand. Colonies containing the cysteine (TGC) at amino acid 133 are identified by Taq polymerase dideoxy nucleotide sequencing according to standard methodologies.

C. Site-Directed Mutagenesis of rhDHFR: Introduction of Two Cysteine Residues at the THR-39 and GLY-69 Positions For the introduction of two cysteine residues at the threonine 39 and glycine 69 positions. Single stranded pTZ19U DNA harboring the wild type DHFR insert is used as template for annealing with the oligonucleotide 5' GAAT-GACCTGCACCCTT 3' and extended, ligated and transformed as described in example XI.2. After identification of a bacterial transformant containing the TGC (cysteine) at amino acid 39, single stranded DNA is prepared from a single colony containing the cys 39 mutation and the oligonucleotide 5' CCTTTAAAGTGTAGAATTAATT 3' is used to create amino acid 69 cysteine (TGT) on the template which already contains the cysteine at residue 39.

D. Random Mutagenesis of rhDHFR

The wild type rhDHFR insert cloned in pET 11d is utilized in a PCR with the two 5' and 3' specific oligonucleotide primers listed in the Example 21. The modified PCR conditions include using 1.5 mM $MgCl_2$ in place of $MnCl_2$ and 2 μM dATP instead of 200 μm dATP. As a result, after 30 cycles of 94° C. for one minute, 47° C. for one minute and 72° C. for one minute, the polymerase chain reaction product contains a mixed population of molecules which harbor on the average 1.5% to 2% single point mutations scattered randomly throughout amino acids 7 through 181 of the human DHFR molecule. The mixed population is cloned into a phage vector system which harbors a restriction enzyme site for the introduction of peptides fused in frame to bacteriophage gene III protein (Smith, G. Science 228:1315–13137 (1985)). The $NH_2$ terminal gene III DHFR fusions, each containing various mutations, is expressed on the surface of the bacteriophage and is assayed for binding to its ligand by panning phage on a solid or semi-solid matrix containing the attached ligand.

E. Oxidation of rhDHFR Mutants Containing More Than One Cysteine Residue

In order to generate disulfide bonds within rhDHFR mutants containing more than one cysteine residue (see examples above), sodium tetrathionate is added at 20-fold molar excess to a solution containing 0.036 mg (1.7 nmol) of the mutated affinity component and 0.05 M sodium phosphate buffer, pH 6.5. Following reaction at 4° C. for 5 hrs, another 25-fold molar excess of sodium tetrathionate is added to the reaction mixture and the reaction is allowed to continue for another 24 hrs at 4° C. The modified affinity component is then purified by gel filtration on Sephadex G-25 (column volume: 1.0 ml) and fractions containing catalytic activity are pooled and concentrated in vacuo.

F. Derivatization of rhDHFR Mutants Containing More Than One Cysteine Residue with Sulfhydryl-Reactive Crosslinking Reagents A 5–10 fold molar excess of n-succinimidyl-(4-iodoacetyl)aminobenzoate (SIAB), is added to a solution containing 0.035 mg (1.67 nmol) of the mutated affinity component and 50 mM sodium borate buffer (pH 8.5). After 2 hrs at room temperature, excess reagent is removed by gel filtration using Sephadex G-25 (column volume: 1.0 ml) and fractions containing catalytic activity are pooled and concentrated in vacuo.

G. Thermo-Stability of rhDHFR Mutants

The mutated affinity component (0.03 mg) is incubated at 37° C. in 10 mM Tris-HCl (pH 7.5) or in normal human serum in a total volume of 0.1 ml. Aliquots withdrawn after different periods of time are assayed for catalytic and binding activity as described in Examples 11. FIG. 31 shows the thermo-stability of rhDHFR mutants containing one additional cysteine residue at position 133 (single mutation) or two additional cysteine residues at positions 39 and 69 (double mutation).

H. Thermo-Stability of rhDHFR Mutants After Reaction with Sodium Tetrathionate

Treatment of rhDHFR mutants with sodium tetrathionate is performed as described in Example 21(E). Thereafter, the mutated affinity component (0.03 mg) is incubated at 37° C. either in 10 mM Tris-HCl (pH 7.5) or in normal human serum in a total volume of 0.1 ml. Aliquots withdrawn after different periods of time, are assayed for catalytic and binding activity as described in Example 11.

EXAMPLE 22

Conjugation of the Targeting Moiety and the Affinity Component by Recombinant Technology A. Construction and Expression of a Fab'-DHFR Fusion Protein The rhDHFR gene is modified by PCR to contain a 5' SmaI site (CCCGGG) and a 3' BamHI site located immediately distal to the translation termination codon (TAAGGATCC). The PCR fragment is digested with SmaI and BamHI and directionally cloned into the SmaI and BamHI sites of pBluescript SK (Stratagene, La Jolla, Calif.). Thereafter, a tumor reactive $IgG_3$ κ human monoclonal antibody, 88BV59, is modified such that the $CH_2$ domain is deleted from the heavy chain. This modified $\Delta CH_2$ molecule contains the $IgG_3$ hinge fused in frame to the $IgG_3$ $CH_3$ domain. This is facilitated by employing site-directed mutagenesis of a PvuII site located at the 3' end of the $IgG_3$ hinge in amino acids 243 and 244, i.e. 5' CAGCGT 3'. Therefore, an 835 bp fragment containing a 5' SalI site and 3' PvuII site, encoding the complete rearranged and expressed 88BV59 heavy chain variable region, $CH_1$ domain and hinge region of human $IgG_3$ is digested with SalI and PvuII and directionally ligated into the SalI and SmaI sites of pBluescript SK vector which already contains the rhDHFR molecule as a SmaI BamHI insert. The resulting molecule contains a 5' SalI site, a fused PvuII/SmaI site and a 3' BamHI site. Since the sequence CCAGGGGATG present at the hinge/DHFR junction, contains an extra G nucleotide, the DHFR peptide is in a different translational reading frame than the 88BV59 Fab'. Therefore, a single G nucleotide is removed via site-directed mutagenesis using the BioRad mutagene kit, and the resulting fusion construct is sequenced. The in frame fusion construct contains a single glycine residue (GGG) separating the carboxy terminal amino acid 243 of the $IgG_3$ hinge and the initiator methionine residue of the rhDHFR.

Subsequently, a 155 bp fragment derived from the 3' untranslated region of the human $IgG_3$ gene containing a unique polyadenylation site is generated by PCR as a 5' BamHI 3' NotI site. This is cloned directly into pBluescript SK. The 88BV59 DHFR fusion fragment is excised as a 1400 bp 5' SalI 3' BamHI fragment and cloned directionally into the SalI and BamHI sites of the pBluescript SK containing the 155 bp 3' untranslated region from human IgG$_3$. The resulting molecule is a pBluescript SK vector containing the complete immunoglobulin 88BV59 heavy chain variable region, (CH$_1$ and hinge domains, linked by a single glycine residue to the rhDHFR gene). The human IgG$_3$ 3' untranslated region, immediately 3' of the rhDHFR, provides a unique polyadenylation site, so that the 3' end of the mRNA can be formed effectively. The pSK plasmid is digested with SalI and NotI excising a 1.56 Kilobase fragment composed of the complete 88BV59 Fab'-DHFR, along with a polyadenylation site. This is directionally cloned into a modified pSV$_2$-gpt expression vector which contains unique SalI and NotI sites 3' of the murine immunoglobulin heavy chain enhancer and promoter elements (Hall, et al. Can Res. 54:5178–5185 (1994)). Expression of the 88BV59 Fab'-DHFR fusion is accomplished by sequential transfection. Initially the 88BV59 light chain gene is transfected into myeloma cells, followed by transfection of the 88BV59 Fab'-DHFR construct into a light chain producer.

The 88BV59 rearranged and expressed light chain gene is cloned into a modified pSV$_2$ neo construct, transfected into myeloma cells, and G418 resistant clones which secrete 88BV59 light chain, are isolated. Clones producing kappa light chain are transfected with the 88BV59-Fab'-DHFR fusion construct and are selected for resistance to mycophenolic acid. Mycophenolic acid resistant wells are assayed for the presence of IgG κ by ELISA with Immulon-II plates coated with an affinity purified anti-human IgG reagent at 2 μ/ml and developed with an anti-human Kappa light chain HRP conjugate. Clones producing IgG, κ are subsequently cloned by limiting dilution.

B. Construction and Expression of an IgG$_1$-DHFR Fusion Protein

The 88BV59 IgG$_1$ heavy chain molecule was created as a 5' SalI 3' XbaI insert into the modified pSV$_2$ gpt vector. The unique XbaI site located at amino acid 78 and 79 of recombinant human DHFR is destroyed by changing the TCTAGA sequence to TCTTGA by site directed mutagenesis. The CTA→CTT mutation does not alter the leucine at amino acid 78. Subsequently, after confirming by DNA sequencing the absence of the XbaI site, the rhDHFR is modified by PCR to contain flanking 5' and 3' XbaI sites.

A modified pSV$_2$-gpt vector containing the intact 88BV59 IgG$_1$ gene is modified at its carboxyl terminus as follows: The 88BV59 IgG$_1$ gene contains the carboxy terminal amino acid 478 lysine (AAA) followed by two translation termination codons (TAATAG) and an XbaI site (TCTAGA). The two translation codons TAA and TAG were removed from the IgG$_1$ terminus by utilizing in a PCR, an anchored oligonucleotide that contains solely the XbaI site without any termination codons, followed by the nucleotides homologous to amino acids 478 to 473 of human IgG$_1$, i.e., 5' GATCTCTAGATTTACCCGGAGACACGGA 3'. This oligonucleotide is used along with a 5' oligonucleotide containing an anchored SalI site, a TCA (serine) encoding amino acid −1 of the leader sequence, and nucleotides encoding amino acids +1 through +6 of the 88BV59, rearranged variable heavy chain region, i.e. 5' GATCGTC-GACTCATAGGTGCAGCTGGTG 3'. PCR is performed as described in Examples 22(A). The PCR product is cleaved with SalI and XbaI and ligated into the unique SalI and Xba sites in the modified pSV$_2$-gpt vector. The complete nucleotide sequence of the rearranged and expressed 88BV59 IgG$_1$ gene is along with the absence of any termination codons at the 3' end of the IgG$_1$ gene, is confirmed by dideoxy nucleotide sequencing.

Subsequently, the 560 bp rhDHFR insert with its 5' and 3' XbaI termini is cleaved with XbaI and ligated into the unique XbaI site of the modified pSV$_2$-gpt containing the IgG, gene as described above. The modified pSV$_2$-gpt 88BV59-IgG$_1$ clones are screened for the presence of the 560 bp DHFR insert by mini-prep analysis. The correct junctional sequence at the carboxyl terminus of human IgG$_1$ and the amino acid terminus of the rhDHFR is confirmed by dideoxy nucleotide sequencing. The resulting fusion construct contain a single XbaI site (TCTAGA) which encodes two serine residues (TCT-serine, AGA-serine) linking the carboxyl terminus of human IgG$_1$ to rhDHFR. The modified pBRI gpt γ$_1$ DHFR vector was transfected into 88BV59 light chain producing cells. Mycophenolic acid resistant clones secreting IgG$_1$ were identified by IgG$_1$ κ ELISA. The presence of the DHFR molecule on the heavy chain of IgG, is confirmed both by Western blot analysis using antisera directed to the human IgG$_1$ heavy chain and antisera directed against the rhDHFR.

EXAMPLE 23

Modifications of the Effector Complex

A. Synthesis of MTX-DTPA

DTPA dianhydride (9.3 mg, 25 μmol) in dimethylformamide is stirred for 5 min with 0.1 ml of triethylamine prior to addition of 2 ml acetonitrile containing 6.8 mg of MTX-α-butylester-γ-hydrazide (13 μmol) (prepared as described by Rosowsky et al (J. Med. Chem. 24:2450–2455, 1981). The stirring is continued overnight at room temperature. Following evaporation of the solvents, the residue is heated at 50° C. with 1N HCl for 1 hr. The reaction mixture is evaporated to dryness and the residue is purified by C$_{18}$ reverse phase HPLC. The gradient mobile phase consists of 2% acetic acid (pump A) and 2% acetic acid in 50% ethanol (pump B). The yield of the product is 40% of the starting material.

B. Synthesis of MTX-LILO

3-Bis[N-[N-(2-aminoethyl)-2-aminoethyl]-2-aminoacetamido]-2-(4-isothiocyanatobenzyl)propane-N, N,N',N'',N''',N'''',N''''',N''''''-octacetic acid (LiLo isothiocyanate) (50 mg, 25 μmol), prepared as described by Subramanian et al. (Bioconjugate Chem., 2:248–255, 1992, incorporated herein by reference) is dimethyl formamide is added to 0.1 ml triethylamine. The mixture is stirred for 5 min before 2 ml acetonitrile containing 6.8 mg MTX-AB-GH (13 μmol) is added. MTX-AB-GH 6.8 mg (13 μmol) in 2 ml of acetonitrile is added to the above mixture and stirred overnight at room temperature. Solvents were evaporated and the residue is heated to 50° C. with 1N HCl for 1 hour. The product is purified as described in Example 13.

C. Radiolabeling of MTX-Chelator Conjugates with Indium-111

MTX chelators conjugates are radiolabeled with indium-111 as follows. To an aqueous solution containing an MTX-chelator conjugate (10 mg/ml, 0.5–1.0 mg), 60 mM sodium citrate solution, pH 5.5, (0.02–0.2 ml) and 600 mM sodium acetate solution, pH 5.5, (0.01 ml–0.1 ml) are added. This is followed by the addition of 1–2 mCi of indium-111 chloride. The reaction mixture is allowed to incubate at room temperature for 30 to 180 minutes. The efficiency of radiolabeling is determined by analyzing 1 ul of the reaction mixture using thin layer chromatography on a plastic backed silica strip (Merck, Darmstadt, Germany) using a 1:1 solvent mixture of 10% ammonium acetate and methanol. The general reaction conditions pertaining to radiolabeling can be further modified as per: Subramanian, R., and Mecues, C. F., (1990), Bifunctional chelating agents for radiometal labeled monoclonal antibodies, in Cancer Imaging with Radiolabeled Antibodies' (D. M. Goldenberg, Ed.,) pp. 239–312, Kluwer Academic, Boston).

D. Radiolabeling of MTX-chelator Conjugate with Yttrium-90

MTX chelators conjugates are radiolabeled with yttrium-90 as follows. To an aqueous solution containing an MTX-chelator conjugate (10 mg/ml, 0.5–1.0 mg), 60 mM sodium citrate solution, pH 5.5, (0.02–0.2 ml) and 600 mM sodium acetate solution, pH 5.5, (0.01 ml–0.1 ml) are added. This is followed by the addition of 1–2 mCi of yttrium-90 chloride. The reaction mixture is allowed to incubate at room temperature for 30 to 180 minutes. The efficiency of radiolabeling is determined by analyzing 1 ul of the reaction mixture by thin layer chromatography on a plastic backed silica strip (Merck, Darmstadt, Germany) using a 1:1 solvent mixture of 10% ammonium acetate and methanol. MTX chelator conjugates can also be radiolabeled with Y-90 in the presence of other buffers such as 0.1 M ammonium citrate, pH 5.0.

E. Synthesis of Effector Complexes Containing More Than One Binding Partner

An MTX-derivatized oligopeptide consisting of more than one Glu-Ala-Lys(MTX)-Ala units is used to conjugate more than one binding partner to a single chelator moiety. FIG. 33 shows an example of an effector complex containing 3 MTX residues attached to a single chelator moiety via three Glu-Ala-Lys-Ala tetrapeptide units.

Figure 34:
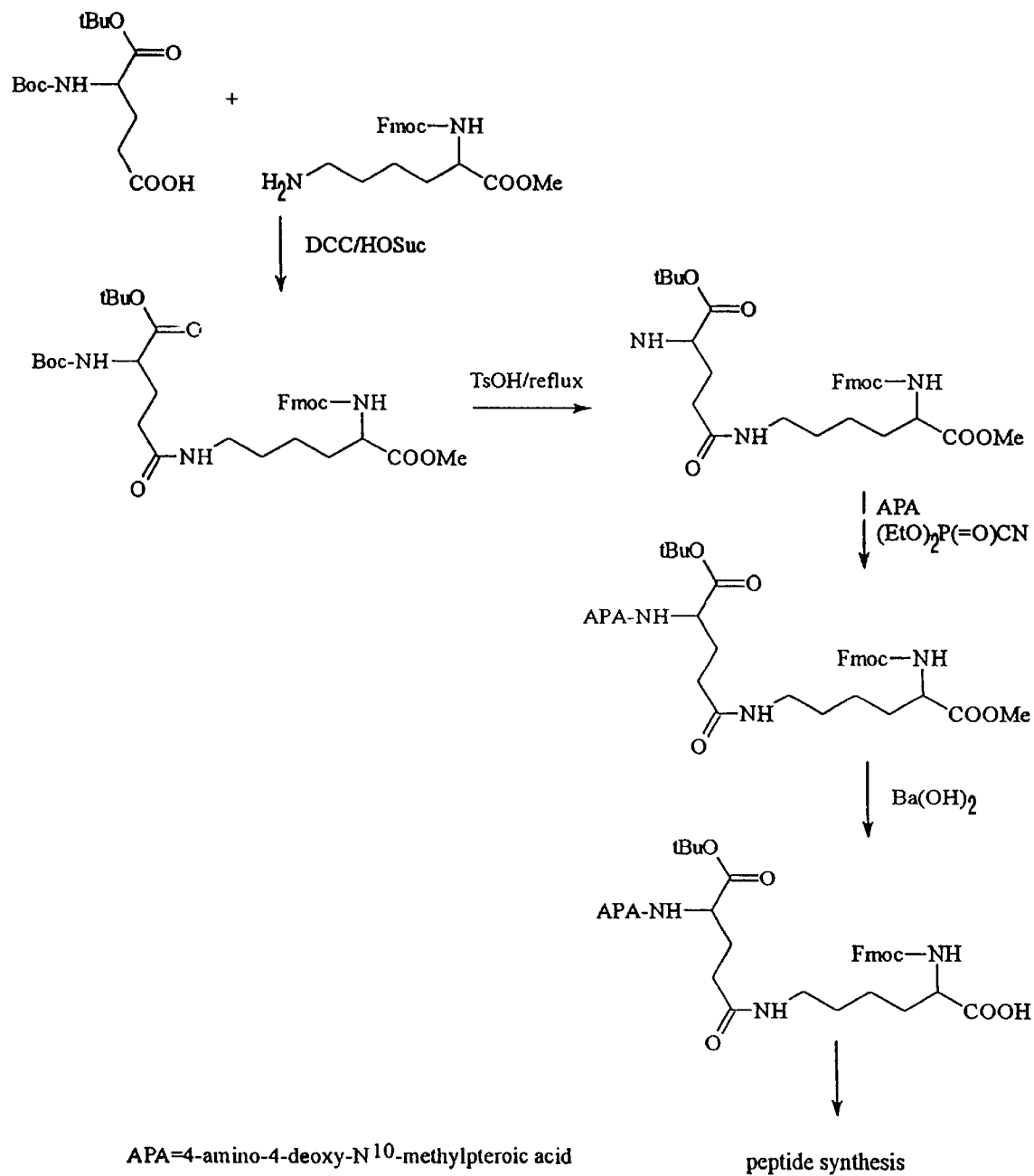
FIG. 34 is the scheme for the synthesis of an MTX-α-BUTYLESTER- γ-LYSYL derivative.

MTX is incorporated as an Fmoc-protected lysine derivative that is suitable for the synthesis of MTX-derivatized oligopeptides using a solid-phase peptide synthesizer. FIG. 34 shows scheme for the synthesis of such an MTX-lysine derivative (description of synthesis).

After cleavage of the MTX-derivatized oligopeptide from the solid phase, its α-amino group is modified by covalent attachment of DTPA dianhydride (description of the synthesis).

EXAMPLE 24

In Vivo Administration of the System Components

A. Biodistribution of Intravenously Administered $^{111}$IN-DTPA-MTX in Mice

Figure 35A:
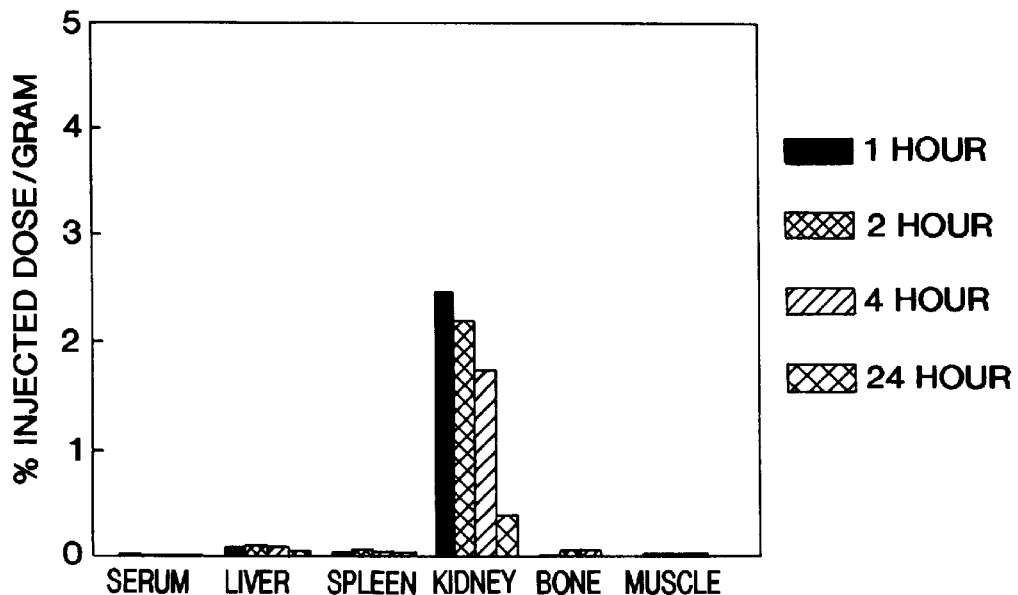
FIGS. 35 (A and B) show the biodistribution of intravenously administered $^{111}$-In-DTPA-MTX in mice.
Figure 35B:
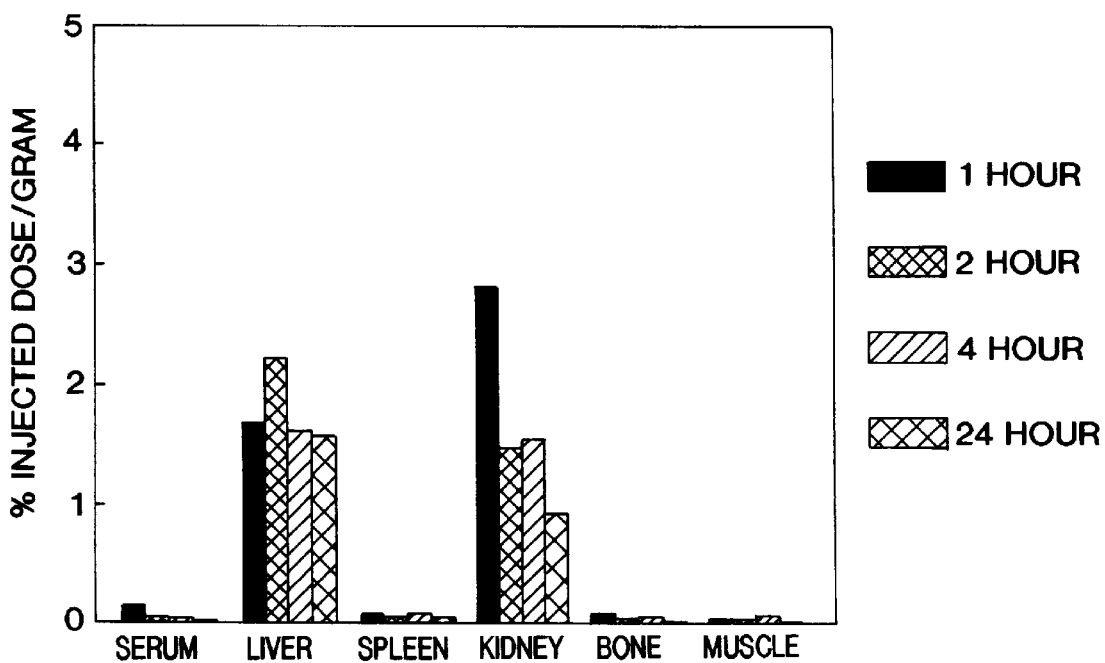

In order to compare the biodistribution and clearance of $^{111}$In-DTPA-MTX with that of $^{111}$In-DTPA in the nude mouse, $^{111}$In-DTPA-MTX is administered at a dose of 9 μg and 8 μCi and $^{111}$In-DTPA is administered at a dose of 9 μg and 7 μCi by intravenous injection into the lateral tail vein. Animals are sacrificed a 1, 2, 4 and 24 hours after injection in groups of three animals per time point. FIG. 35 shows that the clearance of both agents is very rapid with less than 0.2% of the injected dose per gram (ml) remaining in the serum as early as 1 hour post injection. Clearance takes place via the urine as evidenced by activity in the kidney at all time points following injection. In addition, there is low uptake of the MTX conjugate in the liver which is not seen with the labeled DTPA.

B. Biodistribution of Intravenously Administered $^{111}$IN-DTPA-MTX in Rabbits

Figure 36A:
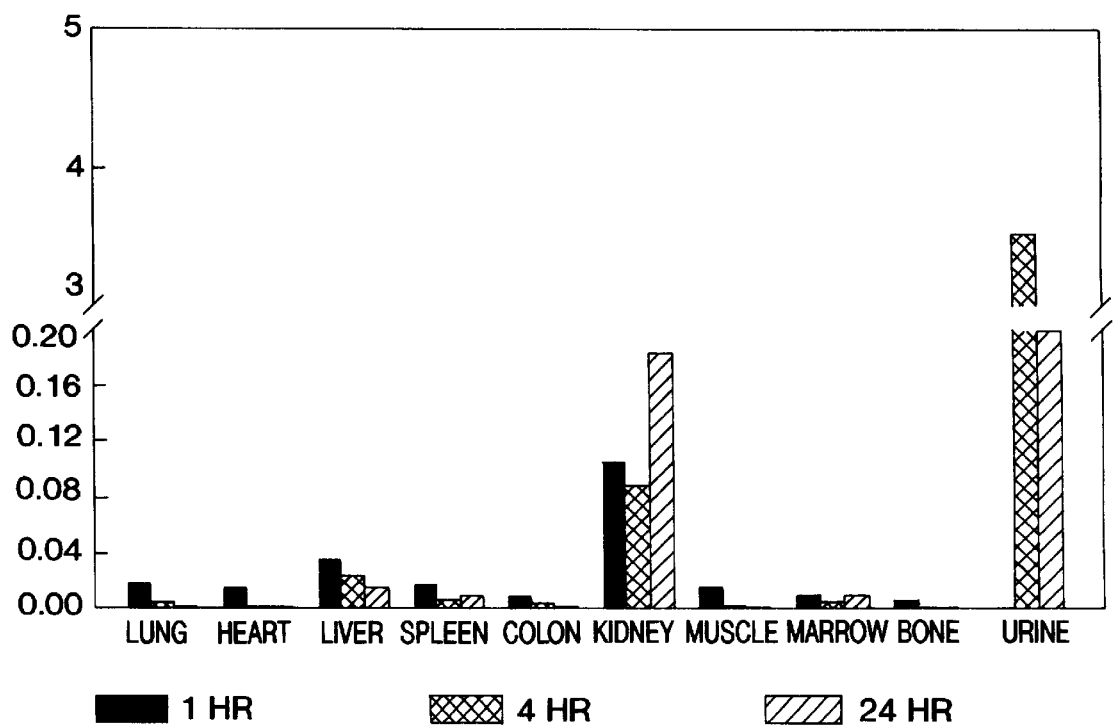
FIGS. 36 (A and B) show the biodistribution of intravenously administered $^{111}$-In-DTPA-MTX in rabbits.
Figure 36B:
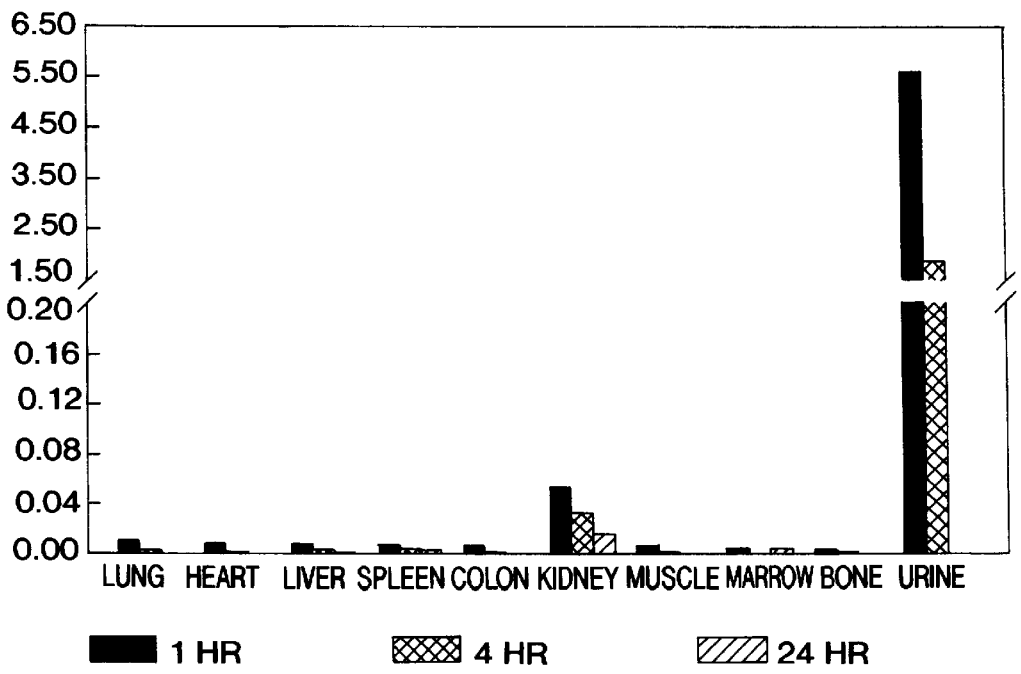

In order to compare the biodistribution and clearance of $^{111}$In-DTPA-MTX with that of $^{111}$In-DTPA in the New Zealand white rabbit, approximately 140–190 μg and 120 μCi of each agent is administered to three animals each by intravenous injection in the central ear artery. One animal of each group is sacrificed at 1, 4 and 24 hours after injection. As shown in FIG. 36, clearance takes place via the urine as evidenced by high urine activity levels collected at time of sacrifice. Low activity levels are seen in the kidney for both groups and in the liver in the MTX group.

C. Targeting of Antibody-rhDHFR Conjugates in Tumor Bearing Nude Mice

Preparation of an $^{111}$In-Labeled SC20 Antibody-rhDHFR Conjugate

The labeled immunoconjugate is prepared in four steps as follows:

Reaction I. The antibody is modified with both sulfo-LC-SPDP and DTPA.

Reaction II. The affinity component is modified with sulfo-LC-SPDP, and followed by reduction with DTT.

Reaction III. Conjugation of the affinity component with the modified IgG.

Reaction IV. Labeling the immunoconjugate with $^{111}$-Indium.

Reaction I

Anti-CEA IgG (12.48 mg, 78nmol) is derivatized together with 5-and 20-fold molar excess of sulfo-LC-SPDP and DTPA respectively in 50 mM sodium borate buffer (pH 8.5) in a total volume of 1.2 ml. The reaction is run for 45 min at room temperature before the excess reagents are removed by gel-filtration on Sephadex G-25 using PBS as eluant. The buffer is washed with CHELEX 100 (100–200 mesh, sodium free) to get rid off any metal ions.

Reaction II

The affinity component (55 nmol) is modified with 20-fold molar excess of sulfo-LC-SPDP in 50 mM sodium borate buffer (pH 8.5) in a total volume of 0.2 ml. The reaction is run at room temperature for 30 min and is followed by reduction with 2 mg of solid DTT for 15 min at room temperature. The enzyme is then purified by gel filtration on Sephadex G-25 using PBS as the eluant. The buffer is treated in the same way as mentioned above.

Reaction III

The purified IgG from reaction I is added to the purified affinity component from reaction II, and the reaction is incubated for overnight at room temperature under nitrogen. The immunoconjugate is purified by gel filtration on Sephadex G-100 using PBS treated in the same way as described.

Reaction IV

The immunoconjugate (0.087 mg) is mixed with $^{111}$InCl$_3$ (0.1–1 mCi) in an acid-washed eppendorf tube containing a two-volumes 60 mM of sodium citrate buffer (pH 5.5) and one volume of 60 mM sodium acetate buffer (pH 5.5). The reaction is continued at room temperature for 30 min before it is terminated with 1 mM DTPA solution. The volume of DTPA solution is usually 5–10% of the entire reaction volume. The labeled immunoconjugate is then purified by gel filtration on Sephadex G-50 using PBS as the eluant. The radiolabeled antibody elutes off the column in the first peak. The percentage of $^{111}$In bound to the antibody was determined using thin layer chromatography (solvent system— 1:1 (v/v) mixture of 10% ammonium acetate and methanol).

Development of LS-174 Tumors in Nude Mice

LS174t cells, a well characterized human colonic adenocarcinoma, grows well in culture and, in vivo, after injection into mice. The cell line maintained at PerImmune, Inc. was originally obtained from the American Type Culture Collection, Rockville, Md. LS174t cells are grown in growth media consisting of Dulbecco's Modified Eagle's Medium, Fetal Bovine Serum, non-essential Amino Acids, and L-glutamine. Cells are harvested for experiments by washing cells in phosphate buffered saline, trypsinizing with 0.25% trypsin for several minutes, and centrifuging the suspension at 1500 rpm for 10 minutes. The pellet is then resuspended in Hanks Balanced Salt Solution to the appropriate volume. Cells are kept on wet ice until injection. Each animal typically receives approximately 3×10$^6$ LS174t cells as a subcutaneous injection in the right lateral thoracic region. Tumors reach experimental size (0.8–1.3 cm in at least one dimension in eight to eleven days.

Figure 37A:
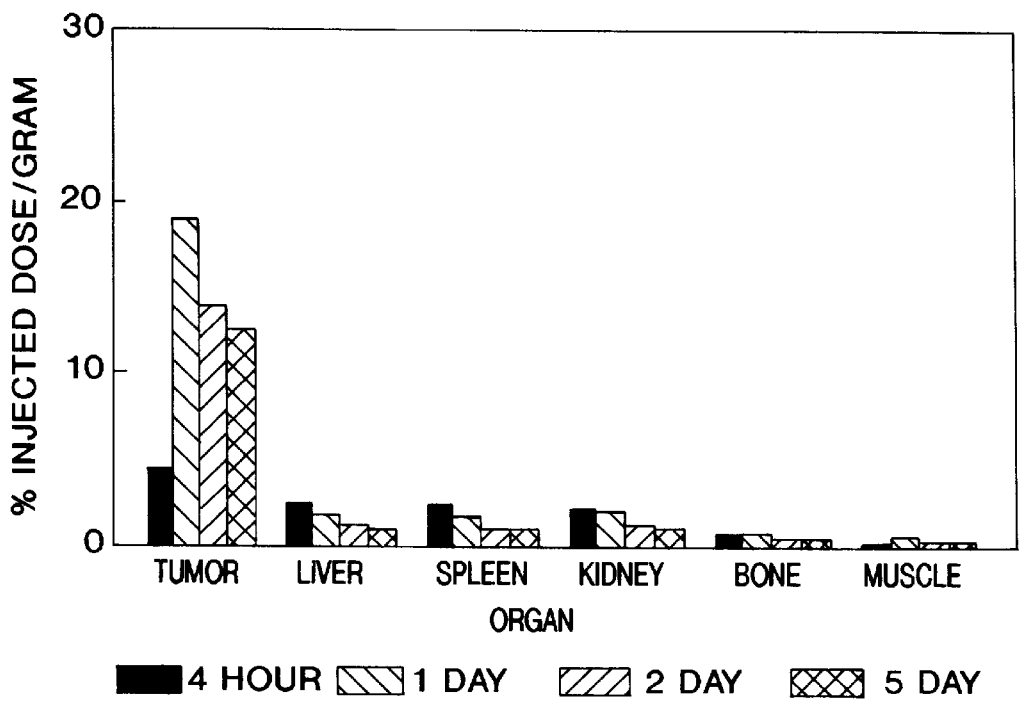
FIGS. 37 (A and B) show the biodistribution of intravenously administered SC-20 antibody in LS-174 tumor bearing nude mice.
Figure 37B:
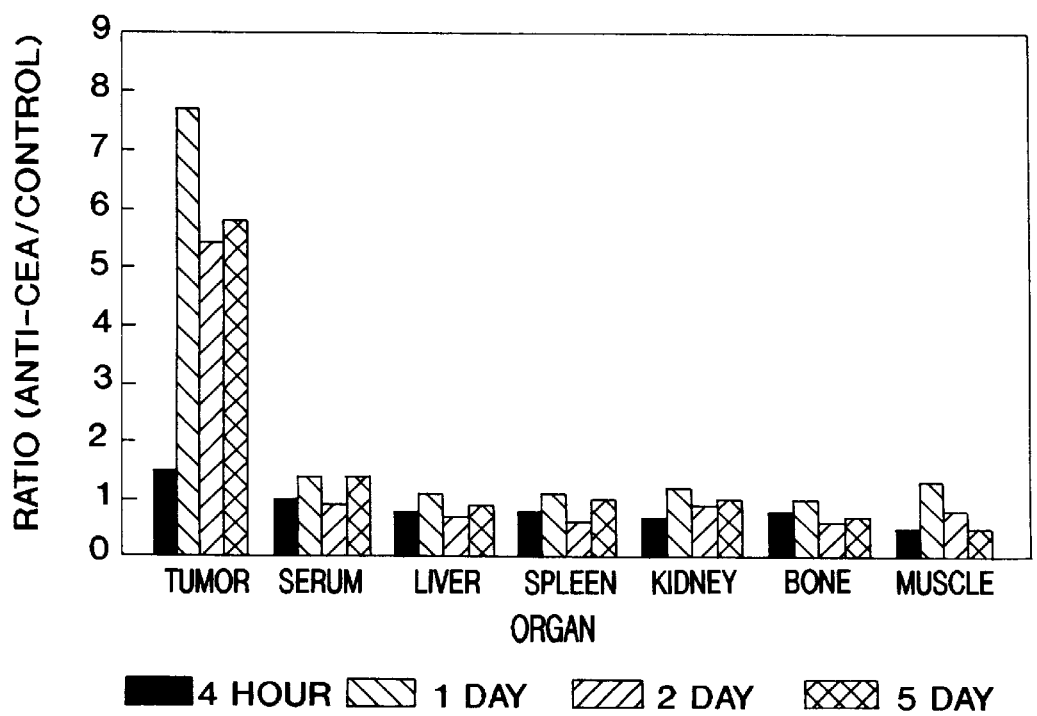
Figure 38:
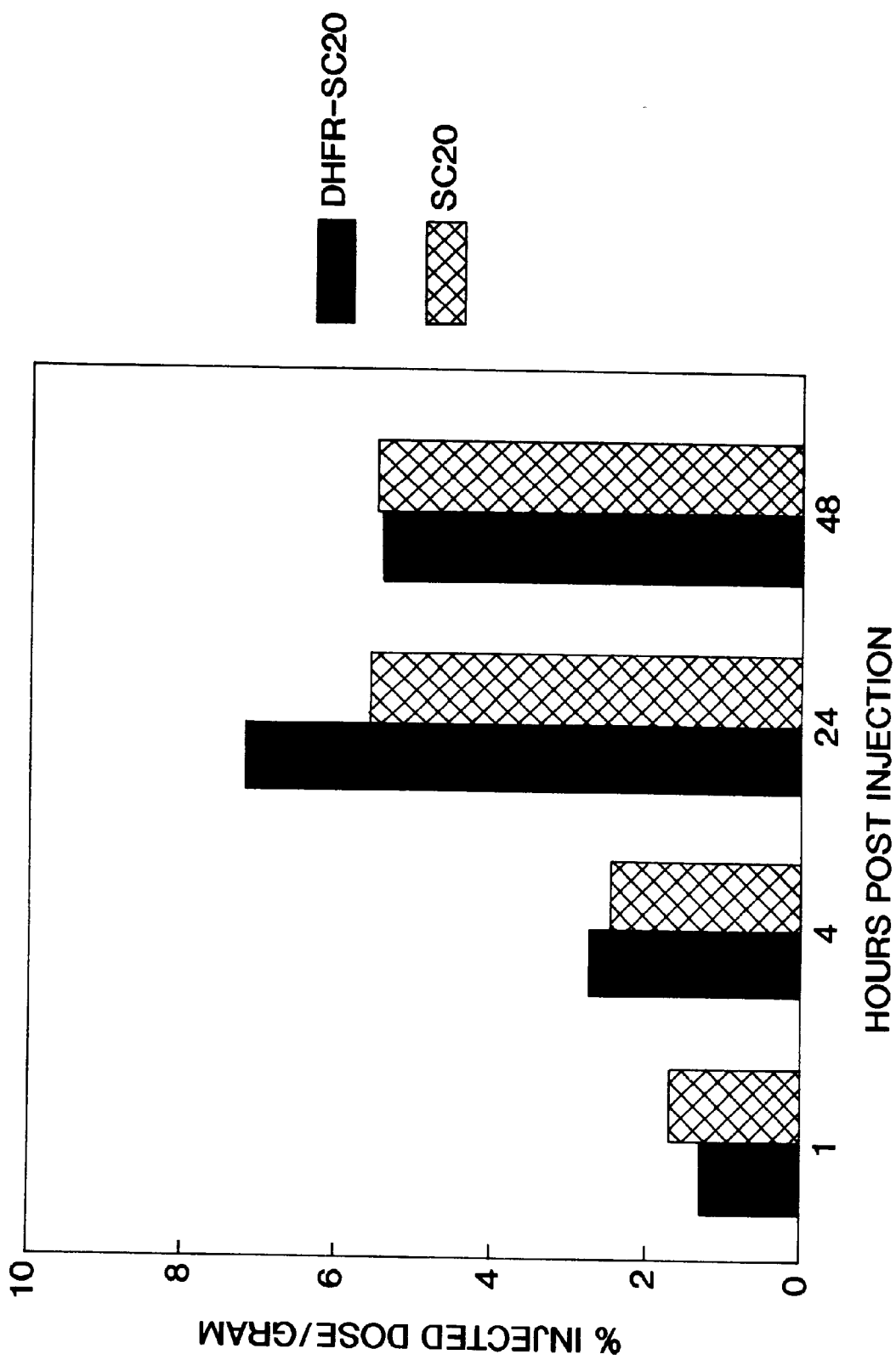
FIG. 38 shows the distribution of intravenously administered SC-20-rhDHFR in LS-174 tumor bearing nude mice.

Distribution of Intravenously Administered SC-20-rhDHFR Conjugates in LS174 Tumor Bearing Mice Twelve animals each are injected intravenously in the lateral tail vein with 0.5 ml of the SC20-rhDHFR conjugate of (50 µg, 10 µCi), unconjugated SC-20 antibody (50 µg, 10 µCi) or unconjugated non-specific antibody (myeloma, 50 µg, 10 µCi). Animals are sacrificed in groups of three at 1, 4, 24 and 48 hours post administration of labeled SC20 rhDHFR conjugate or unconjugated antibodies. The tumors and normal tissues are harvested, weighed, and the amount of deposited radioactivity is determined by gamma counting. FIG. 37 shows that the unconjugated SC-20 antibody localized to a significant extent (5–7 fold) in the LS174 tumors as compared to a non-specific myeloma protein. FIG. 38 shows that the attachment of rhDHFR to the SC-20 antibody does not affect the ability of the antibody to target LS-174 tumors in vivo.

D. Two Step Delivery of $^{111}$Indium using an MTX-Stabilized Affinity Component An Alzet miniature osmotic pump (Alza Corporation, Palo Alto, Calif.) containing MTX is implanted intraperitoneally into mice carrying LS174 tumors with a size of approximately 0.8–1.5 cm in at least one dimension. The pump provides a continuous delivery of MTX to the animal for seven days. Two days after implantation of the pump, the animals are injected into the lateral tail vein with 50 µg of rhDHFR-SC20. After an additional two days, radiolabeled $^{111}$In-DTPA-MTX (approximately 50 µCi) is administered to the animals. Under these conditions, significant uptake of $^{111}$Indium is observed in the LS174 tumors.

We claim:

1. A method for treating a patient by administration of a non-radioactive targeting reagent at an effective dose, said targeting reagent comprising a targeting moiety and one or more thermo-stabilized affinity components for non-covalent binding to an effector complex, represented by the following formula:

$$T\text{-}(L\text{-}A)_n$$

wherein:

T is a targeting moiety;

L is a chemical bond or a linking group that may contain one or more functional groups;

A is a thermo-stabilized enzyme; and n is an integer greater than 0;

followed by the administration of an effector complex after accumulation of the targeting reagent at the target site and clearance of non-bound targeting reagent from the circulation, said effector complex comprising one or more binding partners to the affinity component and one or more effector molecules, represented by the following formula:

$$(B)_x\text{-}(L)_y\text{-}(E)_x$$

wherein:

B is enzyme inhibitor which has an affinity for non-covalent binding to the affinity component;

L is a chemical bond or a linking group that may contain one or more functional groups;

E is the effector molecule; and x, y and z are integers greater than 0.

2. A method for treating a patient by administration of a targeting reagent at an effective dose, said targeting reagent comprising a fusion protein with a coding region of a targeting moiety fused in frame to a coding region of rhDHFR, mutants of rhDHFR, or functional fragments thereof, followed by the administration of an effector complex after accumulation of the targeting reagent at the target site and clearance of non-bound targeting reagent from the circulation, said effector complex comprising one or more binding partners to the affinity component and one or more effector molecules, represented by the following formula:

$$(B)_x\text{-}(L)_y\text{-}(E)_z$$

wherein:

B is an enzyme inhibitor which has an affinity for non-covalent binding to an affinity component;

L is a chemical bond or a linking group that may contain one or more functional groups;

E is the effector molecule; and x, y and z are integers greater than 0.

* * * * *